(12) United States Patent
Madsen, II et al.

(10) Patent No.: US 10,632,141 B2
(45) Date of Patent: Apr. 28, 2020

(54) MALTOSYL-ISOMALTOOLIGOSACCHARIDES

(71) Applicant: ISOThrive Inc., Healdsburg, CA (US)

(72) Inventors: Lee Madsen, II, Manassas, VA (US); Jack Oswald, Healdsburg, CA (US)

(73) Assignee: ISOThrive Inc., Healdsburg, CA (US)

( * ) Notice: Subject to any disclaimer, the term of this patent is extended or adjusted under 35 U.S.C. 154(b) by 203 days.

(21) Appl. No.: 15/409,223

(22) Filed: Jan. 18, 2017

(65) Prior Publication Data

US 2017/0202869 A1    Jul. 20, 2017

Related U.S. Application Data

(60) Provisional application No. 62/280,026, filed on Jan. 18, 2016.

(51) Int. Cl.
| | |
|---|---|
| *A61K 31/715* | (2006.01) |
| *A23L 33/125* | (2016.01) |
| *A61K 9/08* | (2006.01) |
| *A61K 9/14* | (2006.01) |
| *C12P 19/04* | (2006.01) |

(52) U.S. Cl.
CPC .......... *A61K 31/715* (2013.01); *A23L 33/125* (2016.08); *A61K 9/08* (2013.01); *A61K 9/14* (2013.01); *C12P 19/04* (2013.01)

(58) Field of Classification Search
CPC .......... A61K 31/715; A61K 9/08; A61K 9/14; C12P 19/04
USPC ......................................................... 514/54
See application file for complete search history.

(56) References Cited

U.S. PATENT DOCUMENTS

| | | | |
|---|---|---|---|
| 2004/0235789 A1* | 11/2004 | Day | A61K 31/715 514/54 |
| 2008/0064657 A1 | 3/2008 | Day et al. | |
| 2010/0284972 A1 | 11/2010 | Naeye | |

FOREIGN PATENT DOCUMENTS

| | | |
|---|---|---|
| KR | 20150031959 A | 3/2015 |
| WO | 2016029198 | 2/2016 |
| WO | 2017127436 | 7/2017 |

OTHER PUBLICATIONS

"International Application Serial No. PCT/US2017/013957, Written Opinion dated Apr. 20, 2017", 9 pgs.
"International Application Serial No. PCT/US2017/013957, International Search Report dated Apr. 20, 2017", 4 pgs.
Fernandez-Arrojo, Lucia, "Transformation of maltose into prebiotic isomaltooligosaccharides by a novel a-glucosidase from Xantophyllomyces dendrorhous", Process Biochemistry, vol. 42, No. 11, (2007), 26 pgs.
Lee, Min Sung, "Optimized substrate concentrations for production of long-chain isomaltooligosaccharides using dextransucrase of Leuconostoc mesenteroides B-512F", Journal of Microbiology and Biotechnology, vol. 18, No. 6, (2008), 1141-1145 pgs.
Yoo, Sun-Kyun, "A simple batch fermentation for production of isomaltooligosaccharides by Leuconostoc mesenteroidesFood Science and", Food Science and Biotechnology, vol. 13, No. 2, (2004), 5 pgs.
"International Application Serial No. PCT US2017 013957, International Preliminary Report on Patentability dated Aug. 2, 2018", 11 pgs.
"European Application Serial No. 17741856.3, Response filed Feb. 4, 2019 to Office Action dated Aug. 31, 2019", 9 pgs.
"European Application Serial No. 17741856.3, Extended European Search Report dated Sep. 17, 2019", 9 pgs.
Cho, Seung Kee, et al., "Simple Synthesis of Isomaltooligosaccharides during Sauerkraut Fermentation by Addition of Leuconostoc Starter and Sugars", Food Science and Biotechnology; vol. 24, No. 4, (Aug. 31, 2015), 1443-1446.
Moon, Young Hawn, et al., "Lime application for the efficient production of nutraceutical glucooligosaccharides fromLeuconostoc mesenteroidesNRRL B-742", Journal of Industrial Microbiology and Biotechnology, Basingstoke, GB, vol. 42, No. 2, (Dec. 23, 2014), 279-285.

* cited by examiner

Primary Examiner — Shaojia A Jiang
Assistant Examiner — Michael C Henry
(74) Attorney, Agent, or Firm — Schwegman Lundberg & Woessner, P.A.

(57) ABSTRACT

The application describes compositions that include maltosyl-isomalto-oligosaccharides with a desirable mass average molecular weight distribution. In some cases, the compositions can contain at least 3% mannitol.

23 Claims, 42 Drawing Sheets

| lot # 151105 | %/brix: |
|---|---|
| Brix | 63.01 |
| mannitol | 6.23 |
| glucose | 0.85 |
| fructose | 0.16 |
| sucrose | 1.86 |
| maltose | 4.29 |
| MIMO | 84.77 |
| Lactate | 0.00 |
| Glycerol | 0.41 |
| Formate | 0.00 |
| Acetate | 0.00 |
| TOTAL, %: | 98.58 |
| Purity, %: | 86.00 |
| MWD, Da: | 776.47 |

| DP: | %/brix: |
|---|---|
| MIMO-DP3 | 14.89 |
| MIMO-DP4 | 22.19 |
| MIMO-DP5 | 23.66 |
| MIMO-DP6 | 15.23 |
| MIMO-DP7 | 5.75 |
| MIMO-DP8 | 2.48 |
| MIMO-DP9 | 0.58 |

| | α-(1,6), %: | α-(1,3), %: |
|---|---|---|
| HPLC, %: | 90.34 | 10.12 |
| NMR, %: | 95.65 | 4.35 |

FIG. 39

| Component | %/brix: |
|---|---|
| Glucose | 0.35 |
| Fructose | 0.01 |
| Sucrose | 0.34 |
| Maltose | 6.56 |
| MIMO | 50.29 |
| Mannitol | 25.02 |
| Lactate | 10.210 |
| Glycerol | 0.828 |
| Formate | 0.120 |
| Acetate | 4.547 |
| TOTAL: | 98.28 |
| MIMO: | 50.29 |
| Purity, %: | 51.17 |
| Mw, Da: | 642.46 |

|  | %/brix |
|---|---|
| MIMO-DP3 | 14.69 |
| MIMO-DP4 | 20.17 |
| MIMO-DP5 | 11.92 |
| MIMO-DP6 | 2.88 |
| MIMO-DP7 | 0.62 |
| MIMO-DP8 | 0.00 |
| MIMO-DP9 | 0.00 |

FIG. 40

| Component | %/brix: | | %/brix |
|---|---|---|---|
| Glucose | 0.11 | | |
| Fructose | 0.08 | MIMO-DP3 | 7.66 |
| Sucrose | 0.73 | MIMO-DP4 | 17.24 |
| Maltose | 0.67 | MIMO-DP5 | 17.17 |
| MIMO | 52.19 | MIMO-DP6 | 7.20 |
| Mannitol | 27.11 | MIMO-DP7 | 2.02 |
| Lactate | 11.66 | MIMO-DP8 | 0.89 |
| Glycerol | 0.20 | MIMO-DP9 | 0.00 |
| Formate | 0.03 | | |
| Acetate | 5.10 | | |
| TOTAL: | 97.89 | | |
| Purity, %: | 53.32 | | |
| Mw, Da: | 760.73 | | |

FIG. 41

| Component | %/brix: |
|---|---|
| Glucose | 0.46 |
| Fructose | 0.05 |
| Sucrose | 1.75 |
| Maltose | 4.39 |
| MIMO | 95.51 |
| Mannitol | 8.35 |
| Lactate | 0.00 |
| Glycerol | 0.51 |
| Formate | 0.00 |
| Acetate | 0.00 |
| TOTAL: | 111.03 |
| Purity, %: | 86.02 |
| Mw, Da: | 789.46 |

| | %/brix |
|---|---|
| MIMO-DP3 | 11.89 |
| MIMO-DP4 | 28.06 |
| MIMO-DP5 | 28.67 |
| MIMO-DP6 | 16.77 |
| MIMO-DP7 | 6.58 |
| MIMO-DP8 | 2.80 |
| MIMO-DP9 | 0.73 |

FIG. 42

MALTOSYL-ISOMALTOOLIGOSACCHARIDES

CROSS REFERENCE TO RELATED APPLICATIONS

This application claims benefit of priority to the filing date of U.S. Provisional Application Ser. No. 62/280,026, filed Jan. 18, 2016, the contents of which are specifically incorporated herein by reference in their entity.

BACKGROUND

Dietary supplements are either food or food constituents that purportedly provide medical or health benefits such as prevention of disease (Stephen, D. F. L., Trends in Food Sci. Tech, 1995, 6:59-61). The term typically includes the following representative classes: probiotics, prebiotics, dietary fiber, omega-3 fatty acids and antioxidants (Pandey, M. et al., Asian J. Pharm. Clin. Res., 2010, 3:11-15). Due to increasing numbers of health conscious consumers in Asia, the United States, and Europe, the dietary supplement market, specifically in the area of oligosaccharides and prebiotics, has demonstrated significant growth over the last three decades (Goffin, D. et al., Crit. Rev. Food. Sci. Nutr., 2011, 51:394-409; Roberfroid, M. B., Br. J. Nutr., 2002, 88 Suppl 2:S133-8). New, improved products as well as new, economical methods for their production are in demand.

Prebiotics are materials, or mixtures thereof, that contain either physical (e.g. dietary fiber) or chemical (e.g. butyrate) entities that can survive transit through the upper gastrointestinal tract, and can arrive intact in the colon to promote the growth of selected beneficial (probiotic) flora (Chung, C. H., et al., Poult. Sci., 2004, 83:1302-6). In some cases, prebiotics can exert some beneficial effect directly on intestinal epithelial cells such as improving uptake of nutritive calories, vitamins, minerals, and other beneficial materials. Because many prebiotics can overcome the resistance of the digestive barrier to facilitate the proliferation and/or activity of desired populations of bacteria in situ (Gibson G. R. et al., J. Nutr., 1995, 125:1401-12; Van Loo, J. et al., Br. J. Nutr., 1999, 81:121-32), research and development in this area has boomed. Additionally, some prebiotics are naturally present in the food supply, especially in fermented foods, and are generally compatible with most food formulations (Macfarlane, S. et al., Aliment Pharmacol. Ther, 2006, 24:701-14; Manning, T. S. et al., Best Pract. Res. Clin. Gastroenterol, 2004, 18:287-98).

Some resistant glucooligosaccharide prebiotic agents may be commercially available, but some types of glucooligosaccharides are better prebiotic agents than others.

Day & Chung have produced glucooligosaccharides, including maltosyl-isomaltooligosaccharides (MIMOs) via fermentation (U.S. Pat. No. 7,291,607). However, Day & Chung do not disclose the compositions or the methods of production described in this application.

SUMMARY

Compositions described herein contain resistant oligosaccharides, where maltose is a constituent part. Referred to as maltosyl-isomaltooligosaccharides (MIMOs), these compositions promote the growth of beneficial intestinal bacteria, including *Lactobacillus* and/or *Bifidobacterium* spp., over non-beneficial bacteria in the intestine.

The application describes compositions and methods of production thereof that include, for example, maltosyl-isomaltooligosaccharides with a mass average molecular weight distribution of about 300 to 1500 daltons, or about 400 to 1200 daltons, or about 640 to 1000 daltons. In some cases, the mass average molecular weight distribution of the maltosyl-isomaltooligosaccharides is about 730 to 900 daltons. The maltosyl-isomaltooligosaccharides in the compositions generally contain more $\alpha$-(1-6) glucosyl linkages than $\alpha$-(1,2), $\alpha$-(1,3), or $\alpha$-(1,4) glucose linkages. For example, the maltosyl-isomaltooligosaccharides can have at least 50% $\alpha$-(1,6) glucosyl linkages, or at least 52% $\alpha$-(1,6) glucosyl linkages, or at least 55% $\alpha$-(1,6) glucosyl linkages, or at least 60% $\alpha$-(1,6) glucosyl linkages, or at least 65% $\alpha$-(1,6) glucosyl linkages, or at least 70% $\alpha$-(1,6) glucosyl linkages, or at least 75% $\alpha$-(1,6) glucosyl linkages, or at least 80% $\alpha$-(1,6) glucosyl linkages, or at least 83% $\alpha$-(1,6) glucosyl linkages, or at least 85% $\alpha$-(1,6) glucosyl linkages, or at least 87% $\alpha$-(1,6) glucosyl linkages, or at least 88% $\alpha$-(1,6) glucosyl linkages, or at least 89% $\alpha$-(1,6) glucosyl linkages, or at least 90% $\alpha$-(1,6) glucosyl linkages. Some of the maltosyl-isomaltooligosaccharides in the composition can optionally have one or two $\alpha$-(1,4) glucosyl linkages, or one or two $\alpha$-(1,2) glucosyl linkages, or one or two $\alpha$-(1,3) glucosyl linkages. Hence, the maltosyl-isomaltooligosaccharides are generally linear $\alpha$-(1,6) glucooligosaccharides, terminated with maltose at the reducing end. The sugar residues at the reducing ends of the maltosyl-isomaltooligosaccharides are typically connected to the rest of the MIMO molecule via an $\alpha$-(1,4) linkage.

While in some cases the compositions can have little or no mannitol, the compositions typically have some mannitol in them. For example, the compositions can have more than 3%/brix mannitol, or more than 4% %/brix mannitol, or more than 5% %/brix mannitol, for example, as detected by refractive HPAEC-PAD or HPLC-RID. Generally, the amount of mannitol in the compositions is less than 30%/brix mannitol, or less than 20%/brix mannitol, or less than 15%/brix mannitol or less than 12%/brix mannitol, or less than 10%/brix mannitol, or less than 9%/brix mannitol, or less than 8%/brix mannitol, for example, as detected by HPAEC-PAD or HPLC-RID.

The maltosyl-isomaltooligosaccharides in the compositions generally have no more than about 17 glucosyl units, or no more than about 16 glucosyl units, or no more than about 15 glucosyl units, or no more than about 14 glucosyl units, or no more than about 13 glucosyl units, for example, as detected by HPAEC-PAD or HPLC-RID.

The compositions generally have less than 2%/brix isomaltose, or less than 1%/brix isomaltose, or less than 0.5%/brix isomaltose, or less than 0.2%/brix isomaltose, or less than 0.1%/brix isomaltose as detected by HPAEC-PAD or HPLC-RID. In some cases, the compositions have no isomaltose, or levels below the detection limit (for example, as detected by HPAEC-PAD or HPLC-RID).

The compositions also generally have less than 5%/brix free glucose, or less than 4%/brix free glucose, or less than 3%/brix free glucose, or less than 2%/brix free glucose, or less than 1%/brix free glucose, for example, as detected by HPAEC-PAD or HPLC-RID.

The compositions also typically have less than 5%/brix sucrose, or less than 4%/brix sucrose, or less than 3%/brix sucrose, or less than 2%/brix sucrose, for example, as detected by HPAEC-PAD or HPLC-RID.

The compositions also generally have less than 4%/brix fructose, or less than 3%/brix fructose, or less than 2%/brix fructose, or less than 1%/brix fructose, or less than 0.5%/brix fructose, or less than 0.25%/brix fructose, for example, as detected by HPAEC-PAD or HPLC-RID.

The compositions typically contain small or non-detectable quantities of organic acids such as lactic acid, acetic acid or formic acid. For example, the compositions can have less than 16%/brix lactic acid, acetic acid and formic acid; less than 3%/brix lactic acid, acetic acid and formic acid; less than 2%/brix lactic acid, acetic acid and formic acid; or less than 1%/brix lactic acid, acetic acid, and formic acid; or less than 0.5%/brix lactic acid, acetic acid, and formic acid; or less than 0.2%/brix lactic acid, acetic acid, and formic acid; or less than 0.1%/brix lactic acid, acetic acid, and formic acid, for example, as detected by HPAEC-PAD or HPLC-RID. In some cases, the compositions can have no organic acids such as lactic acid, acetic acid or formic acid, as measured by HPAEC-PAD or HPLC-RID.

The compositions also have low amounts of free maltose. For example, the compositions typically have less than 8%/brix maltose, or less than 7%/brix maltose, or less than 6%/brix maltose, or less than 5%/brix maltose, for example, as detected by HPAEC-PAD or HPLC-RID.

The compositions can be administered or ingested by animals, including humans, domesticated animals, zoo animals, and wild animals. Hence, methods are described herein that involve administering any of the compositions described herein to an animal. Such administration or ingestion can have beneficial effects for the animal. For example, animals that can benefit from such administration or ingestion may have diseases or conditions such as cancer, pre-cancerous condition(s), cancerous propensities, diabetes (e.g., type 2 diabetes, or type 1 diabetes), autoimmune disease(s), acid reflux, bacterial infections (e.g., in the mouth, sinuses, and/or gastrointestinal tract), vitamin deficiencies, mood disorder(s), degraded mucosal lining(s), ulcerative colitis, digestive irregularities (e.g., Irritable Bowel Syndrome, acid reflux, constipation, or a combination thereof), inflammatory bowel disease, ulcerative colitis, Crohn's disease, gastroesophageal reflux disease (GERD), infectious enteritis, antibiotic-associated diarrhea, diarrhea, colitis, colon polyps, familial polyposis syndrome, Gardner's Syndrome, *Helicobacter pylori* infections, intestinal cancers, or combinations thereof. The compositions can foster the growth and activity of certain types of bacteria (e.g., *L. lactis* strains), which leads to the production of various types of bacteriocins (e.g., nisins) by those bacteria. Such bacteriocins (e.g., nisins) can act as anti-cancer agents and/or as anti-microbial agents, that can reduce the symptoms, or treat, the diseases or conditions.

The application also describes methods of making the compositions. For example, the compositions can be generated by a method that involves the following:

(a) contacting *Leuconostoc citreum* ATCC 13146 (NRRL B-742) bacterial cells with a aqueous culture medium comprising a ratio of sucrose to maltose ranging from 2.0 to about 4.5 to form a fermentation mixture;
(b) fermenting the fermentation mixture at a pH between 4 and 8;
(c) removing the bacterial cells to generate a cell-free liquor;
(d) polishing the cell-free liquor by removal of insoluble impurities;
   decolorization (e.g., using activated charcoal, activated carbon, a weak base anion resin, or a combination thereof), de-ashing (e.g., using a strong acid cation resin to remove metal ions, or using a two-step process using a strong acid followed by a weak base); removing protein (e.g., by heating, evaporating the aqueous culture medium, and centrifugation or filtration, or by using a weak base anion resin); removing organic acids (e.g., utilizing a weak base anion resin, liquid chromatography using a chromatographic grade gel-type strong acid cation exchange resin in calcium form (SAC-Ca$^{++}$); or any combination thereof, to generate a polished product;
e) washing insoluble impurities, decolorization agents, de-aching agents, evaporating mechanisms (e.g., a wiped film evaporator), centrifugation pellets, filters, ration, weak base anion resins, chromatographic resins, chromatographic grade gel-type strong acid cation exchange resins, or any combination thereof to generate one or more washes; and combining one or more washes together, or with the cell-free liquor; or with the polished product;
wherein the final composition comprises maltosyl-isomaltooligosaccharides with a mass average molecular weight distribution of about 640 to 1000 daltons and at least 3% mannitol.

In some cases, the ratio of sucrose to maltose in step (a) ranges from about 2.0 to about 4.5, or about 2.1 to about 4.0, or about 2.2 to about 3.5, or about 2.3 to about 3.0, or about 2.5 to about 3.0, or about 2.5 to about 2.9, or about 2.5 to about 2.8, or about 2.75. These ratios of sucrose to maltose are at the time of inoculation.

Because the pH of the biosynthetic methods used to make the maltosyl-isomaltooligosaccharide compositions is controlled at the optimum for dextransucrase enzyme(s), the resulting composition is not a product of nature. In nature, bacteria will in the course of metabolic processes, create organic acids. As this occurs, the pH will drop to 3.5-4.2. The ultimate pH in a natural product is thus significantly less than the optimum range of dextransucrase enzymes (e.g. pH 5.6, see FIG. 7) which will limit both the yield and the mass average molecular weight distribution of MIMOs so made. Hence a product made in nature will typically have a degree of polymerization (DP) range between 3 and 6, weighted heavily towards DP 3. In comparison, the DP of the compositions described herein can be higher. For example, most of the MIMO oligosaccharides in the compositions provided herein have a DP of 4 or more, or even a DP of 5 or more. An example of a MIMO composition prepared as described herein is shown in FIG. 39.

For example, at least 40%, or at least 50%, or at least 55%, or at least 57%, or at least 60%, or at least 62%, or at least 65% of the MIMOs in the compositions describe here have a DP of 5 or more.

Furthermore, the compositions produced as described herein are significantly free of organic acids, but those organic acids will be present in a natural fermented product. Also, under equivalent conditions in terms of the quantity of sucrose present, the natural product will contain significantly more mannitol (e.g., 33%/brix) than the composition described herein (typically 6-8%/brix).

DESCRIPTION OF THE FIGURES

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

maltose (S/M, w/w) ratio=2.00) with *L. citreum* NRRL B-742. Note that the MWD continues to increase (until about 15 hours) after the sucrose is exhausted (at about 10 hours). The rate of chain growth then takes place at a lower, but constant rate until the end of fermentation (55 hours) when a MWD of 642.5 Da was achieved.

Figure 21:
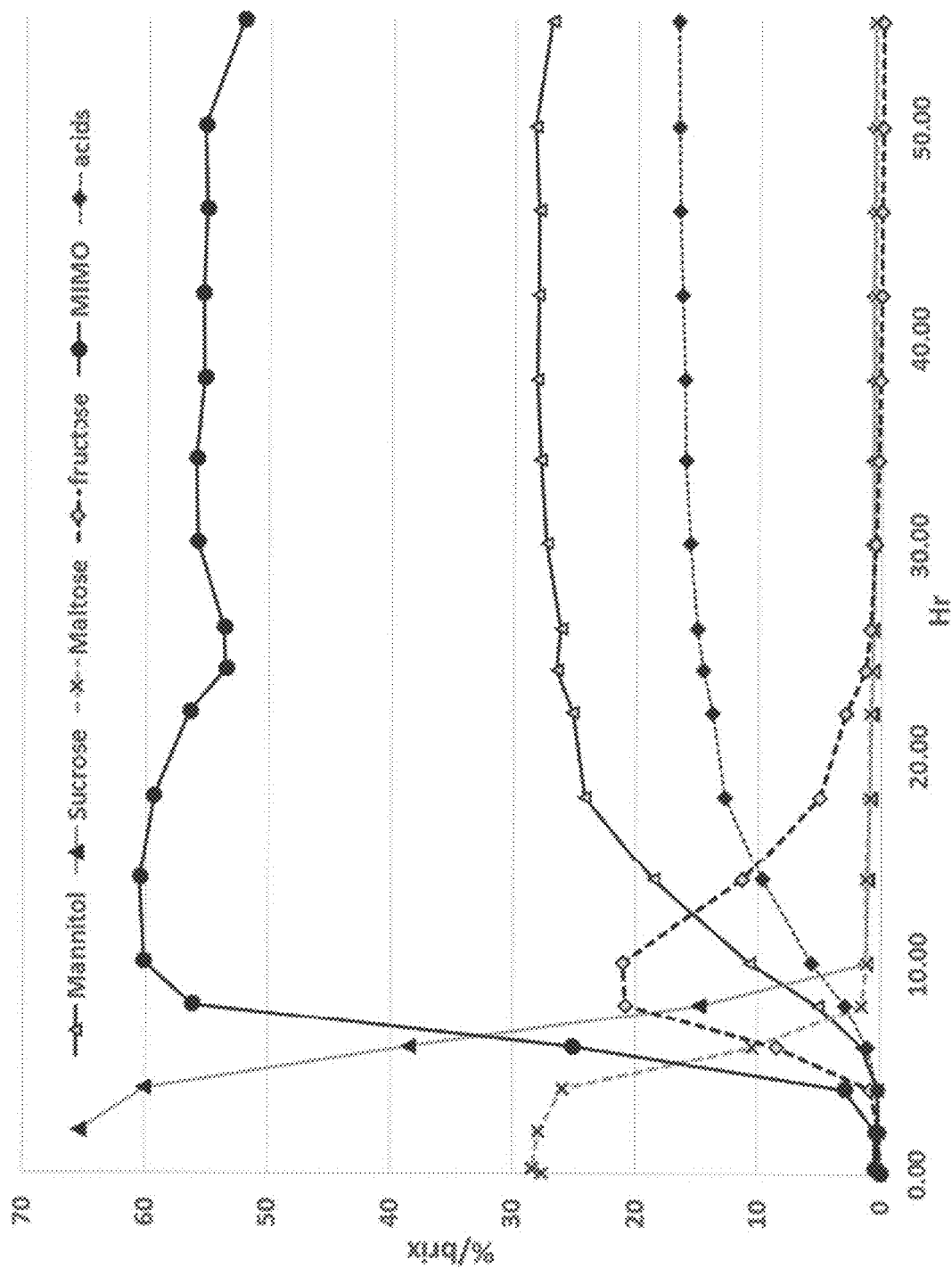

FIG. 21 graphically illustrates the generation of chemical species (as detected by HPAEC-PAD and HPLC-RID) throughout the course of a 10 L fermentation (sucrose/maltose=2.75) with *L. citreum* NRRL B-742.

Figure 22:
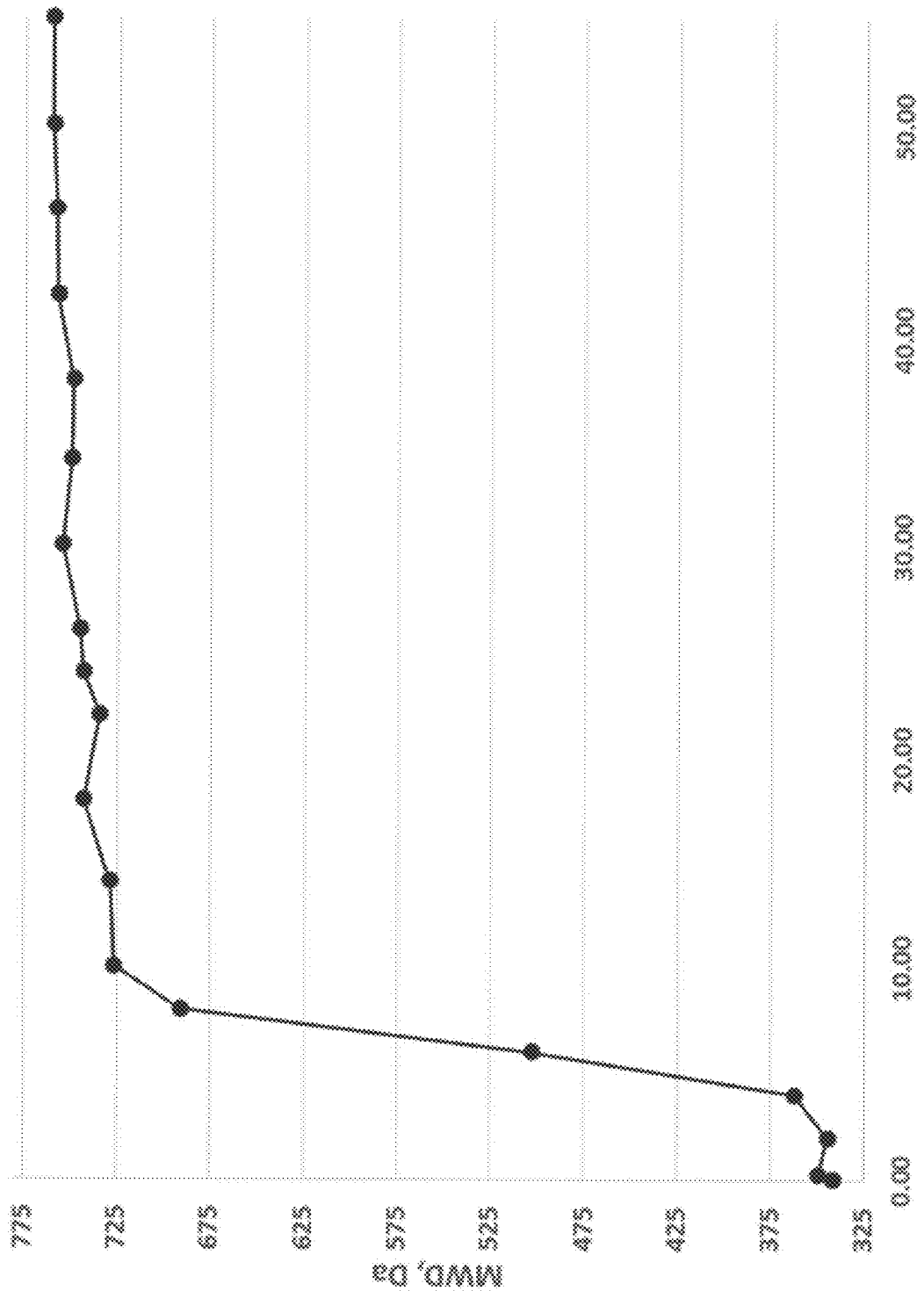

FIG. 22 graphically illustrates the evolution of the mass average molecular weight distribution (MWD) of MIMOs throughout the course of a 10 L fermentation (S/M=2.75) with *L. citreum* NRRL B-742. Note that the MWD continues to increase (until ~15 hours) after the sucrose is exhausted (~10 hours). The rate of chain growth then takes place at a lower, but constant rate until the end (55 hours) where a MWD of 760.7 Da was achieved.

Figure 23:
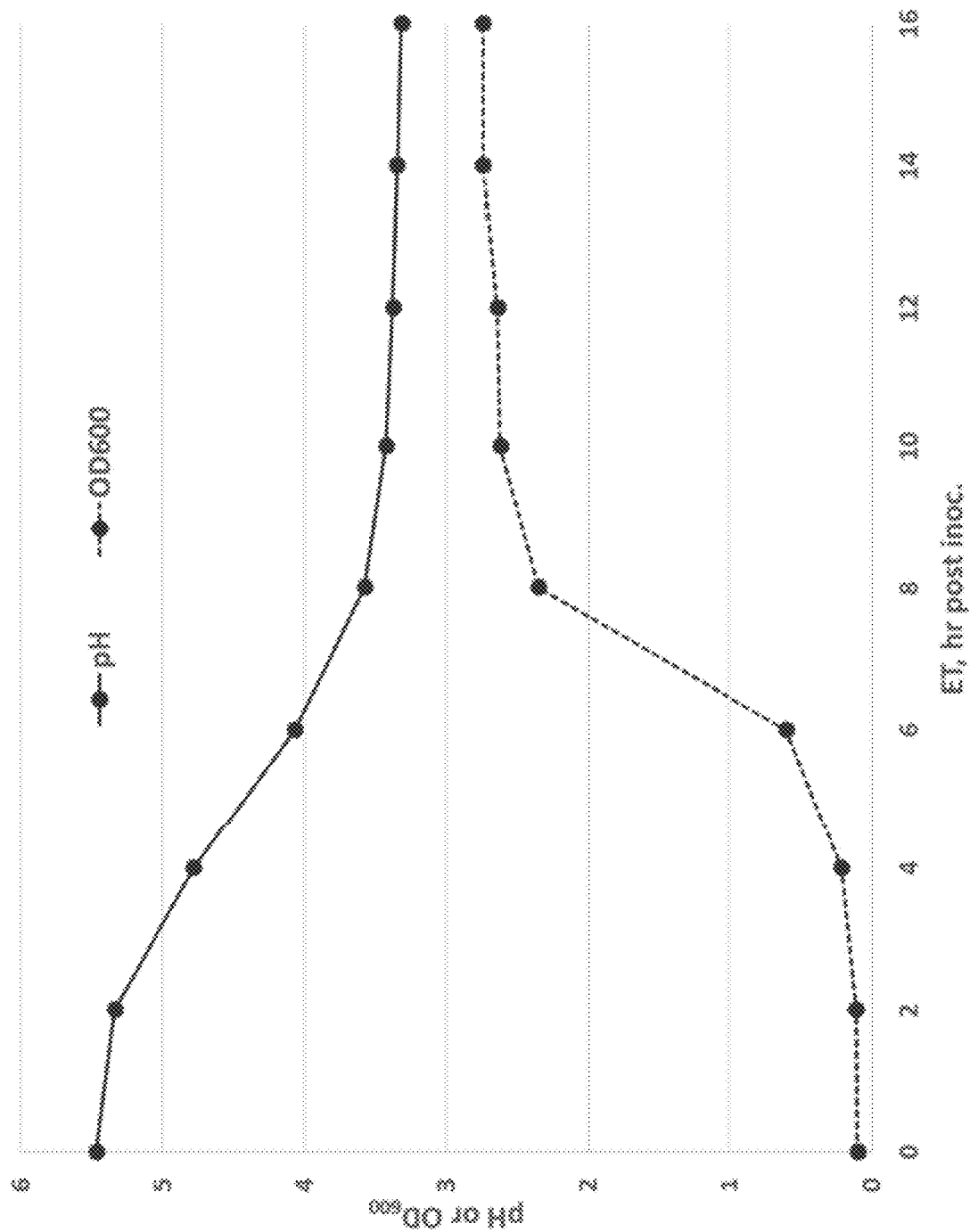

FIG. 23 sucrose:maltose (S/M, w/w) ratio behavior of pH and optical density ($OD_{600}$) through the log-growth phase of a 300 L seed fermentation (sucrose/maltose=2.00, lot #150622) with *L. citreum* NRRL B-742. Note that pH is not controlled, the culture reached late-log/stationary phase, and the final OD was approximately 2.8.

Figure 24:
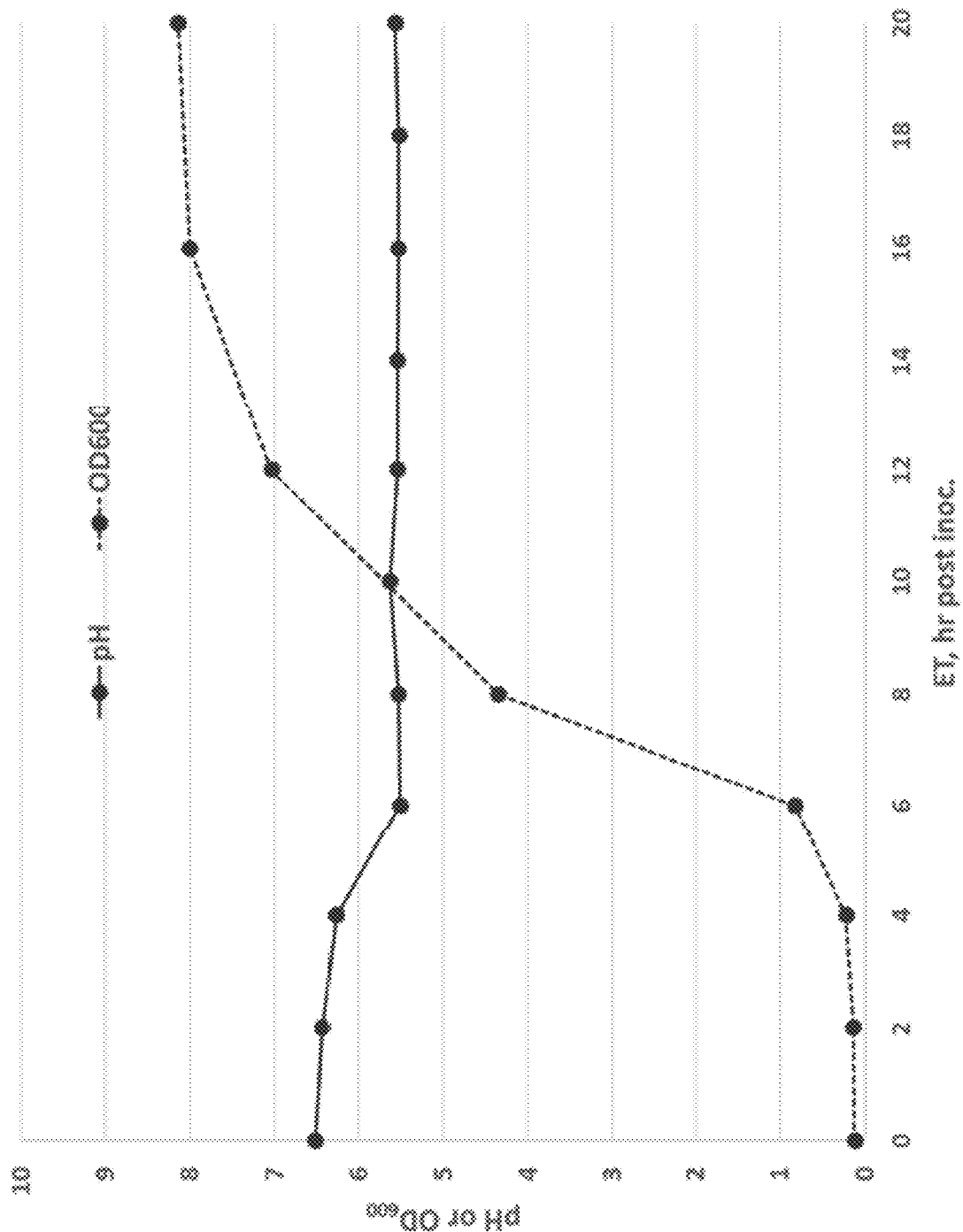

FIG. 24 graphically illustrates the behavior of pH and OD through the log-growth phase of a 3000 L fermentation (sucrose/maltose=2.75, lot #150622) with *L. citreum* NRRL B-742. Note that pH was controlled to maintain 5.50 and that the ultimate $OD_{600}$ was about 10.2.

Figure 25:
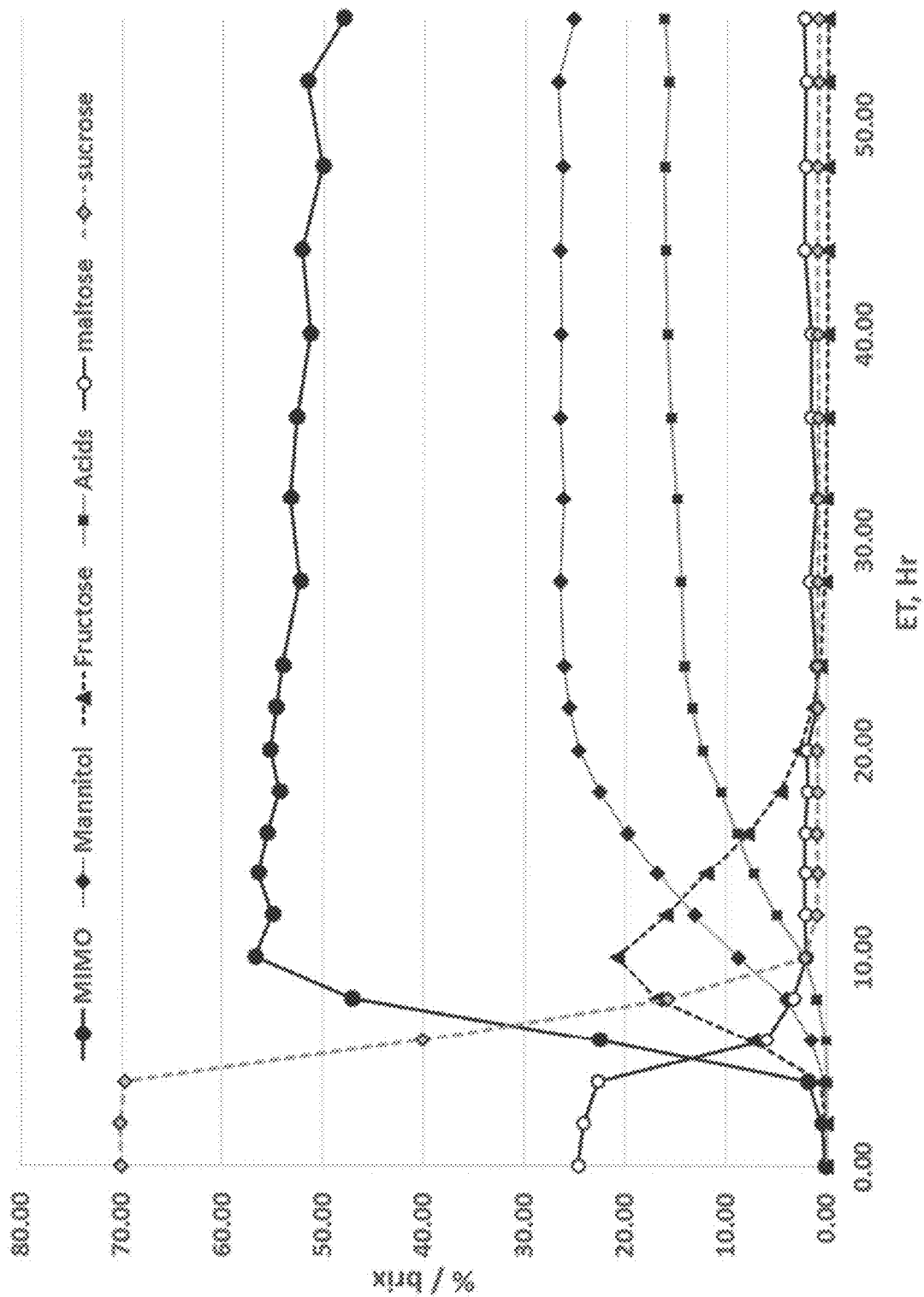

FIG. 25 graphically illustrates the generation of chemical species (as detected by HPAEC-PAD and HPLC-RID) throughout the course of a 3000 L fermentation (sucrose/maltose=2.75, lot #150622) with *L. citreum* NRRL B-742.

Figure 26:
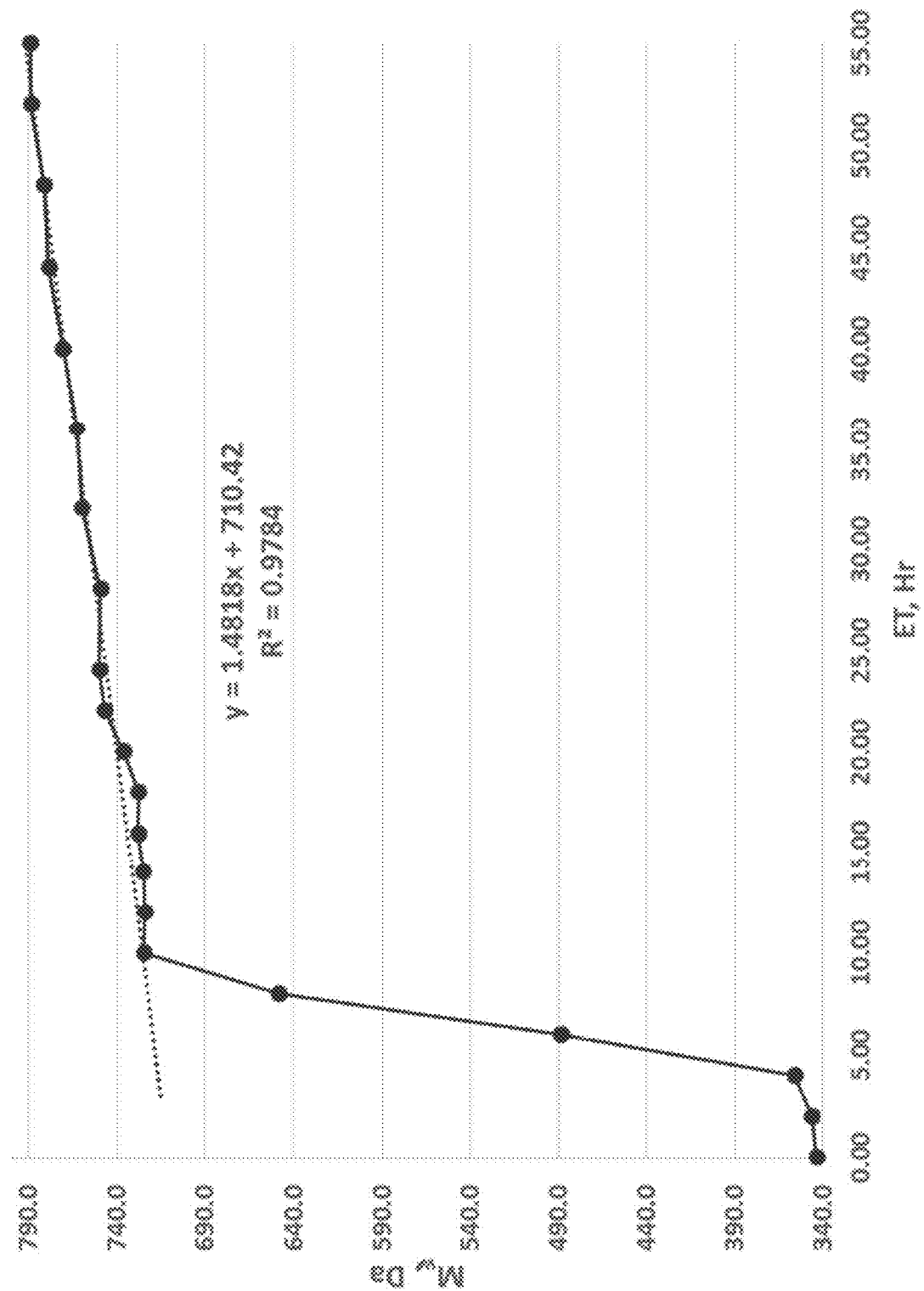

FIG. 26 graphically illustrates the evolution of the mass average molecular weight distribution (MWD) of MIMOs throughout the course of a 3000 L fermentation (sucrose/maltose=2.75, lot #150622) with *L. citreum* NRRL B-742. Note that the mass average molecular weight distribution continues to increase (until about 15 hours) after the sucrose is exhausted (at about 10 hours). The rate of chain growth then takes place at a lower, but constant rate until the end (55 hours) where a mass average molecular weight distribution of 789.5 Da was achieved.

Figure 27:
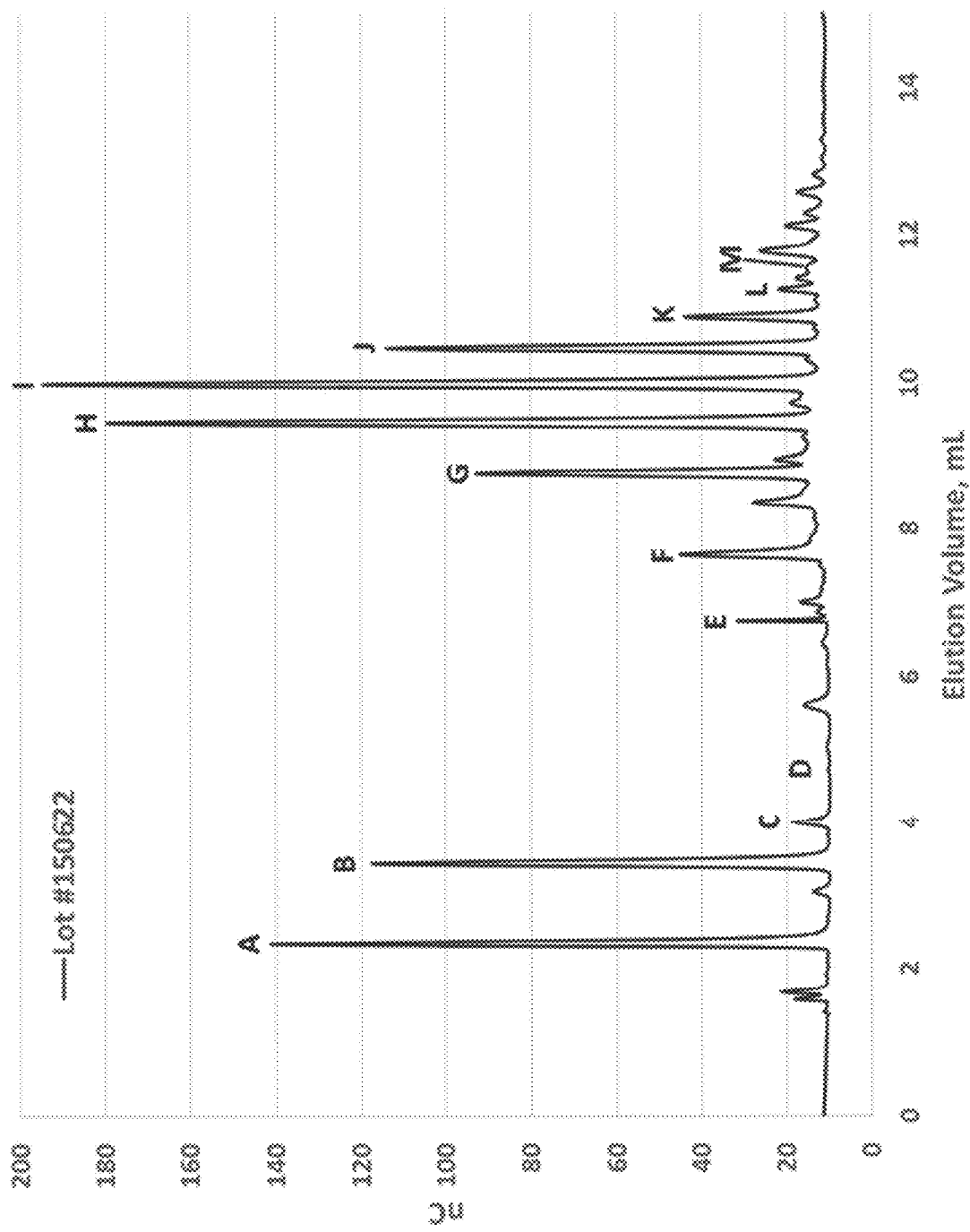

FIG. 27 shows a HPAEC-PAD chromatogram of product lot #150622 wherein the components are identified as A: D-mannitol; B: L-arabinose (internal standard); C: D-glucose; D: D-fructose; E: sucrose; F: maltose; and where G-M correspond to MIMO DP 3-9.

Figure 28:
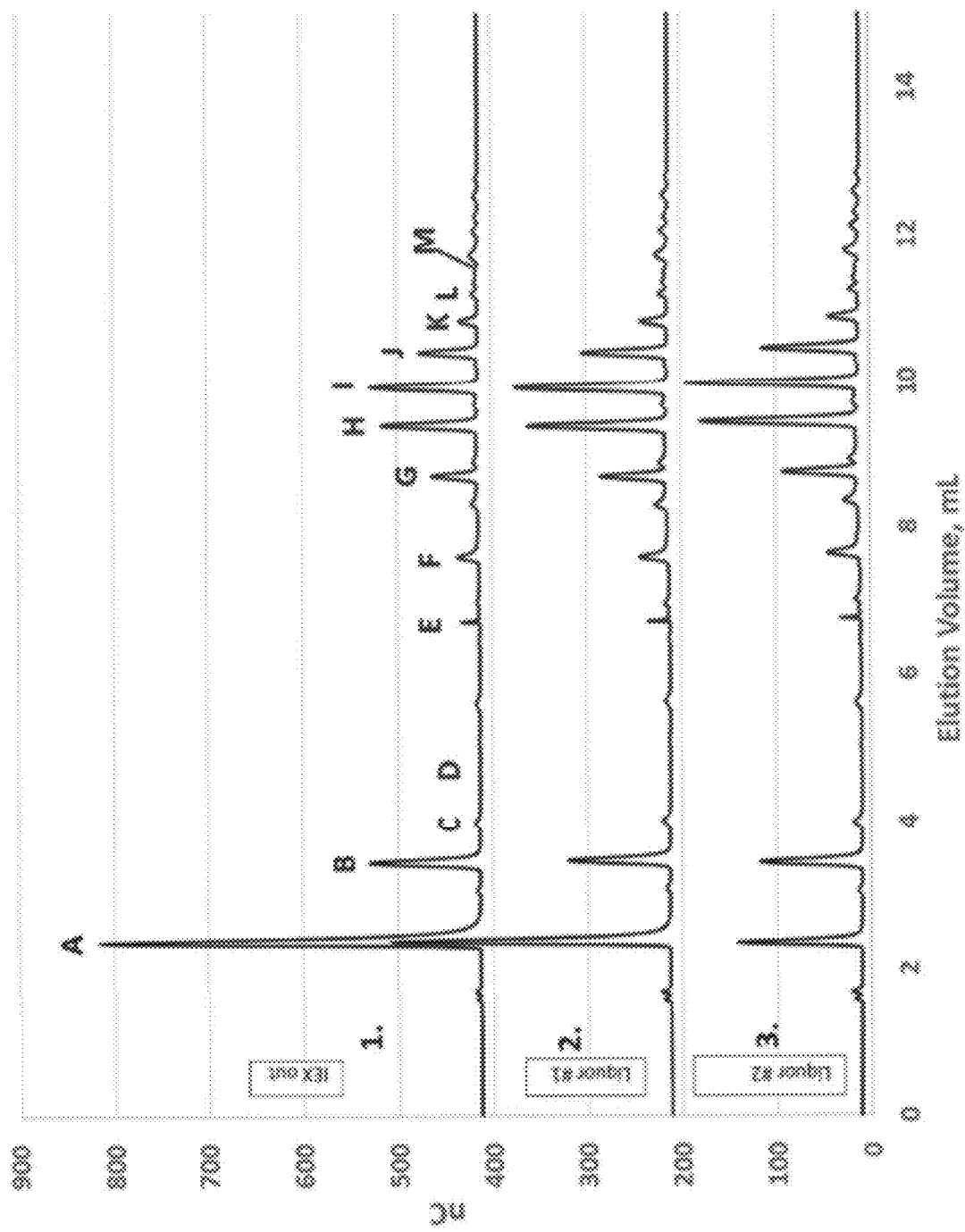

FIG. 28 shows HPAEC-PAD chromatograms during removal of mannitol from mother liquor 1, and 2, 3 corresponding to compound crystallization stages, 1 and 2, respectively. The components are identified as A: D-mannitol; B: L-arabinose (internal standard); C: D-glucose; D: D-fructose; E: sucrose; F: maltose; and G-M corresponding to MIMO DP 3-9. Note that mannitol is reduced and that the MIMO purity increased thereby.

Figure 29:
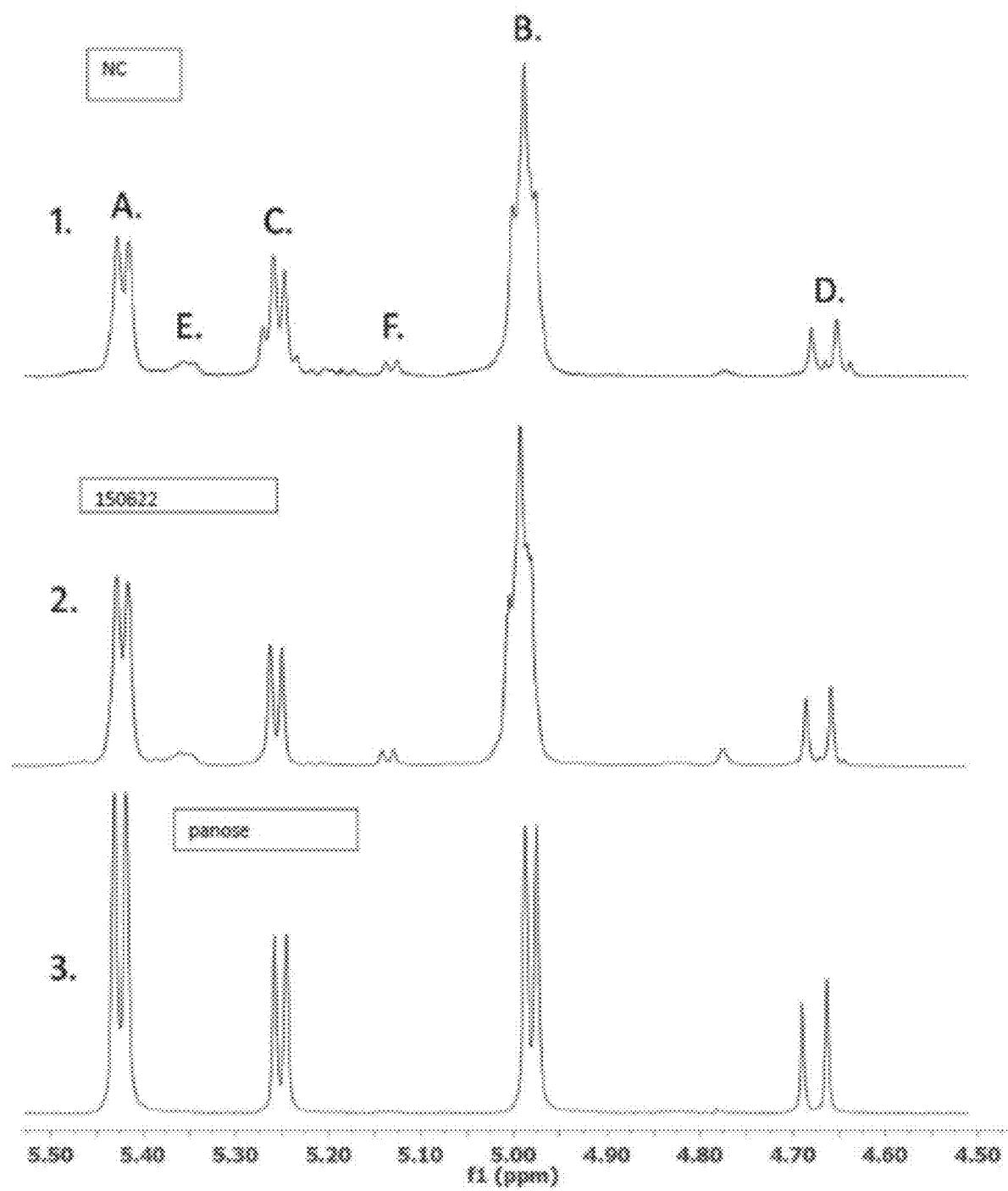

FIG. 29 shows an overlay of 1D 300 MHz $^1$H NMR (water suppressed in $D_2O$) spectra of the anomeric regions of 1 and 2, NC and lot #150622 products, respectively and, 3, D-panose (6 reference) wherein signal A correspond to α-(1,4) anomeric protons; signal B corresponds to α-(1,6) anomeric protons; signals C and D correspond to the α and β anomeric protons, respectively, at the reducing end; and signals E and F correspond to regions corresponding to α-(1,3) and α-(1,2) anomeric protons, respectively. Note the minimal or absent second doublet in lot #150622; this is likely due to the acidification step, which avoids possible alkali catalyzed epimerization of C2.

Figure 30:
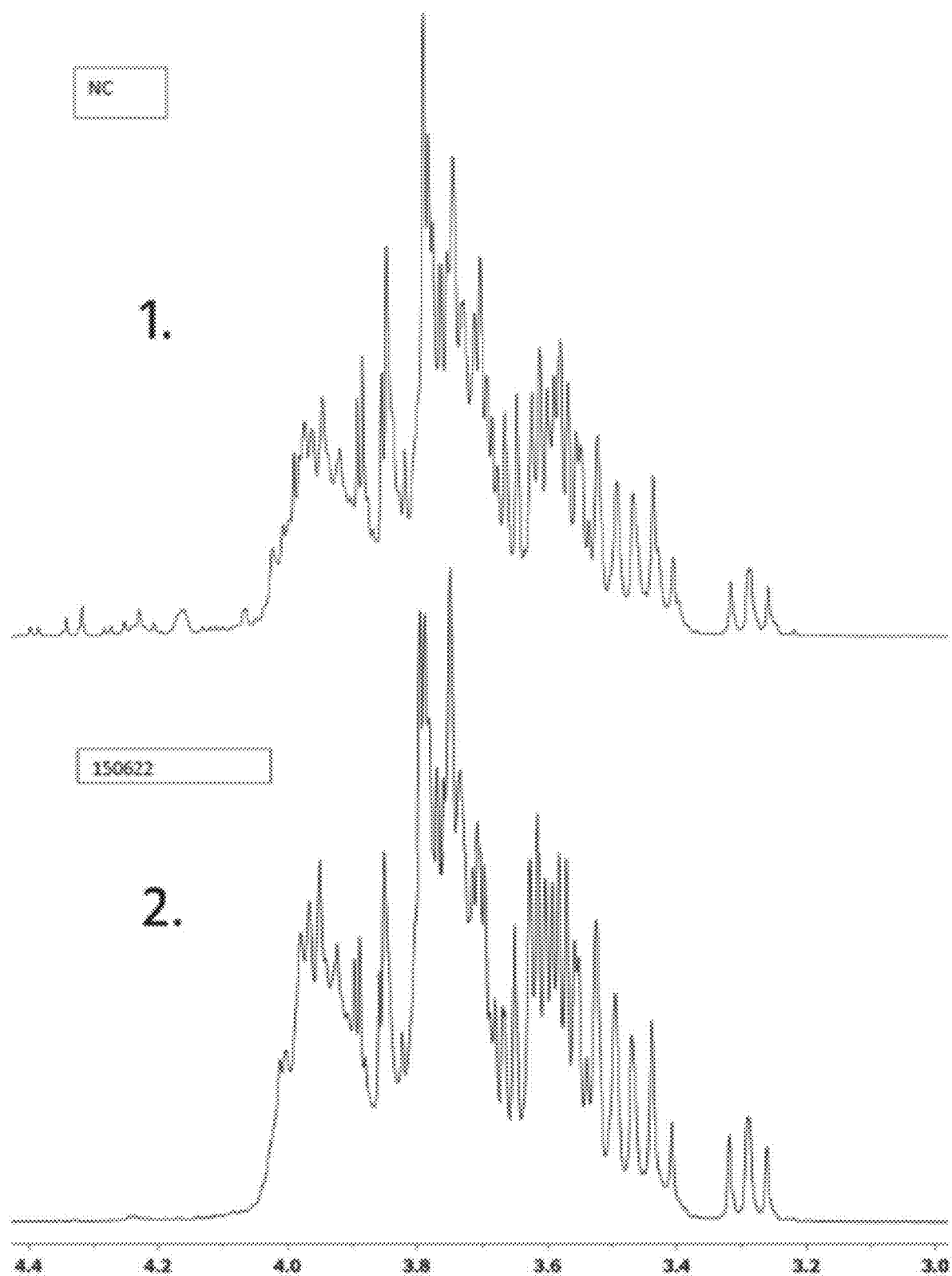

FIG. 30 shows an overlay of 1D 300 MHz $^1$H NMR (water suppressed in $D_2O$) spectra of the non-anomeric regions of 1) NC and, 2) lot #150622 products.

Figure 31:
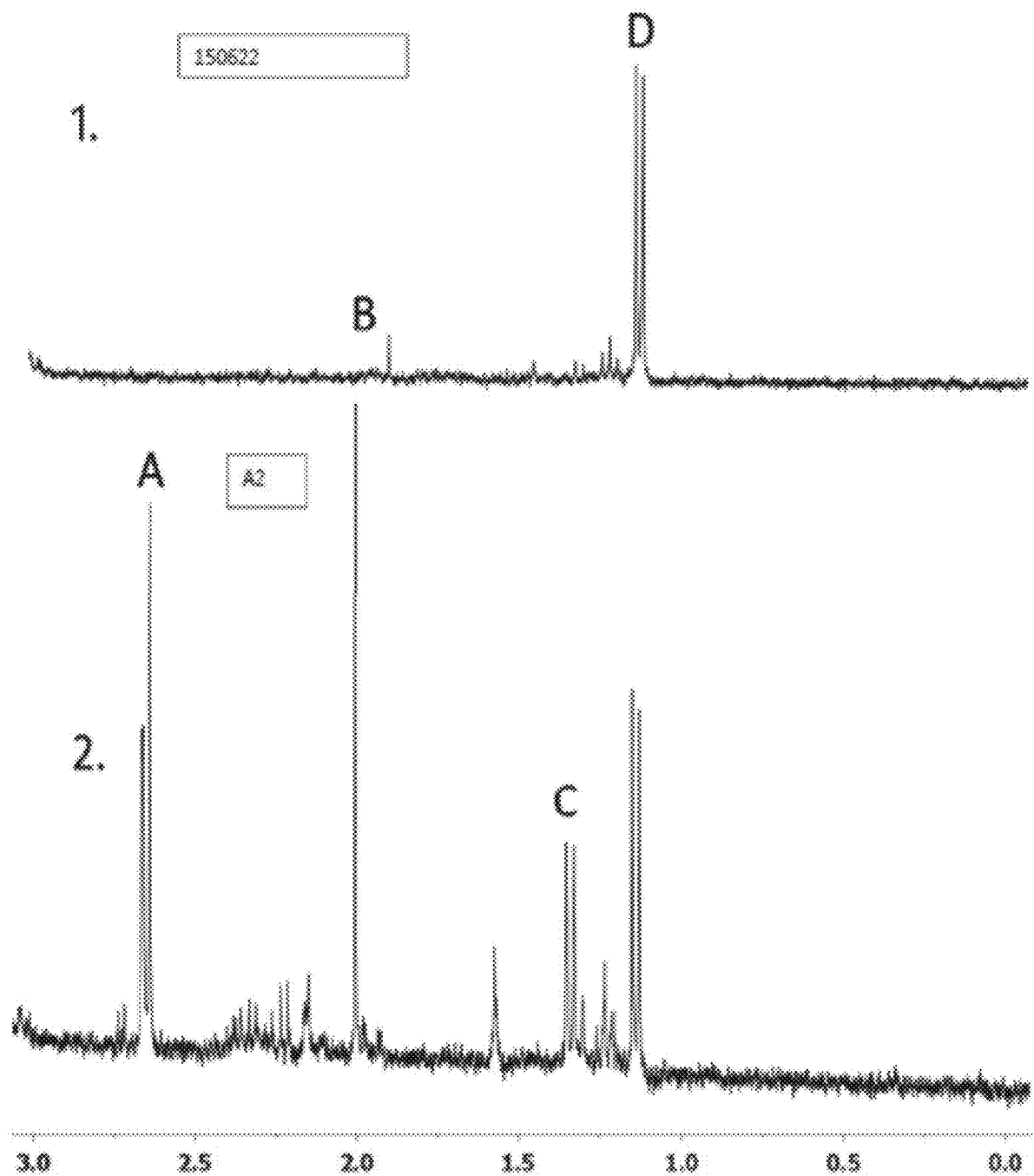

FIG. 31 shows an overlay of 1D 300 MHz $^1$H NMR (water suppressed in $D_2O$) spectra of the alkyl regions of (1) lot #150622; and (2) A2 products. Signal A is an unknown; signal B corresponds to acetyl protons (the difference is due to pH, A2=4.81, lot #150622=6.08); signal C corresponds to lactate C3 methyl protons; and signal D is unassigned. Note, the amount of acetate/lactate in both 1 and 2 (A2) were below the minimum detectable limit (MDL) of HPLC-RID.

Figure 32:
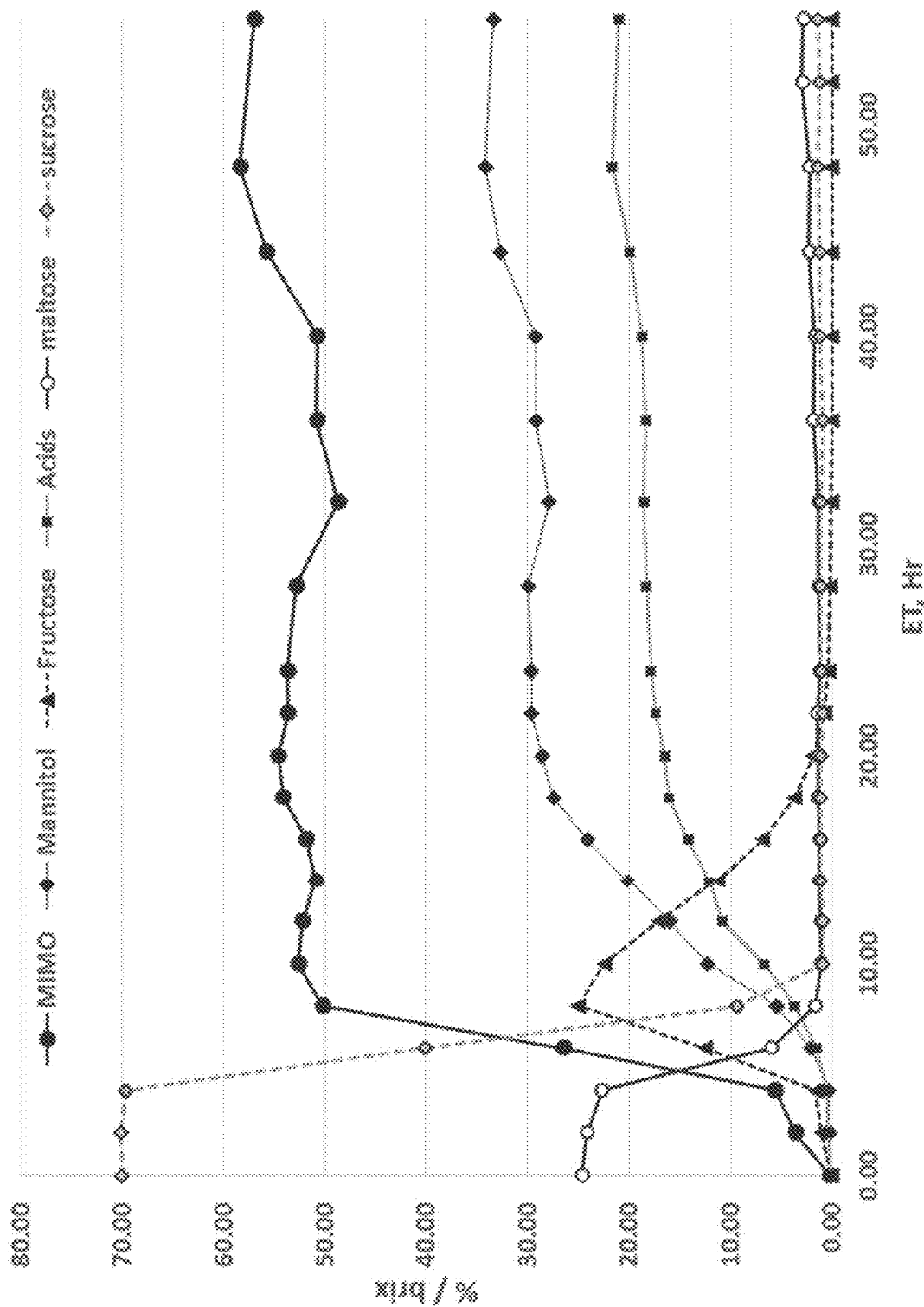

FIG. 32 shows the amounts of chemical species as detected by HPAEC-PAD and HPLC-RID throughout the time course of a 3000 L fermentation (S/M=2.75, lot #151105) using *L. citreum* NRRL B-742.

Figure 33:
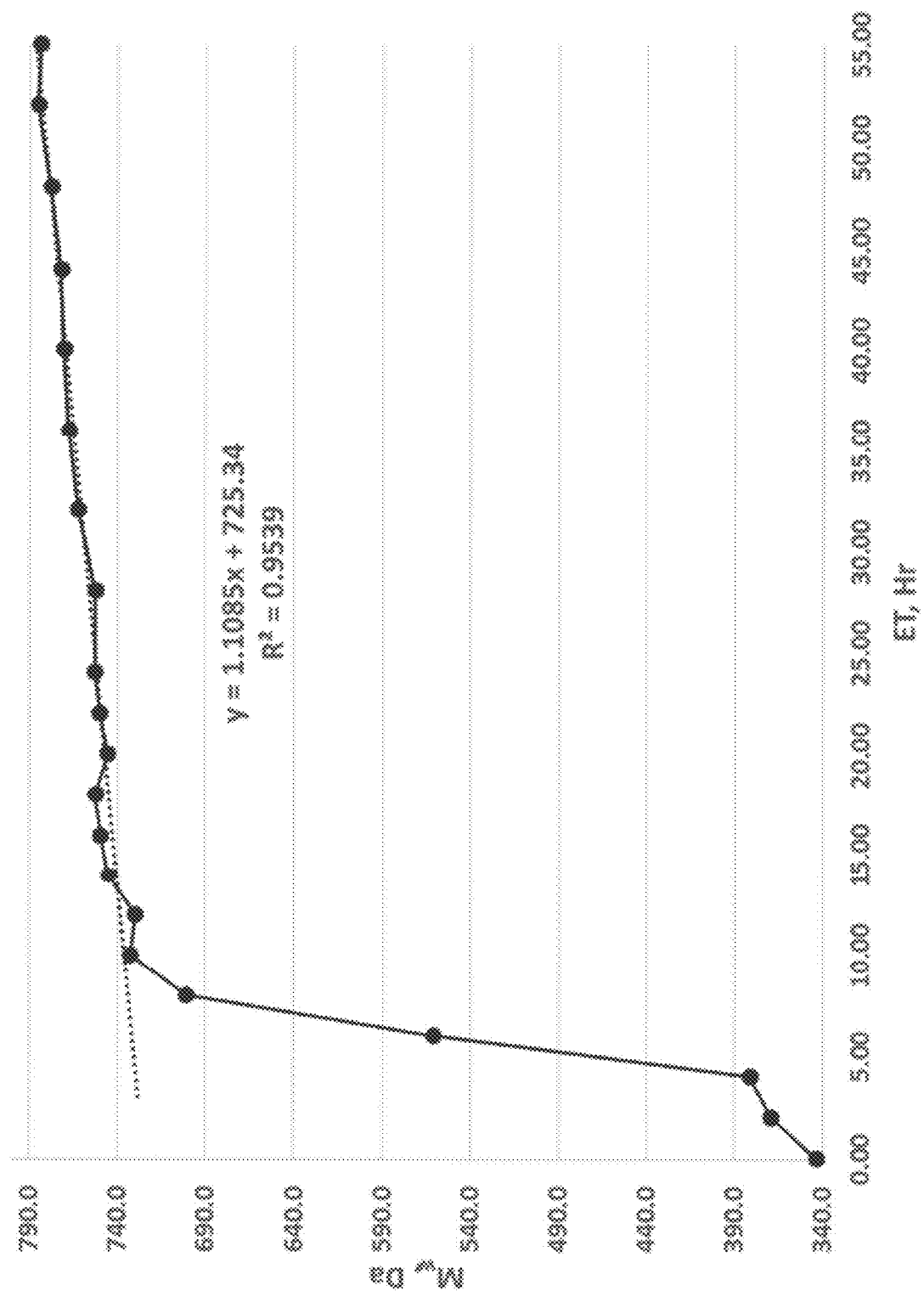

FIG. 33 illustrates the evolution of the mass average molecular weight distribution of MIMOs throughout the course of a 3000 L fermentation (S/M=2.75, lot #151105) with *L. citreum* NRRL B-742. Note that the MWD continues to increase (until about 15 hours) after the sucrose is exhausted (at about 10 hours). The rate of chain growth then takes place at a lower, but constant rate until the end of fermentation (55 hours) when the molecular weight of about 776.5 Da was achieved.

Figure 34:
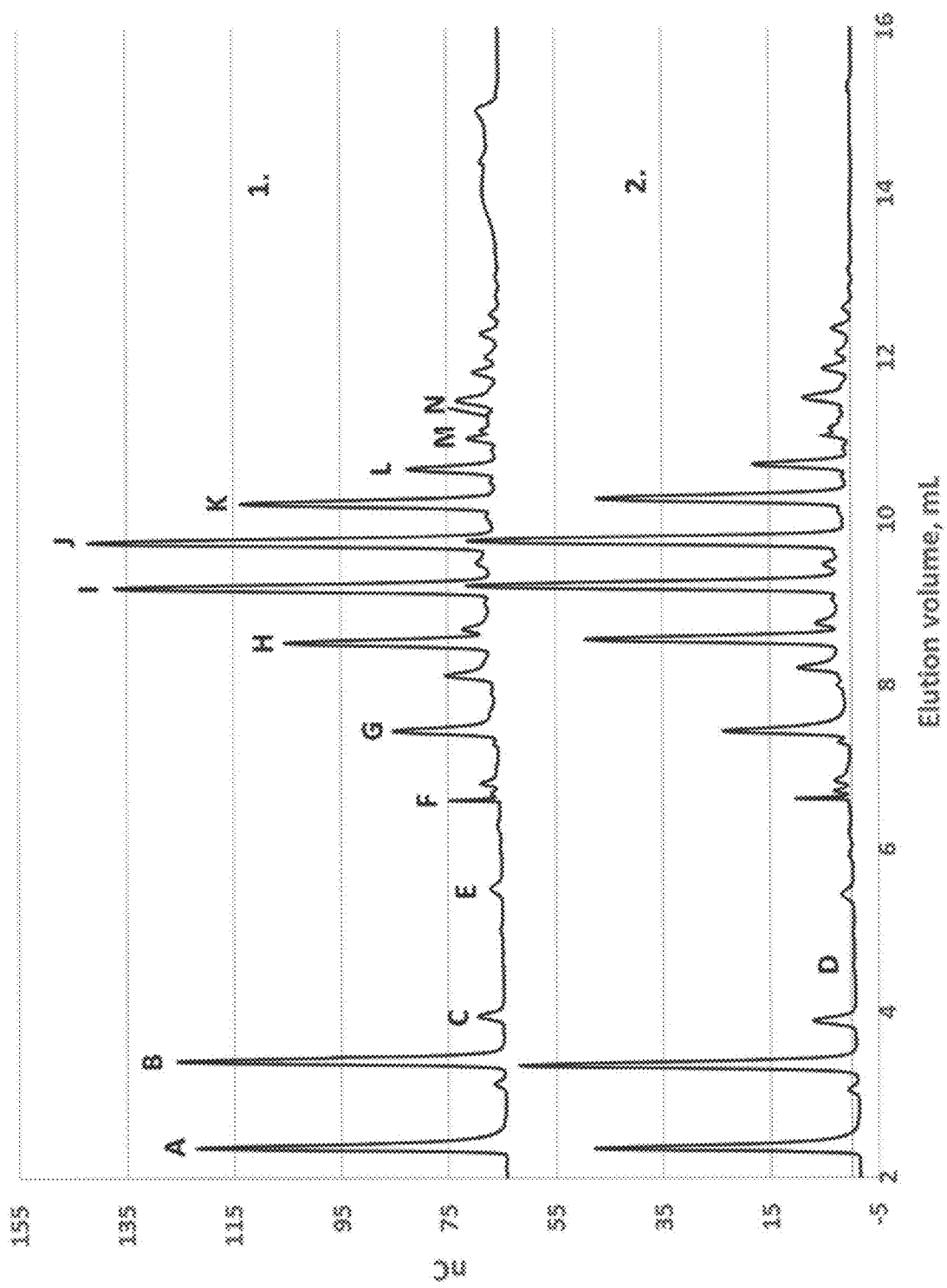

FIG. 34 shows HPAEC-PAD chromatograms of (1) product lot #150622, and, (2) Product lot #151105, wherein the components are identified as A: D-mannitol; B: L-arabinose (internal standard); C: D-glucose; D: D-fructose; E: D-leucrose, F: sucrose; G: maltose; and where H—N correspond to MIMO DP 3-9, respectively. For example, note the high proportion of MIMO DP5 (J), DP6 (K), and DP7 (L).

Figure 35:
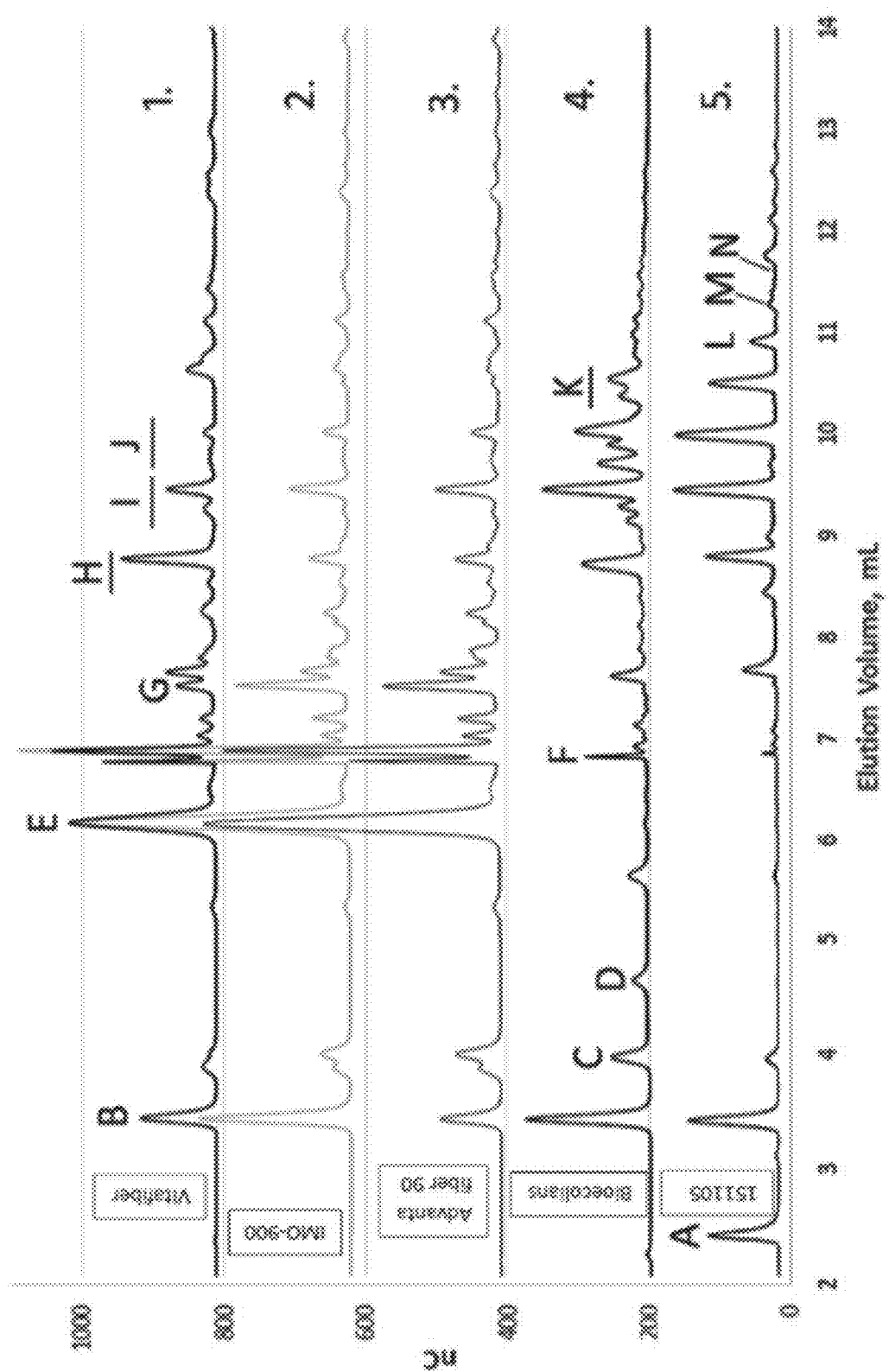

FIG. 35 shows an overlay of HPAEC-PAD chromatograms comparing the (5) ISOThrive product MIMO lot #150622 with commercial MIMO-based products, (1) IMO powder (Bioneutra VitaFiber); (2) IMO powder (Baolingbao IMO-900); (3) IMO powder (TopHealth AdvantaFiber 90); and (4) IMO powder (Solabia Bioecolians). The components of these compositions were identified as A: D-mannitol; B: L-arabinose (internal standard); C: D-glucose; D: D-fructose; E: isomaltose; F: sucrose; G: maltose; and H—N corresponding to MIMO DP 3-9, respectively. Note the presence of 30-45% of isomaltose in IMOs 1, 2, and 3. The MWDs were cut off sharply at DP 5 for IMO 1. There was an almost undetectable trace of MIMO DP 6 in IMOs 2 and 3. Note also, the presence of extensive branching in IMO 4 that is not observed in the composition generated as described herein.

Figure 36:
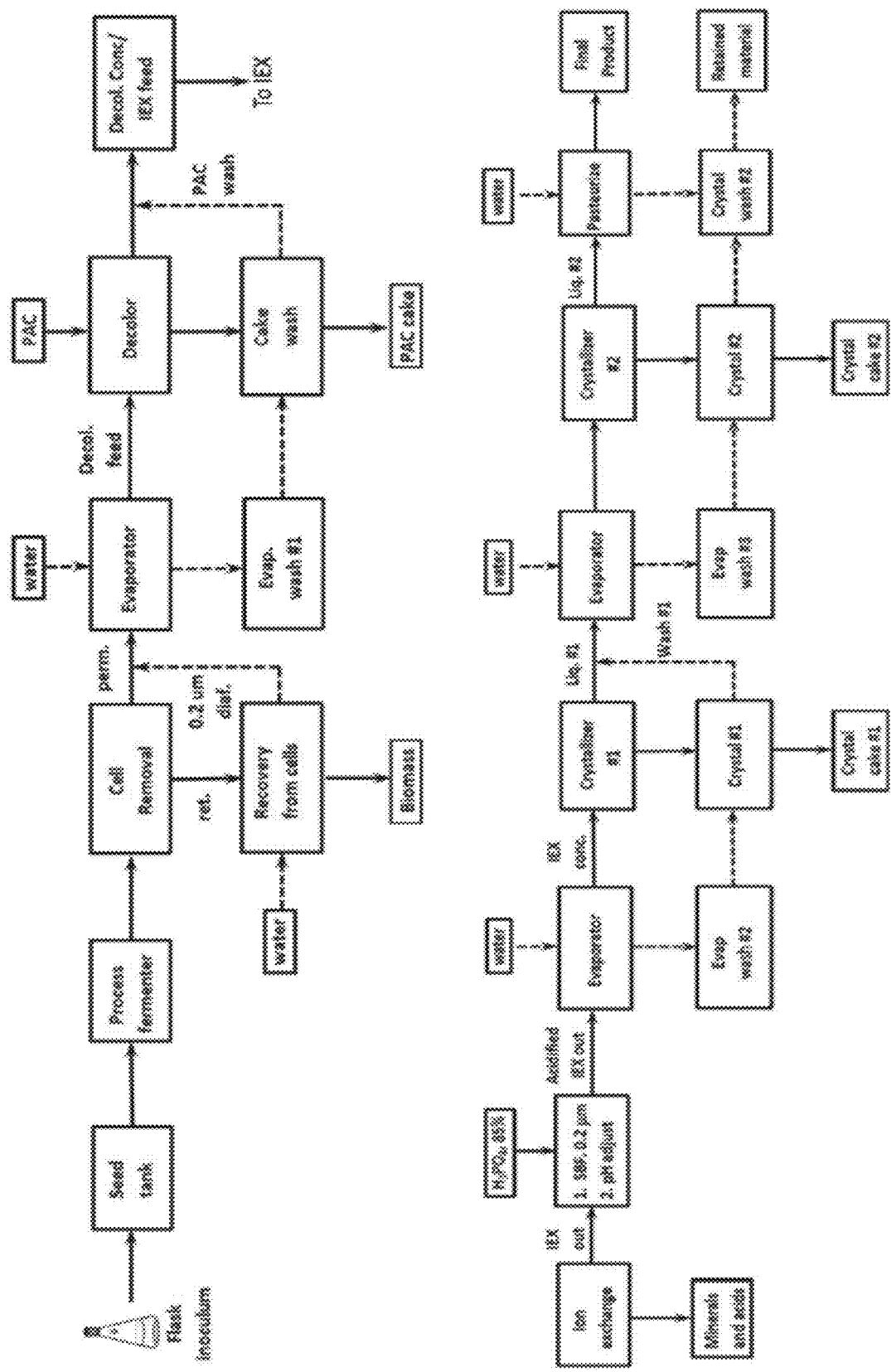

FIG. 36 is a schematic diagram of a method of manufacturing MIMO.

Figure 37B:
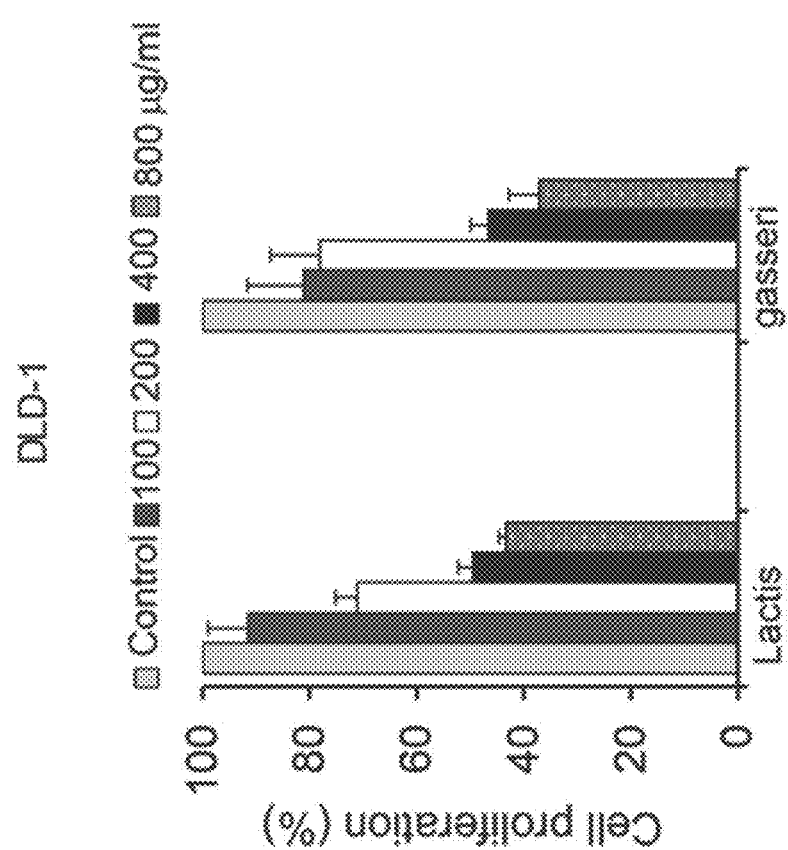
Figure 37A:
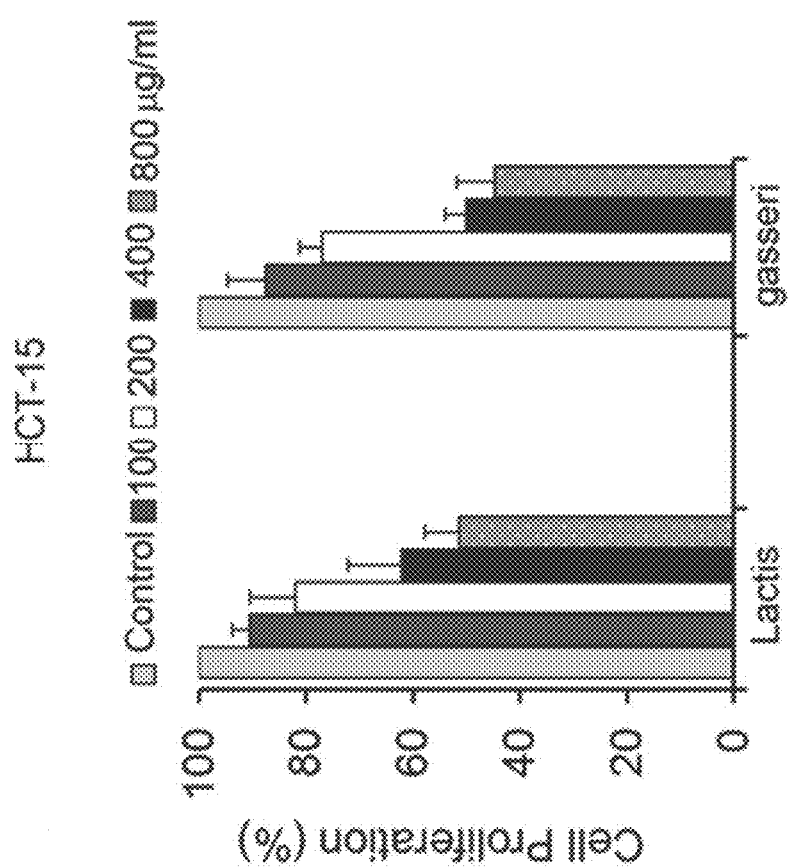

FIG. 37A-37B graphically illustrate inhibition of colon cancer cell growth by media obtained from culture of *Lactococcus lactis* and *Lactobacillus gasseri* using a CyQUANT NF cell proliferation assay. Dosing was 0 (control), 100, 200, 400, and 800 µg/mL equivalent protein (BCA assay) in both cases. FIG. 37A shows that broth from *Lactococcus lactis* and *Lactobacillus gasseri* cultures reduced HCT-15 colon cancer cell proliferation in a dose-dependent manner relative to control culture media. Proliferation of cells was reduced by 60% at the maximum dose tested indicating a dose of appx. 1.3µ g/g equivalent nisin A. Broth produced using *L. gasseri* demonstrated a clear threshold of effect equivalent to appx. 0.65 µg/g nisin A. FIG. 37B shows that broth from *Lactococcus lactis* and *Lactobacillus gasseri* cultures reduced DLD-1 colon cancer cell proliferation in a dose-dependent manner relative to control culture media. Antiproliferative activity was similar to that observed vs. HCT-15 cells. Again, broth produced with *Lactobacillus gasseri* demonstrated a dose threshold of approximately half of the equivalent dose of Nisin A. The left-most bar in each cluster shows cancer cell growth with no intervention. The second bar (from the left) shows cancer cell growth in the presence of 100 µg/ml of intervention broth indicated as either from *Lactococcus lactis* or *Lactobacillus gasseri*. The third bar (from the left) shows cancer cell growth in the presence of 200 µg/ml control broth. The fourth bar (from the left) shows cancer cell growth in the presence of 400 µg/ml control broth. The fifth bar (from the left or the rightmost bar) shows cancer cell growth in the presence of 800 µg/ml control broth.

Figure 38:
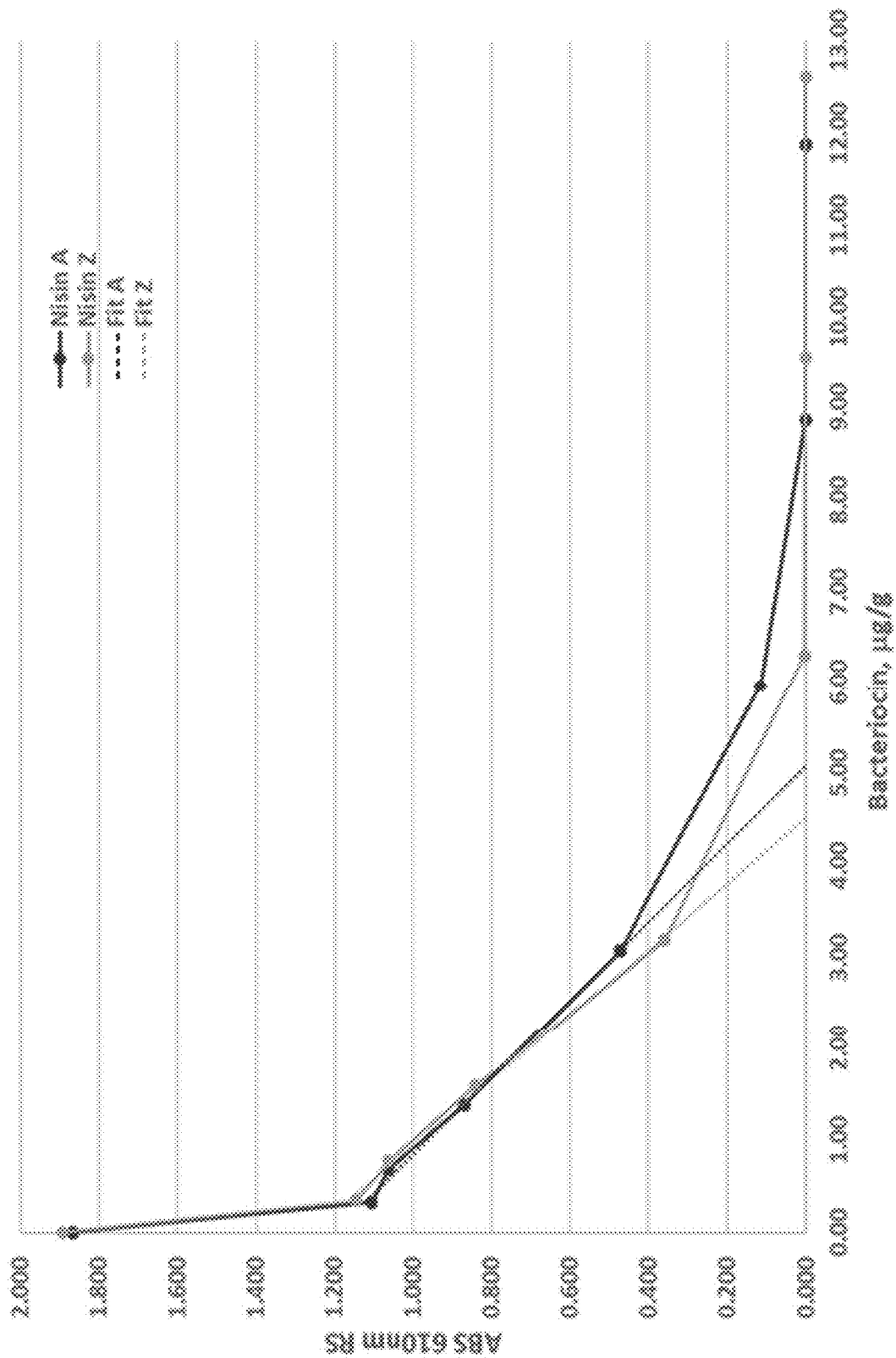

FIG. 38 graphically illustrates growth of *Weissella viridescens* in the presence of known amounts of nisin A (black lines) and nisin Z (gray lines). The dashed lines illustrate regression analysis to provide an approximation of the minimum inhibiting concentrations of nisin A (black dashed line) and nisin Z (gray dashed line) for inhibiting *Weissella viridescens* growth.

FIG. 39 shows an example of a MIMO composition prepared as described herein (see, e.g., Example 7).

FIG. 40 shows an example of a MIMO composition prepared as described in Example 3.

FIG. 41 shows an example of a MIMO composition prepared as described in Example 4.

FIG. 42 shows an example of a MIMO composition prepared as described in Example 6.

DETAILED DESCRIPTION

Compositions described herein contain maltose-containing oligosaccharides, referred to as maltosyl-isomaltooligosaccharides (MIMOs) that are a preferred energy source of various beneficial intestinal bacteria (e.g., *Lactobacillus* and/or *Bifidobacterium* spp.) over other types of oligosaccharide prebiotics. The compositions described herein can foster the growth and activities of such beneficial intestinal bacteria. Because certain types of beneficial bacteria (e.g., *L. lactis* strains) can produce various types of bacteriocins (e.g., nisins) that can act as anti-cancer agents and/or as anti-microbial agents, the compositions described herein can help to reduce the symptoms or the incidence of some type of diseases and conditions. For example, early studies indicate that the compositions described herein can reduce or eliminate symptoms in 81% of users who self-identified as having acid reflux symptoms once a week or more.

The maltosyl-isomaltooligosaccharides in the compositions described herein include glucose residues linked mostly by α-(1,6) linkages, and one or two maltose resides (e.g., at the reducing end) that can be linked to a glucose unit by an α-(1,4) linkage. The majority of the linkages between the glucose units in the maltosyl-isomaltooligosaccharides in the compositions are α-(1,6) linkages, although small numbers of α-(1,2), α-(1,3), and α-(1,4) linkages can be present. The maltosyl-isomaltooligosaccharides are therefore typically linear oligosaccharides, with few branch points. The maltosyl-isomaltooligosaccharides terminate in a maltose unit. The mass average molecular weight distribution (MWD) of the MIMOs in the compositions described herein can vary depending upon the degree of polymerization (DP). For example, the maltosyl-isomaltooligosaccharides compositions can contain a mass average molecular weight distribution of about 520 to 1200 daltons, or of about 640 to 1000 daltons. In some cases, the maltosyl-isomaltooligosaccharides compositions contain a mass average molecular weight distribution of about 730 to 900 daltons.

An example of an MIMO with a single maltosyl linkage [—O-α-(1,4)-] at the reducing end, and a DP of 5, can have the following chemical structure:

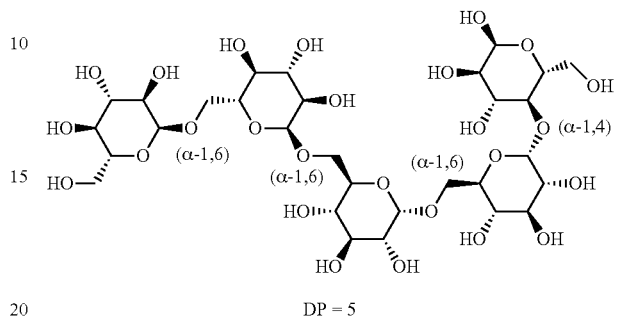

DP = 5

The MIMOs in the compositions described herein can have a number of glucose units. For example, the MIMOs in the compositions described herein can have from about 2 to about 18 glucose units, or about 2 to about 17 glucose units, or about 3 to about 16 glucose units, or about 3 to about 15 glucose units, or about 3 to about 14 glucose units, or about 3 to about 13 glucose units, or about 3 to about 12 glucose units. In general, the maltose-containing oligosaccharides have no more than about 17 glucose units, or no more than about 16 glucose units, or no more than about 15 glucose units, or no more than about 14 glucose units, or no more than about 13 glucose units, or no more than about 12 glucose units, or no more than about 11 glucose units, or no more than about 10 glucose units, for example, as detected by HPAEC-PAD or HPLC-RID.

As indicated, the MIMOs in the compositions described herein can have small numbers of α-(1,2), α-(1,3), and α-(1,4) glucosyl linkages. Hence, the MIMOs in the compositions described herein can have small numbers of branch points. For example, the MIMOs in the compositions described herein can have 0-4 branch points, or 0-3 branch points, or 0-2 branch points, or 0-1 branch points.

Oligosaccharides and Methods of Making them

Oligosaccharides are an extremely diverse class of molecules, consisting of short chains of monosaccharide molecules composed of less than eighteen, less than sixteen, less than fourteen, less than twelve, or less than ten monosaccharide units. The monosaccharides observed in prebiotic oligosaccharides are typically galactose (galactooligosaccharides, GOS), glucose (glucooligosaccharides, GlcOS), xylose (xylooligosaccharides, XOS), and fructose (fructooligosaccharides, FOS). GlcOS are a class of carbohydrate oligomers that include isomaltooligosaccharides (IMO). IMOs are glucosyl saccharides with a core structure based on an α-(1→6) linked backbone that can include α-(1→4), α-(1→3) (nigerooligosaccharides) and\or α-(1→2) (kojioligosaccharides) linked branches (Yun, J. et al., Biotechnol. Lett., 1994, 16:1145-1150). These glucosidic linkages are typically found in commercial IMO syrups (Goffin, D. et al., Crit. Rev. Food Sci. Nutr. 51:394-409 (2011)).

Oligosaccharides can be sourced from plants (FOS from agave, yacon; inulin/FOS from chicory), obtained from hydrolyzed starch or exopolysaccharide (e.g. dextran, GlcOS, IMO, MIMO), made via transglycosylaton via immobilized enzymes, or generated via fermentation products conforming to the species-specific exopolysaccharide (EPS) in the presence of an acceptor molecule (MIMO). Isomaltooligosaccharides, or IMOs, are oligodextrans resulting from the homopolymerization of glucose, and are thus a distinct sub-class of glucooligosaccharides (GlcOS).

However, the types of MIMOs provided herein are not made by plants. Hence, the MIMOs described herein are not found in foods that are typically ingested by humans. Instead, the MIMOs described herein are made under controlled manufacturing conditions by specific strains of bacteria that express unique types of enzymes needed to provide the structural attributes of the subject MIMOs.

Dextran can, for example, be made by certain enzymes. For example, most *Leuconostoc* species express a glucosyl-transferase enzyme (or cohort of enzyme isoforms) known as dextransucrase. This enzyme, in the presence of sucrose performs two functions. First, the enzyme cleaves sucrose and expels fructose. Then, the enzyme cleaves another sucrose molecule and the glucose unit from such cleavage is glycosidically linked to the first glucose. This goes on until very long (>10 kDa up to about 40 MDa) α-(1,6) polyglucan chains, known as "dextran" result.

If dextran is treated with a dextranase enzyme, an α-(1,6) glucosidase, IMO, can result that will have the branched linkages intrinsic to the dextransucrase produced by the parent organism including, for example, a degree of polymerization (DP) or 2-10, and 15% α-(1,3) linkages (when using *L. mesenteroides* NRRL B-1426; Kothari and Goyal, 2015).

In some cases, controlled treatment of dextran from *L. mesenteroides* B-512F would yield a distribution of linear (unbranched) α-(1,6) molecules (oligodextrans) and similar treatment by *L. citreum* B-1299 would yield dextran with a distribution of α-(1,2) branched α-(1,6) molecules (branched oligodextrans). It would be possible to mix dextran types prior to hydrolysis, as well.

Dextransucrase, however, will, in the presence of sucrose and an acceptor molecule (such as maltose), create MIMOs. The typical route to dextran synthesis via dextransucrase is then "interrupted" by the acceptor molecule causing the growth of the chain to terminate prematurely. In effect, the presence of an acceptor such as maltose limits the molecular weight of the oligosaccharide. When this occurs, specifically with maltose, short glucose chains terminated with maltose will result. These molecules are referred to as panose-type maltosyl-isomaltooligosaccharides.

Treatment of starch with enzymes, such as amylase/neopullalanase, either together or sequentially, was noted by Kuriki, et al. (1993) to yield panose (MIMO DP 3), isopanose, and maltooligosaccharides in the range of 3 to about 5 (weighted heavily on DP 3), can yield a distribution of resistant branched molecules (dextrin). Sakano, et al. (1978) noted that treatment of pullulan with isopullanase have also been found to produce panose (MIMO DP 3).

As noted, dextransucrase is a glucosyl transferase that catalyzes the transfer of a glucose residue from sucrose to a growing polyglucan chain. Many species of bacteria, *Leuconostoc* spp. in particular, produce one or more of these enzymes, and that the branching pattern unique to the dextran thus formed is strain-dependent. Indeed, the branching patterns of the dextran formed by an organism can be used to speciate at strain level. Hence, the type of enzyme or microbe used to generate an oligosaccharide can significantly influence the ultimate structure of the oligosaccharide mixture produced.

There are two broad varieties of dextransucrases (each having one or more isoforms). First, there is the soluble fraction, which can be isolated from centrifuged broth (supernatant). Second, there is a fraction that contains "insoluble" or "low soluble" dextransucrase because it is bound to the cell wall as a dextran complex. Responsible for the formation of capsular extracellular polymeric substances (EPS), this insoluble dextransucrase establishes the layer needed for conversion of sucrose to dextran in bulk media, and takes approximately two hours to form after being expressed by the presence of sucrose in the media (Brooker, 1977). Once formed, dextran forms a thick capsule around the cell. When this occurs in bulk mixtures, thick and recalcitrant biofilms are formed. The distinction between soluble and insoluble dextransucrase is important because the two can produce dextrans with different molecular weight distributions and different linkage patterns. This is why, besides conformational distortion of the active site(s), immobilized enzymes behave differently than those in a bulk fermentation.

Mechanically, dextransucrase enzymes can be the primary synthetic "reagent" for production of oligosaccharides, including MIMOs. For example, *Leuconostoc mesenteroides* NRRL B-512FMC can produce >95% linear α-(1,6) polyglucan from sucrose.

Figure 1:
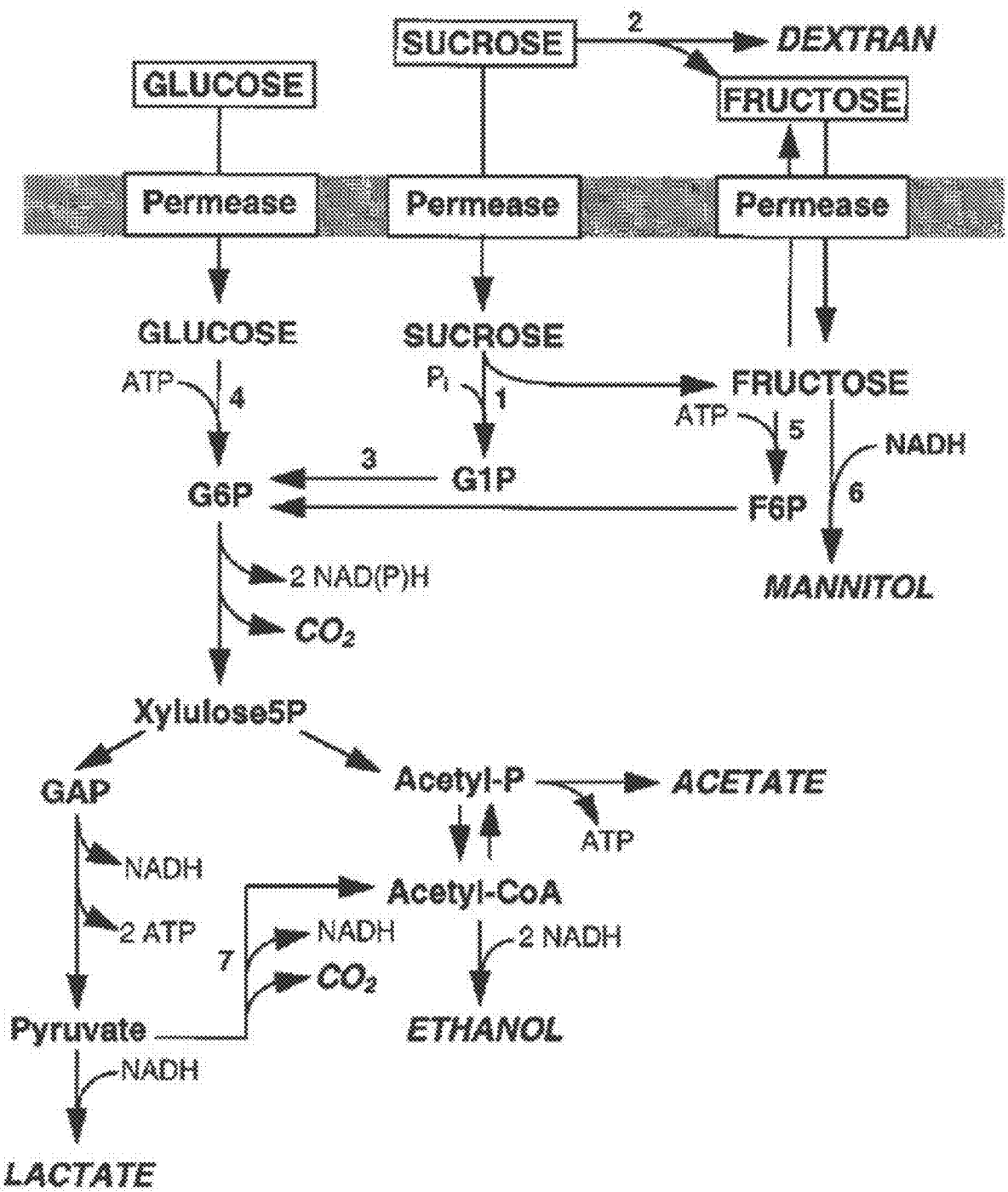
FIG. 1 illustrates the metabolism of *Leuconostoc* spp. (see, Dols, et al. 1997).

Metabolically, *Leuconostoc* spp. typically utilize carbohydrates (sucrose, glucose, and fructose) via heterolactic fermentation, (Dols, et al. 1997), for example, as shown in FIG. 1. In all such microbially-mediated production processes, some of the sucrose is transported into the cell for metabolic purposes, explaining why yield of dextran and or oligosaccharides produced is limited to approximately 50-55%/total sucrose. This also indicates that the competing rates of metabolism and dextran production can impact the outcome of a fermentation.

The expected fermentation stoichiometry is given below for aerobic and microaerobic conditions.

D-glucose+$O_2$→0.92lactic acid+0.95acetic acid+$CO_2$

D-fructose+0.58$O_2$→0.28mannitol+0.71lactic acid+ 0.72acetic acid+0.72$CO_2$  Aerobic D-glucose→0.93 lactic acid+0.92 ethanol+$CO_2$ D-fructose→0.53 mannitol+0.56 lactic acid+0.57 acetic acid+0.57 $CO_2$  Microaerobic Mixtures of isomaltooligosaccharides are generally produced by the action of immobilized enzymes on mono- or disaccharide feedstocks. Isomaltooligosaccharides can also be produced by transglycosylation of starch hydrolysates followed by chromatographic separation. An early process, Chludzinski et al. produced branched isomaltooligosaccharides using dextransucrase (EC 2.4.1.5) expressed from bacterial cultures such as *Leuconostoc* spp. and *Streptococcus* ssp. (Chludzinski, A. M., et al., J. Bacteriol. B:1-7 (1974)). Roper and Koch later disclosed the production of isomaltooligosaccharide mixtures from starch hydrolysates (maltose and maltodextrins) through the action of the α-transglucosidase (EC 2.4.1.24) from *Aspergillus* spp. (Starch, 1988, 40:453-459).

Further differentiation within the MIMO-class involves the addition of glucosyl branches. As illustrated herein, such a branch can be just a single monosaccharide in length. These can occur at the α-(1,2), α-(1,3), and α-(1,4) positions, typically closer to the non-reducing end of the oligosaccharide chain.

Figure 2:
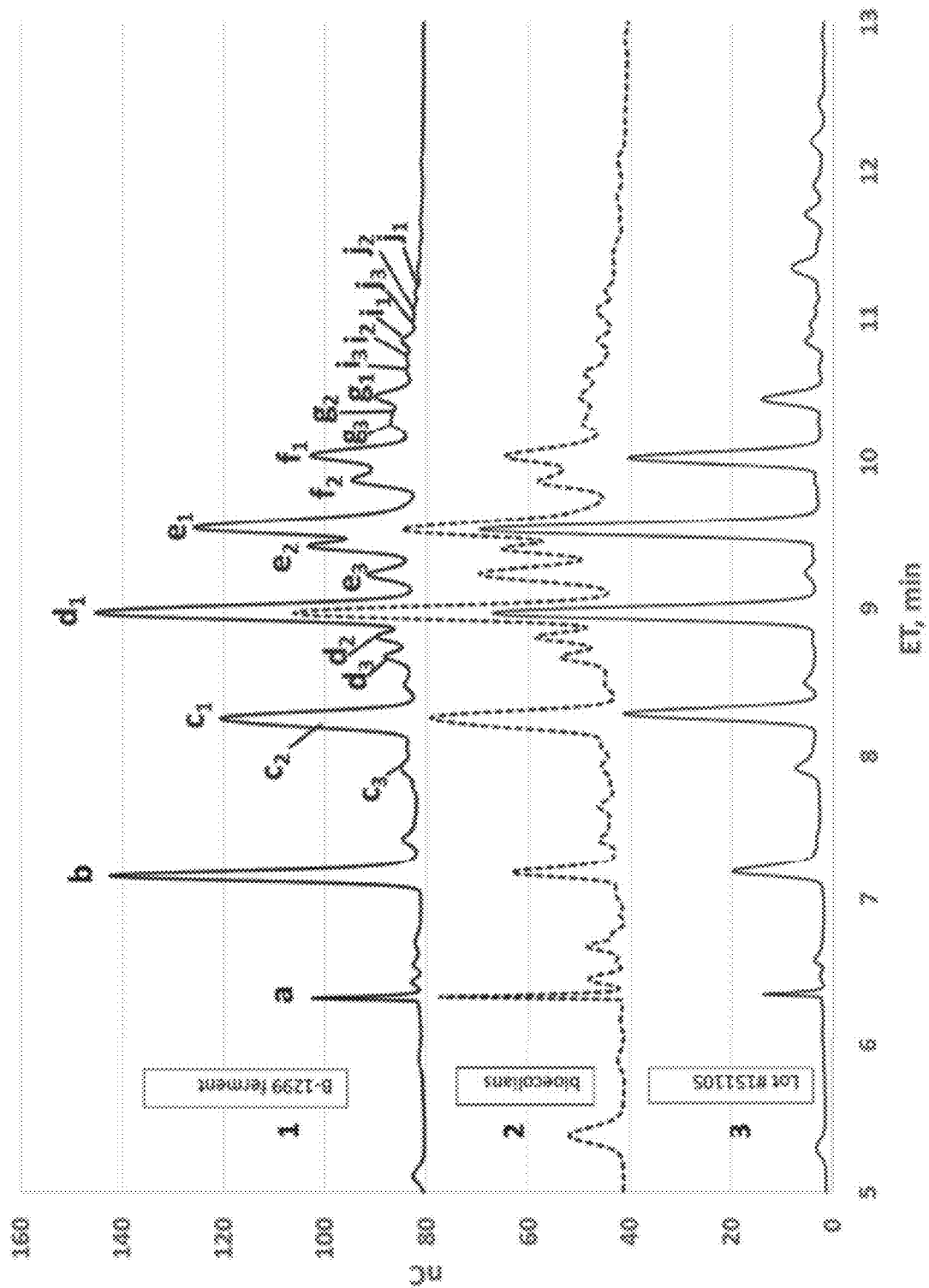
FIG. 2 shows High-Performance Anion-Exchange Chromatography with Pulsed Amperometric Detection (HPAEC- PAD) of various oligosaccharide preparations: (1) a final fermentation broth generated using the ISOThrive process with NRRL B-1299; (2) a commercial MIMO formulation made using an immobilized dextransucrase enzyme from NRRL B-1299; and (3) a typical product made using a process described in U.S. patent application Ser. No. 14/833,094, filed Aug. 22, 2015 (incorporated herein by reference in its entirety) using NRRL B-742. Note that equivalent components a-j are observed, which correspond to a. sucrose, b. maltose, and c-j corresponding to MIMO with (degree of polymerization (DP) 3-9, respectively. Subscript C1 denotes MIMO with (1) α-(1,6) linear chains; (2) α-(1,2) branched chains; and, (3) α-(1,3) branched chains.

The branching patterns are unique to the dextransucrase cohort expressed by a particular bacterial species, and vary tremendously amongst different bacterial strains. For example, while Leuconostoc mesenteroides NRRL B-512F creates dextran EPS that is almost completely unbranched, consisting of >95% α-(1,6) linkages, the dextran produced by L. mesenteroides NRRL B-1299 contains a distribution of three branched oligomers per DP [roughly 65% α-(1,6), 22% α-(1,2), and 12% α-(1,3)], and L. citreum NRRL B-742 produces a dextran that is somewhere in between and can contain 5%-15% α-(1,3). The differences may in the case of NRRL B-512F be attributed to a single sucrose glucan transferase enzyme that is responsible for α-(1,6) linkages, and in the case of NRRL B-1299 the differences may be dues to at least three enzyme isoforms (Dols, et al. Appl Environ Microbiol 64(4): 1298-1302 1998). B-1299 is also capable of expressing glucose glucosyltransferase and fructose glucosyl transferase when grown on glucose and fructose medium, respectively (id.). These enzymes may create different branching patterns, as well. The differences are illustrated in FIG. 2.

The inventors have also observed that the same enzyme cohort (produced by Leuconostoc mesenteroides subsp. mesenteroides (Tsenkovskii) van Tieghem ATCC® 11449™ NRRL B-1299) produces a different branching pattern when immobilized than when it is native in free solution; the results were clear for DP 5 oligosaccharides.

Figure 3:
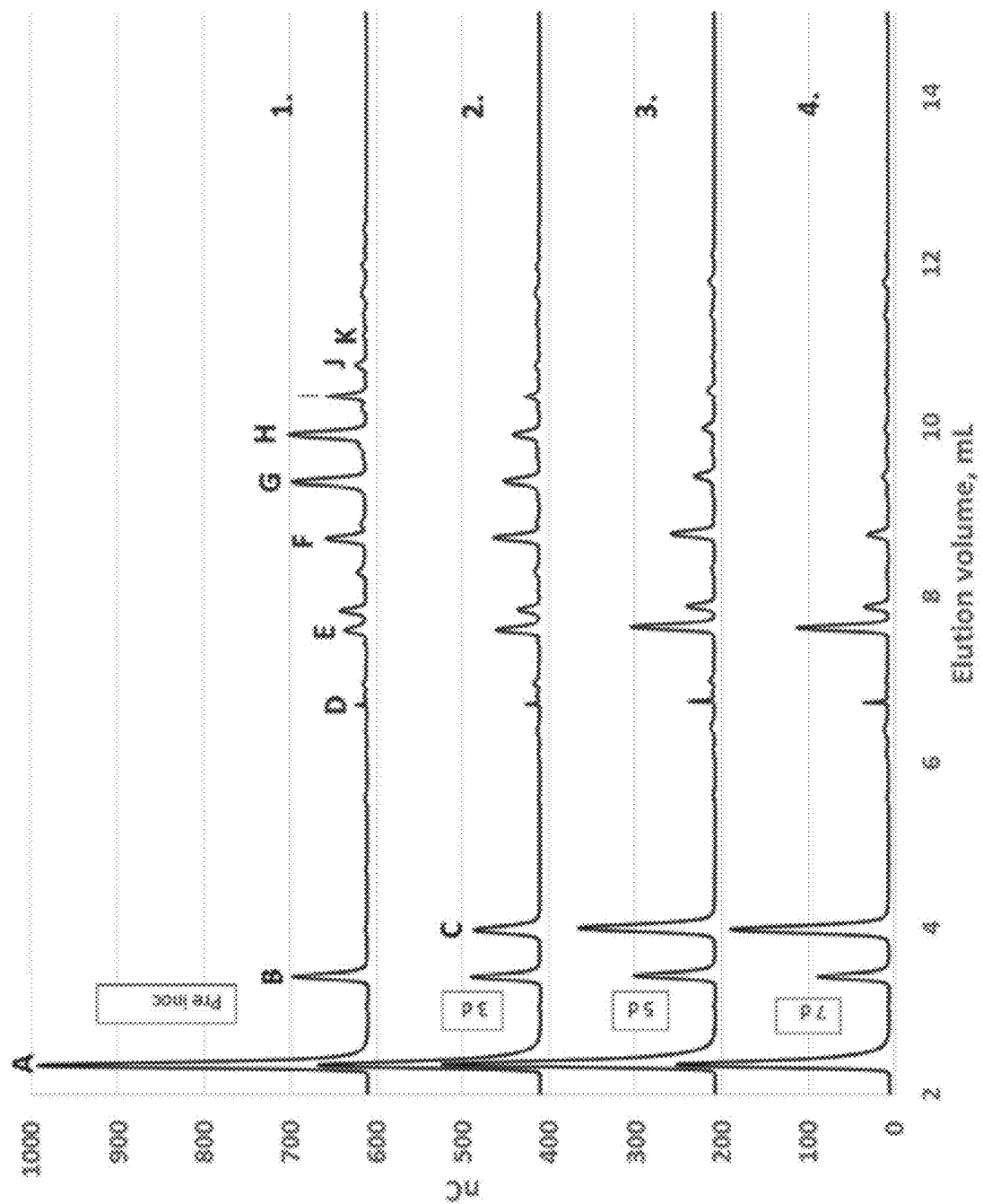
FIG. 3 shows HPAEC-PAD of (1) fermentation medium made to contain ISOThrive™ MIMO corresponding to "A2"-type material. (2), (3), and (4) correspond to the same medium after fermentation with *L. casei* NRRL B-1922 for 3, 5, and 7 days, respectively. Labeled components are A: D-mannitol; B: L-arabinose (internal standard); C: D-glucose; D: sucrose; E: maltose; F: MIMO-DP3 (e.g., panose), and G-K: MIMO DP 4-8. Note that consumption of MIMO occurs via cleavage of maltose and depolymerization of the α-(1,6) glucan backbone chain.

Both branching pattern and molecular weight can have a profound effect on the selectivity of a prebiotic composition. For example, Hu et al. (2013) noted that while Lactobacillus reuteri consumed shorter-chain MIMO, the longer chains (higher molecular weight) were preferred by Bifidobacteria. Further, which bacteria will eat a given prebiotic oligosaccharide depends on the glycolytic enzyme cohort expressed by that bacterial type. For example, the MIMO contained in the composition described herein [>80% linear α-(1,6); also called ISOThrive™], can be fermented by Lactobacillus casei NRRL B-1922. Evidence of this is provided in FIG. 3 where ISOThrive™ composite A2 (see Example #1) material is depolymerized to D-glucose and D-maltose. The compositions described herein (that include MIMOs such as those in ISOThrive™) can thus be characterized as prebiotics for Lactobacillus casei NRRL B-1922, which is representative of a probiotic bacterial class that is both large and popular.

Figure 4:
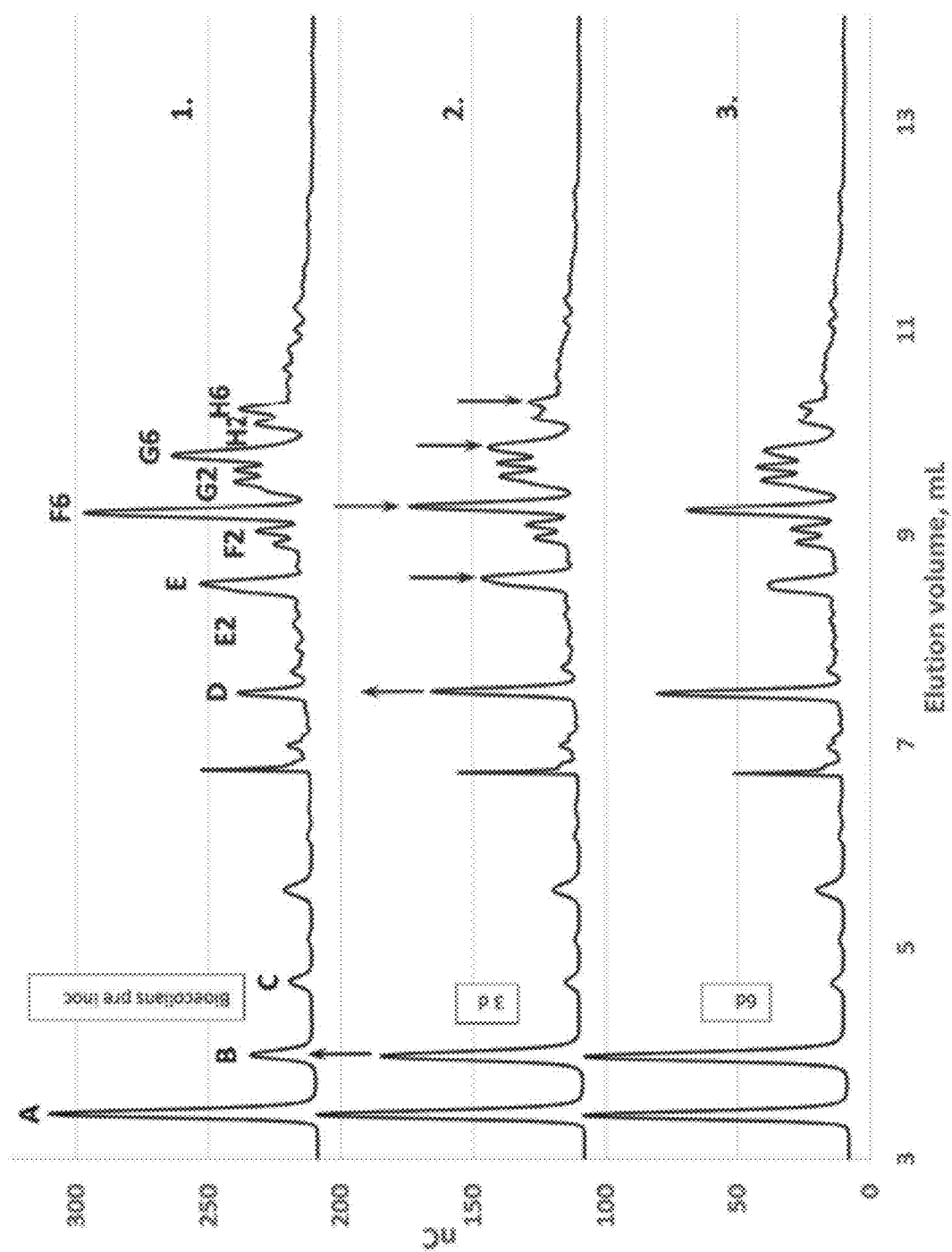
FIG. 4 shows HPAEC-PAD of (1) Fermentation medium made to contain a commercial MIMO product manufactured using immobilized dextransucrase isolated from NRRL B-1299. (2) and (3) correspond to the same medium after fermentation with *L. casei* NRRL B-1922 for 3 and 6 days, respectively. Labeled components are A: L-arabinose (internal standard); B: D-glucose; C: D-fructose; D: maltose; where E, F, G, and H correspond to MIMO with linear α-(1,6) backbones ranging in DP from 3 to 6, and E2, F2, G2, and H2 correspond to MIMO with linear α-(1,6) backbones and either α-(1,2) or α-(1,3) glucosyl branches ranging in DP from 3 to 6. Note preferential consumption of the linear α-(1,6) molecules over the branched moieties. Note also the same product distribution/mechanism as indicated in FIG. 3.

By means of comparison with a composition containing a highly branched-type MIMO (produced via NRRL B-1299 dextransucrase), it can be demonstrated that α-(1,6) linkages are preferred by this organism, and that α-(1,2), and α-(1,3) linkages are not. This comparison is given in FIG. 4.

It was further noted by Moller, et al (2012) that another popular probiotic strain, Lactobacillus acidophilus NCFM, preferred MIMO-DP 3 (panose) over linear α-(1,6) IMO molecules (DP 3-5). Kothori and Goyal (2012) noted that IMOs produced from NRRL B-1426 dextransucrase (DP 2-10, ~15% α-(1,3) branch linkages) were resistant to the action of dextranase, α-glucosidase, and α-amylase. Because the α-(1,6) glucosidase is needed for efficient utilization of IMOs by many bacterial species (e.g. L. casei and acidophilus), resistance to dextranase tends to rule out the prebiotic potential of this sort of IMO for most prevalent probiotic lactobacilli strains.

MIMOs conforming to the panose-type structure of oligosaccharides can exist both naturally, or they can be induced by man, in a variety of fermented foods (valued as a sweetener rather than a prebiotic) including kimchi with Leuconostoc starter culture fortified with sucrose and maltose (Cho, et al. 2014). In fact, many bacterial species known to synthesize exopolysaccharides (EPS), e.g. dextran or levan, from sucrose, have been isolated from sourdough starter cultures. Examples include the following (see Tieking, et al. 2003):

| Isolated species, TMW #: | EPS type: | Monomer: |
|---|---|---|
| L. sanfranciscensis spp. | Levan | Fructose |
| L. frumenti spp. | Levan | Fructose |
| L. pontis spp. | Levan | Fructose |
| L. panis 1.649 | Levan | Fructose |
| L. reuteri 1.106 | Dextran | Glucose |
| L. reuteri 1.109 | Reuteran | Glucose |
| W. confusa 1.617 | Dextran | Glucose |
| W. confusa 1.934 | Levan | Fructose |

Other facultative anaerobic heterofermentative organisms have also been noted including (Corsetti and Settanni, 2007) Leuconostoc, Weissella, Pediococcus, Lactococcus, Enterococcus, and Streptococcus spp. have been isolated from sourdough.

Figure 5:
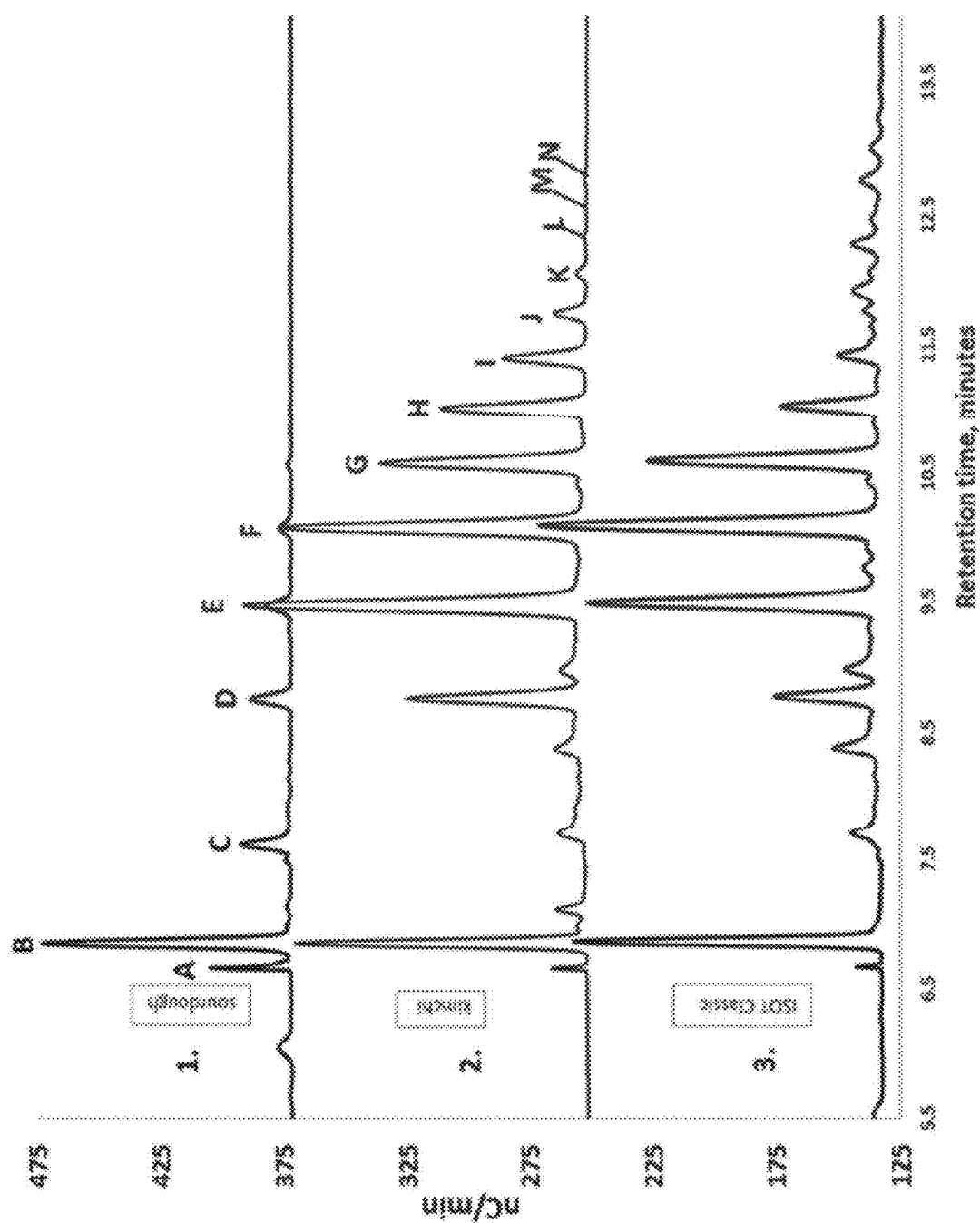
FIG. 5 HPAEC-PAD of (1) MIMO produced in a spontaneously fermented sourdough starter culture from hard red wheat (confirmed *P. pentosaceus* via sequencing of 16SrRNA); (2) Liquor separated from *kimchi* (found to contain several *Leuconostoc* spp., primarily *L. gasicomitatum*, via sequencing of 16SrRNA) with sucrose and maltose added at a ratio of 3:1; and (3) A sample of ISOThrive™ MIMO produced via fermentation of sucrose and maltose with NRRL B-742. Labeled components are A: sucrose; *B. raffinose* (internal standard), C: maltose, where D, E, F, G, H, I, L, M, and N correspond to MIMO with α-(1,6) linear backbones ranging in DP from 3 (panose) to 10.

As shown by the inventors, all but Enterococcus spp. (which produce heteropolymeric EPS) produce either dextran or levan (see also, Mozzi, et al. 2006). The inventors have shown that some MIMO is present in a spontaneous sourdough fermentation of red wheat flour, where it was noted to arise from sucrose in the flour and maltose from the starch. See, e.g., FIG. 5. Subsequent analysis revealed that the starter culture was Pediococcus pentosaceus.

The bacterial strains present in the kimchi (beginning and end of fermentation) were determined via high-throughput PCR and sequencing of the 16S rRNA; the results are given here:

| Sample ID | Species | Kimchi Juice |
|---|---|---|
| NR 102781 | Leuconostoc carnosum JB16 | 6.8% |
| NR 074997 | Leuconostoc gasicomitatum LMG | 42.1% |
| NR 102984 | Leuconostoc gelidum JB7 | 12.2% |
| NR 025204 | Leuconostoc inhae strain IH003 | 2.6% |

Recently, use of the enzyme glucosyltransferase isolated from Leuconostoc mesenteroides has been reported by Remaud et al., who disclosed production of linear and short-branched oligosaccharides with α-(1→6) linkages and a maltose at the reducing end (Remaud, M., et al., J. Carbohydrate Chem., 1992, 11(3):359-378). Remaud et al. used a feedstock starting ratio of 7:1 sucrose:maltose in a reaction catalyzed by extracellular Leuconostoc mesenteroides ATCC 13146 glucosyltransferase that produced branched dextrans with α-(1-3) linkages (id.). The same group has reported the production of branched α-(1,2) isomaltooligosaccharide mixtures from sucrose with an acceptor reaction catalyzed by dextransucrase (Remaud-Simeon, M. et al., Appl. Biochem. Biotechnol. 1994, 44:101-17).

Paul et al. disclosed the synthesis and purification of branched isomaltooligosaccharide mixtures containing an α-(1,2) bond by the action of soluble and insoluble glucosyltransferase isolated from Leuconostoc mesenteroides B-1299 on sucrose and a glucosyl acceptor such as maltose (or a material rich in maltose, such as a starch hydrolysis product), isomaltose, methyl α-glucoside, isomaltotriose or glucose (or a material rich in glucose, such as a starch hydrolysis product) (Paul, F. et al., U.S. Pat. No. 5,141,858).

D-fructose, the byproduct of transglucosylation via sucrose, is a difficult compound to separate from the isomaltooligosaccharide product, and can be a detriment to use of this product in human nutrition, given the current information about the negative effects of high fructose syrups. (See: Ouyang, X., et al., J. Hepatol., 2008, 48(6): 993-9. doi: 10.1016/j.jhep.2008.02.011. Epub 2008 Mar. 10; Dhingra, R. et al., Circulation, 2007, 116:480-488; Swanson, J. E., et al., Am. J. Clin. Nutr., 1992, 55(4):851-856; and Vartanian, L. R., et al., Am. J. Public Health, 2007, 97(4): 667-75. Epub 2007 Feb. 28.)

Preferred Methods of Producing MIMOs Compositions

On a commercial scale, the composition of the present invention can be produced as described in U.S. patent application Ser. No. 14/833,094, filed Aug. 22, 2015, and entitled "Process for the Production of Isomaltooligosaccharides," which is herein incorporated by reference in its entirety.

A process flow diagram of the manufacturing process is provided in FIG. 36. In general, the process consists of two steps including, first, the enzymatic synthesis of MIMO via extracellular dextransucrase expressed by a suitable organism during the fermentation, in rich medium containing sucrose, and second, downstream processing to remove biomass, residual salts/minerals, and bacterial metabolites.

Certain metabolites, particularly D-mannitol, can remain in the MIMO product composition and positively affect its organoleptic character.

The compositions described herein can have a pH that is sufficiently low (1.5 to 2.8 pH, 1.5 to 4.2 pH, or 2.0 to 4.2 pH) to prevent microbiological spoilage and or pathogens while improving the organoleptic character of the composition. For example, the product pH can in some cases be pH 1-7, or pH 1-6, or pH 1-4, or pH 1-3, or pH 1.5-3.0, where pH 1.5-2.8 is preferred. A variety of acidulants may be added including, but not limited to, organic acids including citric, malic, lactic, tartaric, fumaric, succinic, ascorbic, benzoic, adipic, caprylic, propionic, acetic acids, and salts (mono, di- and tri-Na, Mg, Ca, etc.), stereoisomers (L/D, R/S, meso), rotamers, esters, and mixtures thereof, and mineral acids including phosphoric, hydrochloric, sulfuric, and salts, esters, and mixtures thereof, and amino acids, including lysine, cysteine, methionine, glutamic, and aspartic acids, and salts, esters, and mixtures thereof.

In addition, the composition can in some cases be concentrated to a sufficiently high water activity (aW) to protect the shelf life.

Hence, in some cases, the low amounts of water and the low pH can protect the composition from spoilage or microbial growth.

Figure 6:
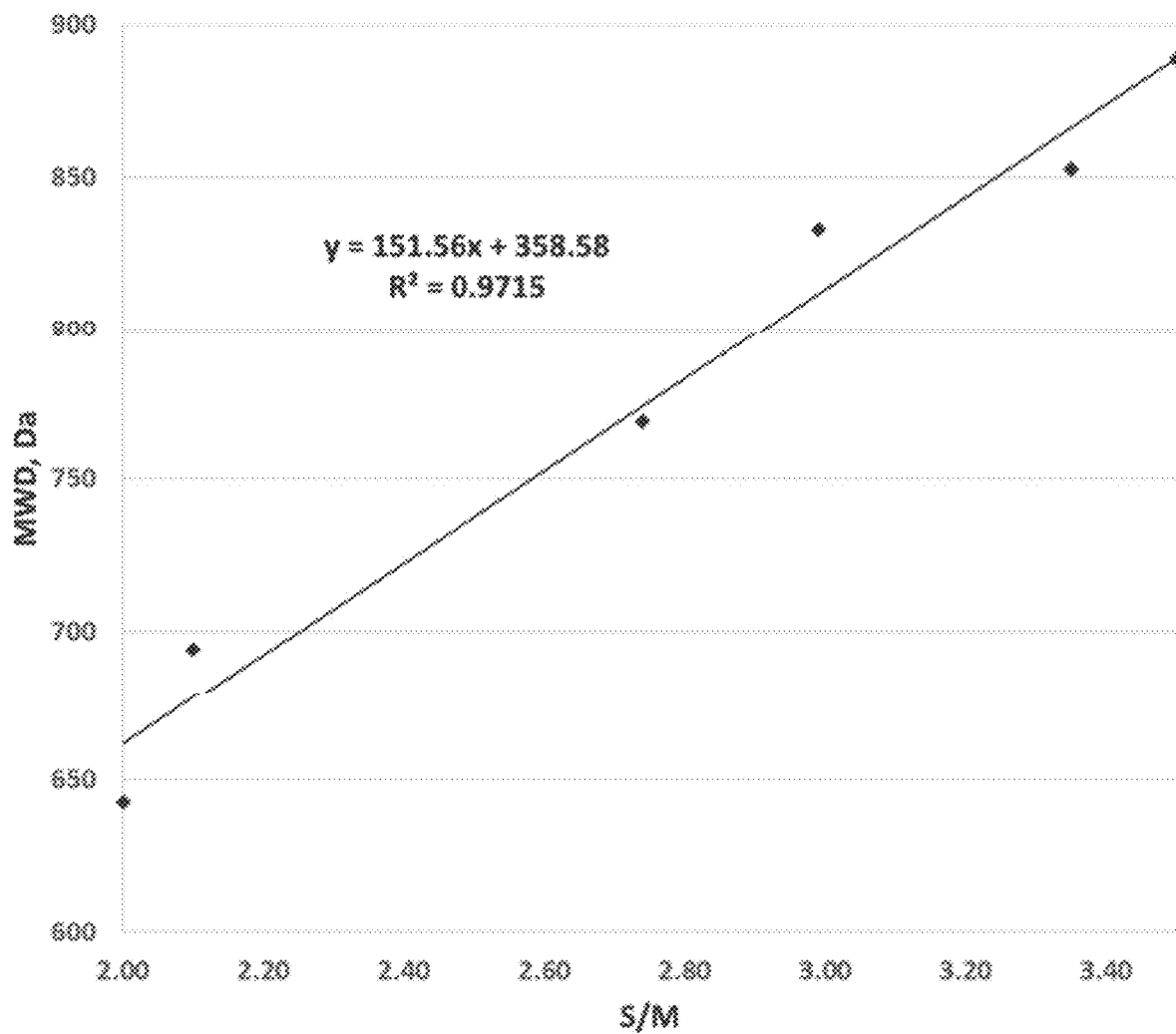
FIG. 6 shows the effect the sucrose:maltose (S/M, w/w) ratio at the time of inoculation has on the mass average molecular weight distribution (MWD) at a fixed pH of 5.5. As S/M increases, so does the molecular weight distribution.

The mass average molecular weight distribution (MWD) of the MIMO tends to increase with sucrose:maltose (S/M) ratio present at the time of inoculation (see FIG. 6). The relationship between sucrose:maltose ratio and the MWD of the product can be approximated (±6%, $R^2=0.9715$, N=29) as: MWD, Da=151.56*S/M+358.58. Note that although a previous U.S. patent application Ser. No. 14/833,094, filed Aug. 22, 2015, mentions that as the S/M increases so does the molecular weight distribution, that previous application did not provide a mathematical relationship between sucrose:maltose ratio and the MWD of the product. Further studies have been performed, and the relationship between sucrose:maltose ratio and the MWD of the product has been defined more precisely herein.

Figure 7:
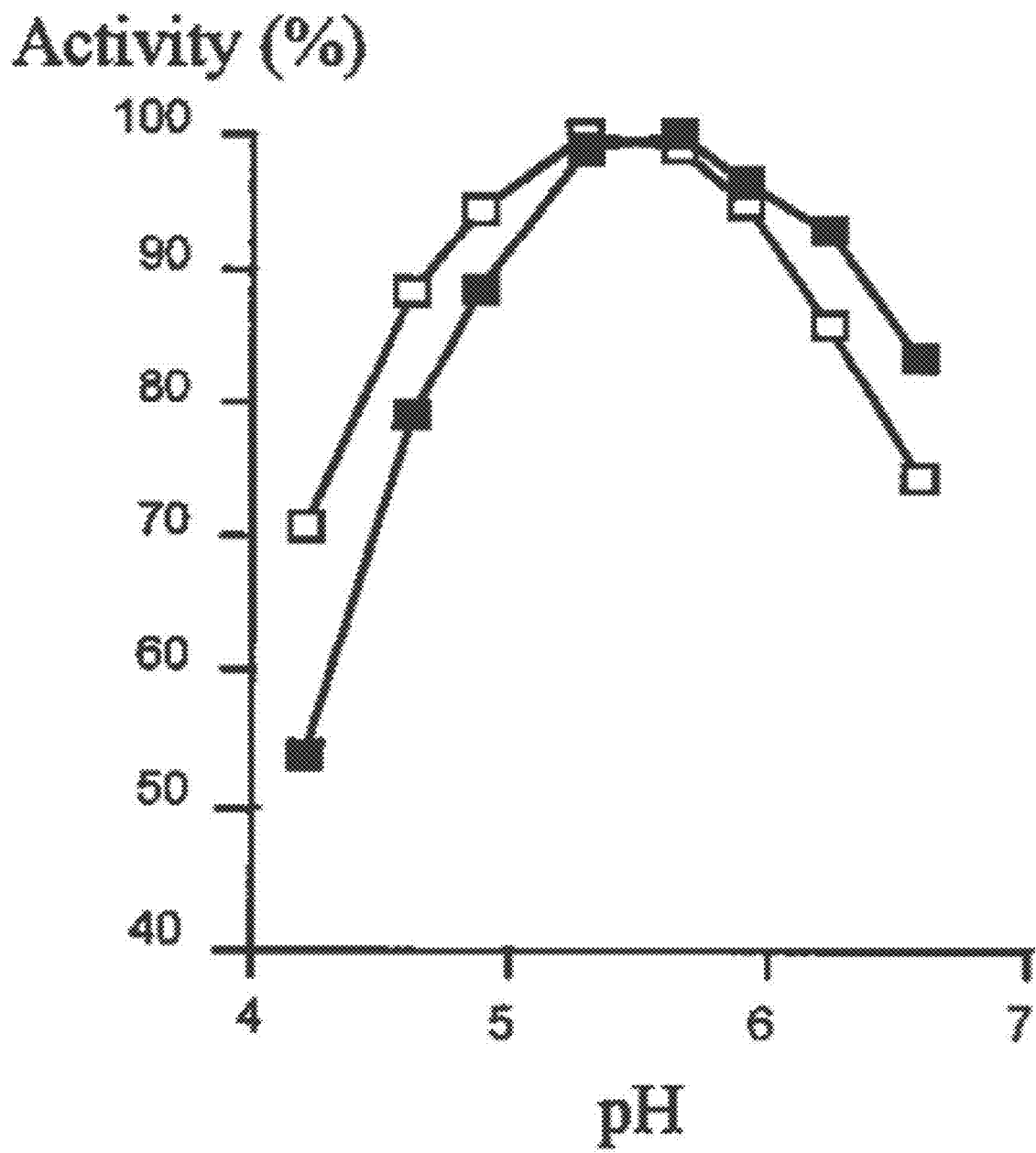
FIG. 7 shows the pH optimum for dextransucrase produced by *Leuconostoc mesenteroides* NRRL B-512F either without (white squares) or with (black squares) stabilization via added dextran T-70 (Monchois, et al. 1998). The mass average molecular weight distribution (MWD) increases as the optimum is approached.

The mass average molecular weight distribution is also dependent on the pH optimum of the dextransucrase(s) expressed by the fermenting organism. For dextransucrases from *Leuconostoc* spp. (NRRL B-512F, B-742, and B-1299), this optimum is 5.5±0.3 (Miller et al. 1986, Dols-Lafargue et al. 2001). This behavior with respect to pH appears to be conserved within enzymes produced by a variety of organisms. For example, the pH optimum for dextransucrase isolated from *Pediococcus pentosaceous* is 5.4 (Patel, et al. 2011) and that from *Streptococcus mutans* was optimum at 5.5 (Chludzinski et al. 1974). The pH optimum is rather broad, and can be affected by substrate concentration (Sarwat, et al. 2008), ionic strength, and the presence of certain cations such as magnesium and calcium (Patel, et al. 2011). Furthermore, gene deletions modifying the carboxy-terminus of the active site in dextransucrase from NRRL B-512F affected neither km nor the pH optimum (Monchois, et al. 1998). A typical pH optimum curve for the B-512F enzyme is given in FIG. 7, and the dextransucrase involved with the synthesis of the composition described herein is typical.

The mass average molecular weight distribution (MWD) is approximated by a function dictated by pH optimum, but is, in the embodied process, attenuated, and, at a sucrose: maltose ratio S/M of 2.00 (approximately 2.73 at time of inoculation) appears to have a quadratic maximum between pH 5.5 and 6.0 that can be approximated by the following:

$$\text{MWD, Da} = -159.1 * \text{pH}^2 + 1866.1 * \text{pH} - 4688.$$

Note that although a previous U.S. patent application Ser. No. 14/833,094, filed Aug. 22, 2015, mentions that, as pH either increases above or decreases below the optimum range for the enzyme, both the molecular weight distribution and MIMO yield decrease, that previous application did not provide a mathematical relationship between pH set during fermentation and the MWD of the product. Further studies have been performed, and the relationship between pH and the MWD of the product has been defined more precisely herein.

The organisms used herein, including *Leuconostoc mesenteroides*, are capable of producing dextransucrase, and can be utilized to produce the composition containing maltosyl-isomaltooligosaccharides pursuant to the methods described herein. In another example, *L. citreum* ATCC 13146 (NRRL B-742) may be used. This bacterium is known by other designations by those skilled in the art, including the designation *Leuconostoc citreum* ATCC 13146, the designation NRRL B-742, the designation *Leuconostoc citreum* Farrow, and the designation *L. amelibiosum*. The bacterium *Leuconostoc mesenteroides* subsp. *mesenteroides* (Tsenkovskii) van Tieghem ATCC® 11449™ (NRRL B-1299) can also be employed. In addition, the inventors have also tested *L. citreum* B-1355, *Weissella confusa* B-1064, and *Lactobacillus sanfransiscensis* ATCC 27651. The B-1355 *L. citreum* B-1355 and *Weissella* makes MIMO, and can make larger MIMO molecules.

Other useful dextransucrase/alternansucrase-producing microorganisms include, but not limited to, *Leuconostoc* spp (specifically *mesenteroides, citreum, gasicomitatum, carnosum, gelidum, inhae,* and *kimchi*), *Weissella* spp (specifically *confusa, kimchi*), *Lactococcus* spp., *Streptococcus* spp. (specifically *mutans*), *Lactobacillus* spp. (e.g. *reuteri*), *Pediococcus* spp. (specifically *pentosaceus*), and certain mutant *E. coli*. Useful microorganisms, or mixed cultures thereof, may also be isolated from natural sources including, but not limited to, spontaneous (wild) sourdough starter cultures (the bioorganism mixture used in the production of sourdough bread) and *kimchi*.

The organism used in the Examples described herein is *Leuconostoc citreum* Farrow et al. ATCC 13146 (NRRL B-742).

Synthesis

On a commercial scale, the composition of the present invention may be produced as described in U.S. patent application Ser. No. 14/833,094, filed Aug. 22, 2015, entitled "Process for the Production of Isomaltooligosaccharides", which is herein incorporated by reference in its entirety.

In general, upon start-up of the fermentation process, the entire equipment system is flushed, cleaned and sterilized. A fermentation tank is charged with the requisite media components (typical vitamins, sulfates, phosphates, salts and other materials used for bacterial culture, sucrose, and maltose in a defined sucrose to maltose ratio. All ingredients are non-GMO and certified Kosher/Pareve, including the bacterial vial stock. Separately, the inoculum (in the preferred approach, ATCC 13146) is grown until achieving an optical density of at least 1 (OD, or absorbance at 660 nm via UV-VIS spectrophotometer), and added to the fermentation in a volume in the range of about 1% to about 10% (1% in the preferred approach) of the amount contained in the bulk media. The fermentation takes place at a temperature of about 27° C. and is maintained at pH 4.0-6.0 (5.5 in the preferred approach) via addition of 50% w/w sodium hydroxide. The fermentation is not aerated, but the headspace is pressurized with air as needed to maintain positive pressure. The fermentation is continued until no fructose is present, for a period of approximately 25 to 60 hours. The characteristics and behavior of the feedstock, products, and metabolites throughout the course of fermentation are given in Examples 3, 4, 6, and 7. Most, if not all, of the sucrose and maltose are either consumed or converted to MIMO within a few hours, usually within about 10 hours.

The fermentation is continued for a certain amount of time thereafter to allow the MIMOs produced to be enzymatically rearranged to yield longer chains (higher MWD), if desired. Typically, the time required to create a product, for example, of target MWD of 760-800 Da is about 55 Hr. Ideally, the batch will be run, with periodic sampling and analysis by HPAEC-PAD and/or NMR until the target MWD is reached and the broth is essentially free of fructose. The fermentation would then be terminated and moved into downstream processing. The behavior of the MWD of MIMO throughout the course of a 3000 L commercial fermentation is given in Examples 6 and 7.

Downstream Processing

The composition of the present invention may be purified as described in U.S. patent application Ser. No. 14/833,094, filed Aug. 22, 2015, entitled "Process for the Production of Isomaltooligosaccharides," which is incorporated herein by reference in its entirety.

During the production of the maltosyl-isomaltooligosaccharides composition, the MIMO fermentation can be determined to be complete as determined by the conversion of the fructose to mannitol and by achievement of a target molecular weight distribution. In some cases, the MIMO fermentation is determined to be complete when the fructose is consumed, by conversion of fructose to mannitol, and/or by cessation of the take up of alkali. Hence, the amount of fructose in the final fermentation fluid can be less than less than 4%/brix fructose, or less than 3%/brix fructose, or less than 2%/brix fructose, or less than 1%/brix fructose, or less than 0.5%/brix fructose, or less than 0.25%/brix fructose as detected by HPAEC-PAD or HPLC-RID.

The cells can be separated from the broth by microfiltration, centrifugation, or by other broth clarification processes. The cells are then discarded.

The broth can be concentrated by evaporation to 35-45 brix and decolorized with powdered activated carbon (PAC, 0.4-2.0%/broth mass) at about 60-80° C. Alternatively, either granulated activated carbon (GAC) or powdered activated carbon (PAC) may be used, which is later removed by filtration. In another example, granulated activated carbon (GAC) or powdered activated carbon (PAC) can be packed into a jacketed column and used for decolorization in a single-pass or multiple-pass operation.

The decolorized liquor is then demineralized and the organic acid metabolites removed by a two-stage ion exchange process (IEX), whereby the liquor is contacted first with a strong acid cation (SAC) ion exchange resin, and second, the liquor is contacted with a weak base anion (WBA) IEX resin.

The resulting liquor (2-10 brix) is adjusted to pH<4.2 (typically 2.0-4.0) with phosphoric acid ($H_3PO_4$, 85%, 0.25-2.00 kg) and is concentrated by evaporation to 45-60 brix (56 is the preferred approach). The resulting concentrate is slowly cooled, with gentle agitation, to room temperature and allowed to crystallize.

The resulting liquor is separated from the crystals (D-mannitol) via filtration (Nutsch) or by basket centrifuge. The crystal cake is washed with water (100-200% cake mass at 77% to 95% solids, 125-150% is preferred). The washings are either retained for future batch runs or combined with the liquor and concentrated by evaporation to 60-70 brix (67-69 brix is preferred).

The resulting concentrate is slowly cooled, with gentle agitation, to room temperature (19-25° C.) and crystals allowed to seed. Once the initial target temperature has been reached, the whole is then cooled slowly to 2-10° C. (5° C. is preferred) until crystallization is complete.

The resulting liquor is separated from the crystals (D-mannitol) via filtration (Nutsch) or by basket centrifuge. The crystal cake is washed with cold water (100-200% cake mass with 77% to 95% solids, 125-150% cake mass at 95% solids is preferred).

The product liquor is pasteurized (70° C. for 30 min.) prior to pack out. The washings are retained and frozen for recycle into the next batch run as appropriate.

Where the concentration of the components in the composition so prepared will fall into the ranges established below. The composition may be liquid at 59-68%/brix or a spray dried/lyophilized powder. The MWD can be inside the range of 730 and 900 Da (mass average).

| Component: | Minimum %/brix: | Maximum %/brix: |
|---|---|---|
| MIMO DP3-9: | 69.00 | 100.00 |
| D-Mannitol: | 0.00 | 14.00 |
| D-Glucose | 0.00 | 2.50 |
| D-Fructose | 0.00 | 0.50 |
| Sucrose | 0.00 | 6.00 |
| D-Maltose | 0.50 | 7.00 |
| Lactate | 0.00 | 6.50 |
| Glycerol | 0.00 | 2.50 |
| Formate | 0.00 | 1.00 |
| Acetate | 0.00 | 10.00 |
| Purity, %: | 69.00 | 100.00 |

The following composition is prepared on a commercial scale and is preferred. Syrups are typically between 62 and 65 brix.

| Component: | Minimum %/brix: | Maximum %/brix: |
|---|---|---|
| MIMO DP3-9 | 84.77 | 95.51 |
| D-Mannitol | 6.23 | 8.35 |
| D-Glucose | 0.46 | 0.85 |
| D-Fructose | 0.05 | 0.16 |
| Sucrose | 1.75 | 1.86 |
| D-Maltose | 4.29 | 4.39 |
| Glycerol | 0.41 | 0.51 |
| Total | 98.58 | 111.03 |

The MIMOs are distributed over a range of DP values between two and nine with a mass-average molecular weight distribution in the range of 730-900 Da:

| Component: | Minimum %/brix: | Maximum %/brix: |
|---|---|---|
| maltose | 0.93 | 6.83 |
| MIMO-DP3 | 4.17 | 14.89 |
| MIMO-DP4 | 10.80 | 31.62 |
| MIMO-DP5 | 13.04 | 29.89 |
| MIMO-DP6 | 8.03 | 21.03 |
| MIMO-DP7 | 2.90 | 13.79 |
| MIMO-DP8 | 1.24 | 8.25 |
| MIMO-DP9 | 0.00 | 3.69 |

Wherein a MWD of 780 Da±1.65% is commercially prepared, and thus preferred:

| Component: | Minimum %/brix: | Maximum %/brix: |
|---|---|---|
| maltose | 4.29 | 4.39 |
| MIMO-DP3 | 11.89 | 14.89 |
| MIMO-DP4 | 22.19 | 28.06 |
| MIMO-DP5 | 23.66 | 28.67 |
| MIMO-DP6 | 15.23 | 16.77 |
| MIMO-DP7 | 5.75 | 6.58 |
| MIMO-DP8 | 2.48 | 2.80 |
| MIMO-DP9 | 0.58 | 0.73 |

Wherein the composition differs from all other commercial IMO products by virtue of overall composition (MIMO purity), MIMO MWD, and/or proportion of glycosidic linkage types.

It is understood that the terminology used herein is for the purpose of describing particular embodiments only, and is not intended to be limiting, since the scope of the present application will be limited only by the appended claims and their equivalents.

Treatment

The compositions described can be administered in a regimen that fosters the growth and/or activity probiotic microorganisms that can be present in the digestive or gastrointestinal system of an animal. For example, the compositions described herein can be administered to animals, including humans, domesticated animals, zoo animals, and wild animals. The compositions can be used routinely or intermittently to foster the growth and/or activity of probiotic microorganisms that can be present in the digestive or gastrointestinal system of an animal.

The compositions contain an amount of MIMOs that can be effective for fostering the growth and/or activity of probiotic microorganisms. An effective amount can, for example, be an amount sufficient to foster probiotic microorganism growth by at least about 5%, 10%, 20%, 25%, 30%, 40%, 50%, 60%, 70%, 75%, 80%, 85%, 90%, 93%, 94%, 95%, 96%, 97%, 98%, 99%, 99.5%, or 99.9%. In some cases, the population of probiotic microorganisms can be increased in a gastrointestinal system of an animal who has received the compositions described herein. For example, the population of probiotic microorganisms can increase by about two-fold, or about three-fold, or about four-fold, or about five-fold, or about six-fold, or about seven-fold, or about ten-fold.

The compositions can be administered or ingested once a day, or twice a day, or three times a day. In some cases, the compositions can be administered or ingested every day for one week, or for one month, or for two months, or for three months, or for six months, or for one year, or for two years, or for three years. In many cases the compositions can be administered or ingested every day indefinitely. The compositions may be administered in single or divided dosages.

The compositions described herein can include a mixture of MIMOs as described herein. Inactive ingredients can be present in the compositions such a mannitol and some of the other components described herein. For example, the MIMOs can be present as about 50%, or about 60%, or about 65%, or about 70%, or about 75%, or about 80%, or about 85%, or about 90% or about 95%, or about 96%, or about 97%, or about 98%, or about 99% of the composition.

The compositions can be administered or ingested in amounts of at least about 0.01 mg/kg to about 100 mg/kg, of at least about 0.01 mg/kg to about 300 to 500 mg/kg, at least about 0.1 mg/kg to about 100 to 300 mg/kg or at least about 1 mg/kg to about 50 to 100 mg/kg of body weight, although other dosages may provide beneficial results. For example, the compositions can be administered or ingested in amounts of at least about 0.1 g, or at least about 0.25 g, or at least about 0.5 g, or at least about 0.7 g, or at least about 0.8 g, or at least about 0.9 g, or at least about 1.0 g, or at least about 1.1 g, or at least about 1.2 g. The unit dosage can vary from about 0.01 g to about 50 g, from about 0.01 g to about 35 g, from about 0.1 g to about 25 g, from about 0.5 g to about 12 g, from about 0.5 g to about 8 g, from about 0.5 g to about 4 g, or from about 0.5 g to about 2 g.

The amount administered will vary depending on various factors including, but not limited to, what types of compound(s), and/or other therapeutic agents are administered, the route of administration, the progression or lack of progression of the disease, the weight, the physical condition, the health, the age of the patient, whether prevention or treatment is to be achieved, and if the antigen or ligand is chemically modified. Such factors can be readily determined by the clinician employing animal models or other test systems that are available in the art.

Compounds and compositions thereof may be administered in a single dose, in multiple doses, in a continuous or intermittent manner, depending, for example, upon the recipient's physiological condition, whether the purpose of the administration is therapeutic or prophylactic, and other factors known to skilled practitioners. The administration of the compositions may be essentially continuous over a pre-selected period of time or may be in a series of spaced doses. Both local and systemic administration is contemplated.

In some cases, the compositions are formulated as liquid formulations. Alternatively, the MIMO compounds and other ingredients may be in powder form, obtained by aseptic isolation of sterile solid or by lyophilization from solution, for constitution with a suitable vehicle, e.g., sterile, pyrogen-free water, before use.

When the MIMOs are prepared for oral administration, they can be combined with a carrier. Such a carrier can be a pharmaceutically acceptable carrier, diluent or excipient. The compositions can be provided in the form of a unit dosage form. For oral administration, the MIMOs may be present as a powder, a granular formulation, a solution, a suspension, an emulsion or in a natural or synthetic polymer or resin for ingestion of the active ingredients from a chewing gum. The therapeutic agents may also be presented as a bolus, electuary or paste.

In some case, the compositions can be prepared for, and administered as, oral compositions. For example, tablets or caplets containing the compounds, and optionally a carrier can include buffering agents such as calcium carbonate, magnesium oxide and magnesium carbonate. Caplets and tablets can also include inactive ingredients such as cellulose, pre-gelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, zinc stearate, and the like. Hard or soft gelatin capsules containing at least one therapeutic agent of the invention can contain inactive ingredients such as gelatin, microcrystalline cellulose, sodium lauryl sulfate, starch, talc, and titanium dioxide, and the like, as well as liquid vehicles such as polyethylene glycols (PEGs) and vegetable oil. Moreover, enteric-coated caplets or tablets containing one or more of the compounds of the invention are designed to resist disintegration in the stomach and dissolve in the more neutral to alkaline environment of the duodenum.

The compositions can also include antioxidants, surfactants, preservatives, film-forming, keratolytic or comedolytic agents, perfumes, flavorings and colorings. Antioxidants such as t-butylhydroquinone, butylated hydroxyanisole, butylated hydroxytoluene and α-tocopherol and its derivatives can be added.

The subjects to whom the compositions can be subjects that may have one or more diseases or conditions. Examples of diseases or conditions can include cancer, pre-cancerous condition(s) or cancerous propensities, diabetes (e.g., type 2 diabetes, or type 1 diabetes), autoimmune disease(s), acid reflux, vitamin deficiencies, mood disorder(s), degraded mucosal lining(s), ulcerative colitis, digestive irregularities (e.g., Irritable Bowel Syndrome, acid reflux, constipation, or a combination thereof), inflammatory bowel disease, ulcerative colitis, Crohn's disease, gastroesophageal reflux disease (GERD), infectious enteritis, antibiotic-associated diarrhea, diarrhea, colitis, colon polyps, familial polyposis syndrome, Gardner's Syndrome, *Helicobacter pylori* infection, irritable bowel syndrome, and intestinal cancers. The compositions can foster the growth and activity of certain types of bacteria (e.g., *L. lactis* strains) leads to the production of various types of bacteriocins (e.g., nisins) that can act as anti-cancer agents and/or as anti-microbial agents. For example, early studies indicate that the compositions described herein can reduce or eliminate symptoms in 81% of users who self-identified as having acid reflux symptoms once a week or more.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present application, the preferred methods and materials are now described.

As utilized in accordance with the present disclosure, the following terms, unless otherwise indicated, shall be understood to have the following meanings:

"Brix", also known as degrees Brix (symbol ° Bx), refers to the sugar content of an aqueous solution. One degree Brix is 1 gram of sucrose in 100 grams of solution and represents the strength of the solution as percentage by weight (% w/w). Brix also accounts for dissolved salts, organic acids, and other solutes that increase the refractive index of the solution. As such, it is less useful as a quantitative measure of saccharide content in complex broth (fermentation mixtures), but is quite accurate with respect to the refined product. Thus, 1 degree brix=1 g refractive dry solids per 100 g of material. If the solution contains dissolved solids other than pure sucrose, then the ° Bx only approximates the dissolved solid content. However, when the constituent components of the compositions to be compared are similar and/or within similar ranges, Brix values are reproducible and provide an approximation which, in this case, is an accurate (relative to true dry solids via evaporation) measurement of relative dry solids per each composition.

"Optical density" or "OD" refers to an estimation of cellular density in a fermentation. Typically used to determine the progress of a fermentation, it is determined via absorbance of light at 600 nm and may be referenced to dry cell mass.

"HPAEC-PAD" refers to a hyphenated instrumental analytical technique known as High Pressure Anion Exchange (HPAEC) liquid chromatography (ThermoDionex ICS-5000+) with a Pulsed Amperometric Detector (PAD). Under the scope of this work, this instrument is used solely for the high-resolution separation (ThermoDionex Carbopac PA-100, pH>12.5, acetate gradient elution) of sugar alcohols, mono and disaccharides, and oligosaccharides. Quantification is done via internal standard using L-arabinose and response factors relative to either the pure compound or to a purified maltodextrin of equivalent molecular weight.

"HPLC-RID" refers to a hyphenated instrumental analytical technique known as High Pressure Liquid Chromatography (HPLC, Agilent 1100) with a Refractive Index Detector (RID). Under the scope of this work, this instrument is used to separate (BioRad Aminex HPX-87H, 0.008N $H_2SO_4$ isocratic) and quantify organic (carboxylic) acids that result from bacterial fermentation. This instrument is also used to confirm DP 3, maltose, and mannitol. Quantification is done via external standard method vs. a mixed standard made from target compounds of known purity.

"SIP" refers to sterilized in place.

"SBF" refers to sterilization by filtration through a 0.2 μm membrane.

"CIP" refers to cleaned in place.

"DSP" refers to downstream processing.

"PRMXE" refers to filter cartridge series PRMXE or "Pur-Maxx E" dual-layer pleated polyethersulfone membrane sterilizing grade (SG) cartridges; 0.20 μm.

"Degree of polymerization", or "DP", refers to the number of monosaccharide sugar units in a given oligosaccharide.

"Oligosaccharides" refers to glycans of all kinds with DP>=3 and <=10.

"Molecular weight distribution," or "MWD" refers to the mass-average molecular weight of a distribution of oligosaccharides.

"Oligosaccharides" refers to glycans of all kinds, generally with a degree of polymerization (DP) greater than or equal to 3 and less than or equal to 18.

"Glucooligosaccharide", or "GlcOS", refers to homopolymer oligosaccharides (comprised of glucose in any structural arrangement). GlcOS include the maltooligosaccharide series, typically derived from plant starch. One example, is [—O-α-(1,4)-], maltopentaose, which has the following chemical structure:

"Maltosyl-isomaltooligosaccharides," or MIMOs, refers to oligosaccharide, specifically IMO, typically of less than 10-18 degrees of polymerization comprised of α-(1→6) linkages and terminated by an α-(1→4) glucosyl linkage. The α-(1→4) terminal group originates from maltose. Therefore, maltosyl-isomaltooligosaccharide or MIMO is produced by an acceptor reaction by maltose or other maltooligosaccharide. An example of an MIMO with a single maltosyl linkage [—O-α-(1,4)-] at the reducing end, and accordant with the panose core structure, is maltosyl-isomaltotriose, which has the following chemical structure:

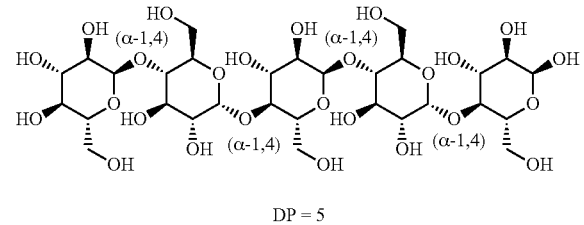 [SMILES: OC[C@H]1O[C@H](O[C@H]2[C@H](O)[C@@H](O)[C@@H](O[C@H]3[C@H](O)[C@@H](O)[C@@H](O[C@H]4[C@H](O)[C@@H](O)[C@@H](O[C@H]5[C@H](O)[C@@H](O)[C@@H](O)O[C@@H]5CO)O[C@@H]4CO)O[C@@H]3CO)O[C@@H]2CO)[C@H](O)[C@@H](O)[C@@H]1O]

DP = 5

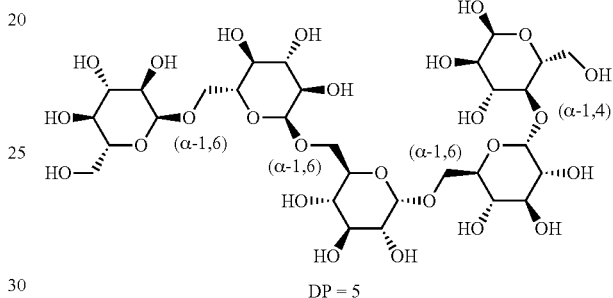

DP = 5

"Isomaltooligosaccharide", or "IMO", refers to glucosyl saccharides with a core structure based on an α-(1→6) linked backbone that may include α-(1→4), α-(1→33) (nigerooligosaccharides or kojioligosaccharides), and/or α-(1→4) (maltooligosaccharide)-linked branches. IMO is a GlcOS assembled with a core of [—O-α-(1,6)-] linkages, accordant with the dextran core structure. One example is isomaltopentaose, which has the following chemical structure:

"Branched MIMO" refers to an oligosaccharide, specifically MIMO, of less than or equal to 10 degrees of polymerization comprised of α-(1→6) linkages terminated by an α-(1,4) glucosyl linkage and α-(1,2), α-(1,3) and/or α-(1,4) branches. Examples of a branched MIMO with glucose branching linkages at positions 1,2 and 1,3 and/or 1,4 have the following structures:

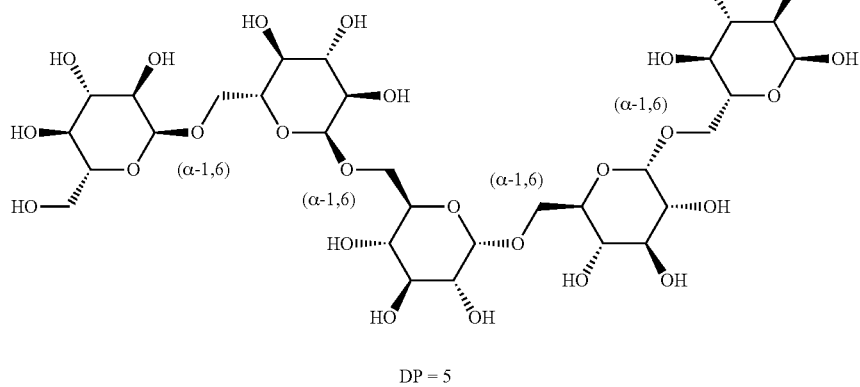

DP = 5

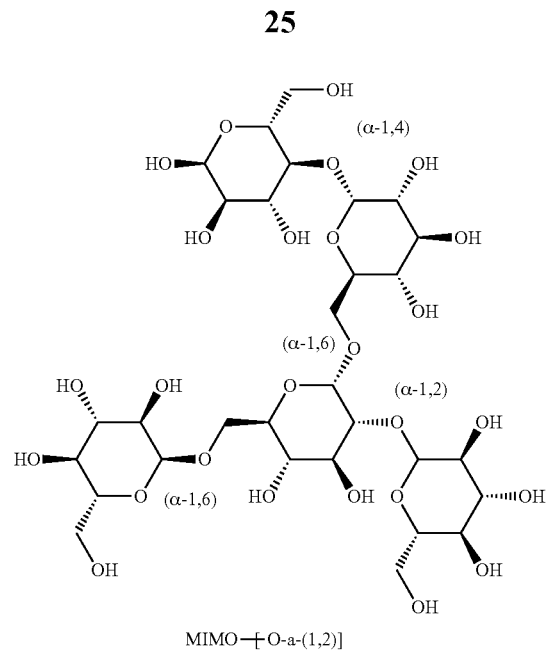

MIMO—[O-a-(1,2)]

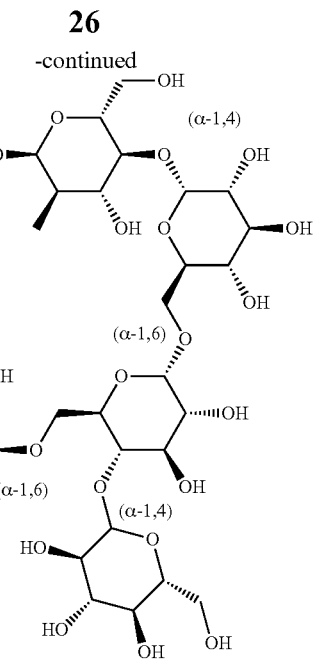

MIMO—[O-a-(1,4)]

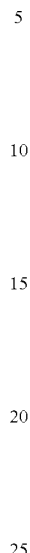

MIMO—[O-a-(1,3)]

"Dietary supplement" refers to a food, food ingredient, or food additive that produces a health benefit. Carbohydrates such as oligosaccharides can be dietary supplements.

"SAC" means a Strong Acid Cation exchange resin, typically one with sulfonic acid groups, i.e., a sulfuric acid equivalent. In some instances, SAC is referring to Purolite C-150S, which has a $H^+$ capacity of 1.8 mol/L.

"WBA" means a Weak Base Anion exchange resin, typically one with tertiary amine groups, which are not stronger than the corresponding free base (pKa~9.8). In this case, WBA is referring to Purolite A-133 which has a free-base capacity of 1.8 mol/L.

The Examples illustrate some of the experimental work performed in the development of the invention.

Example 1

Two variations of product were used in clinical trials. They varied only in molecular weight distribution, and this was controlled by varying the sucrose to maltose ratio (S/M). "A2"-type products have a molecular weight of about 750 Da and "Classic" or "NC"-type products have a molecular weight of about 800 Da. Each of the two types were a composite of six 16 kg fermentations each of A2 and NC types (12 total fermentations). The clinical trials were both double-blind placebo controlled studies, and the parameters for each are given here.

Clinical Trial Protocol

Purpose:

To compare the effects of daily intake of two different formulations of the ISOThrive supplement vs. a placebo on the primary outcome measure of body weight and secondary outcome measures (inflammatory and satiety serum markers, hunger/satiety, health-related measures and self-reported quality of life) in a group of overweight but otherwise healthy adults.

Study Design:

A randomized, placebo controlled, double-blind parallel design control trial to compare the effects of daily intake for a 3-month period of the ISOThrive supplement vs. a placebo.

The study design included 3 treatment arms:
(1) ISOThrive supplement (Type 1, "A2")
(2) ISOThrive supplement (Type 2, "NC")
(3) Placebo supplement (high-maltose syrup at 64 brix)

The two ISOThrive supplements (Type I and 2) have the same active ingredients, and a dosage of 1000 mg of MIMO. The two types of the supplement differ in terms of purity (MIMO/total) and the mass-average molecular weight distribution of the MIMO, which is the principal ingredient. Study participants included 105 overweight men and women in the age range of 18 to 75 years, who are nonsmokers with a body mass index (BMI) > or =25 and a maximum body weight of 350 pounds Another Trial Protocol Purpose:

First, to evaluate, via 16S rRNA sequencing of fecal swabs, the effect of a nutritional supplement (specific soluble fiber known as isomalto-oligosaccharides) on the abundance, diversity, and predicted microbiome gene function, of gut bacteria. Second, to evaluate the overall subject condition in terms of body weight, and self-reported gut health data. The test groups were compared across-supplement and with the placebo group.

Study Design:

a randomized, placebo-controlled trial, with a dose escalation at the mid-point of the intervention period.

Subjects were between the ages of 18 and 45 years, with a maximum weight of 350 lbs., and a body mass index 25 kg/m² or higher, and have general self-reported good health.

60 subjects were randomized to three arms (20 each: Supplement type-1, Supplement formula type-2, or placebo) took a daily dose of either Supplement A, Supplement B, or placebo for 8 weeks.

Doses included 500 mg of MIMO during the first 4 weeks and then included 1000 mg of MIMO for a second 4 weeks.

Composition for Clinical Trials: "A2" and "Classic" Type Products

Six fermentations were carried out to generate each type of product using a 20 L fermenter (New Brunswick BioFlo 410), that was charged with the following medium:

about 16 hr. The balance of the medium was transferred to the fermenter via sanitary pump. The fermenter was sealed and sterilized in place (SIP) to 116° C., then rapidly cooled to 30° C. (see temperature curve in FIG. 8). The curve was modeled, and the model was used to determine the time spent in each microbiologically relevant regime. The results were as follows:

| T ° C.: | Hr: |
|---|---|
| >70 | 2.43 |
| >80 | 2.22 |
| >90 | 1.86 |
| >100 | 1.16 |
| >110 | 0.46 |

These results are relevant because when the full media is mixed and adjusted to pH 7.00 (to avoid inversion of sucrose) significant amounts of maltose (a reducing sugar) are lost via the Maillard reaction. In addition to generating a great deal of colored material (>10,000 IU), this increases the S/M of the medium (as detected by HPLC-RID), and has the effect of increasing the ultimate molecular weight distribution of the product.

The fermenter was inoculated with 150 mL of the flask seed culture containing *Leuconostoc citreum* ATCC 13146 (NRRL B-742) and the pH of the medium was corrected to 6.50 using a solution of 37% HCl. The fermentation was allowed to proceed for 55 Hr with pH adjustment using a solution of 40% NaOH to maintain the pH at 5.50.

Typically, there is a 4-6 hour induction period, or lag-phase, preceding log-growth. The log-growth phase is about 10 hours (where most growth occurs) but it typically takes about 18 hours to reach stationary growth. pH 5.5 is typically achieved within about 2 hours of log-phase growth, and this pH is maintained thereafter. This pH was chosen per the experimentally determined pH optimum for the dextran-sucrase enzyme.

The fermentations consumed 450±29.3 and 468±22.3 g 40% NaOH for the A2 and NC type batches, respectively.

| "A2" Type | | | | "Classic" Type | | | |
|---|---|---|---|---|---|---|---|
| N = 6 | Kg: | Stdev: | RSD, %: | N = 6 | Kg: | Stdev: | RSD, %: |
| Water | 12.594 | 0.0144 | 0.114 | Water | 12.600 | 0.0004 | 0.003 |
| Sucrose | 1.800 | 0.0000 | 0.000 | Sucrose | 1.910 | 0.0004 | 0.021 |
| Maltose-H$_2$O | 0.998 | 0.0000 | 0.000 | Maltose-H$_2$O | 0.864 | 0.0000 | 0.000 |
| MnSO$_4$-H$_2$O | 0.0002 | 0.0000 | 1.000 | MnSO$_4$-H$_2$O | 0.0002 | 0.0000 | 1.610 |
| MgSO$_4$ | 0.0015 | 0.0000 | 0.209 | MgSO$_4$ | 0.0015 | 0.0000 | 0.281 |
| FeSO$_4$-7H$_2$O | 0.0002 | 0.0000 | 1.454 | FeSO$_4$-7H$_2$O | 0.0002 | 0.0000 | 0.801 |
| KH$_2$PO$_4$ | 0.0400 | 0.0000 | 0.014 | KH$_2$PO$_4$ | 0.0400 | 0.0000 | 0.076 |
| NaCl | 0.0002 | 0.0000 | 0.824 | NaCl | 0.0002 | 0.0000 | 1.058 |
| CaCl$_2$-2H$_2$O | 0.0008 | 0.0000 | 0.390 | CaCl$_2$-2H$_2$O | 0.001 | 0.0000 | 1.479 |
| Yeast Extract | 0.075 | 0.0004 | 0.543 | Yeast Extract | 0.076 | 0.0008 | 1.108 |
| NaOH, 50% | 0.016 | 0.0003 | 2.056 | NaOH, 50% | 0.016 | 0.0007 | 4.379 |
| Total: | 15.53 | 0.040 | 0.25 | Total: | 15.51 | 0.0232 | 0.15 |
| TS, %; | 17.38 | 0.042 | 0.24 | TS, %; | 17.33 | 0.0259 | 0.15 |
| Brix, %: | 18.19 | 0.031 | 0.17 | Brix, %: | 18.15 | 0.0313 | 0.17 |
| S/M: | 2.00 | 0.000 | 0.00 | S/M: | 2.45 | 0.0005 | 0.02 |

The pH of the medium was adjusted to 7.00 with NaOH (50%).

Figure 9:
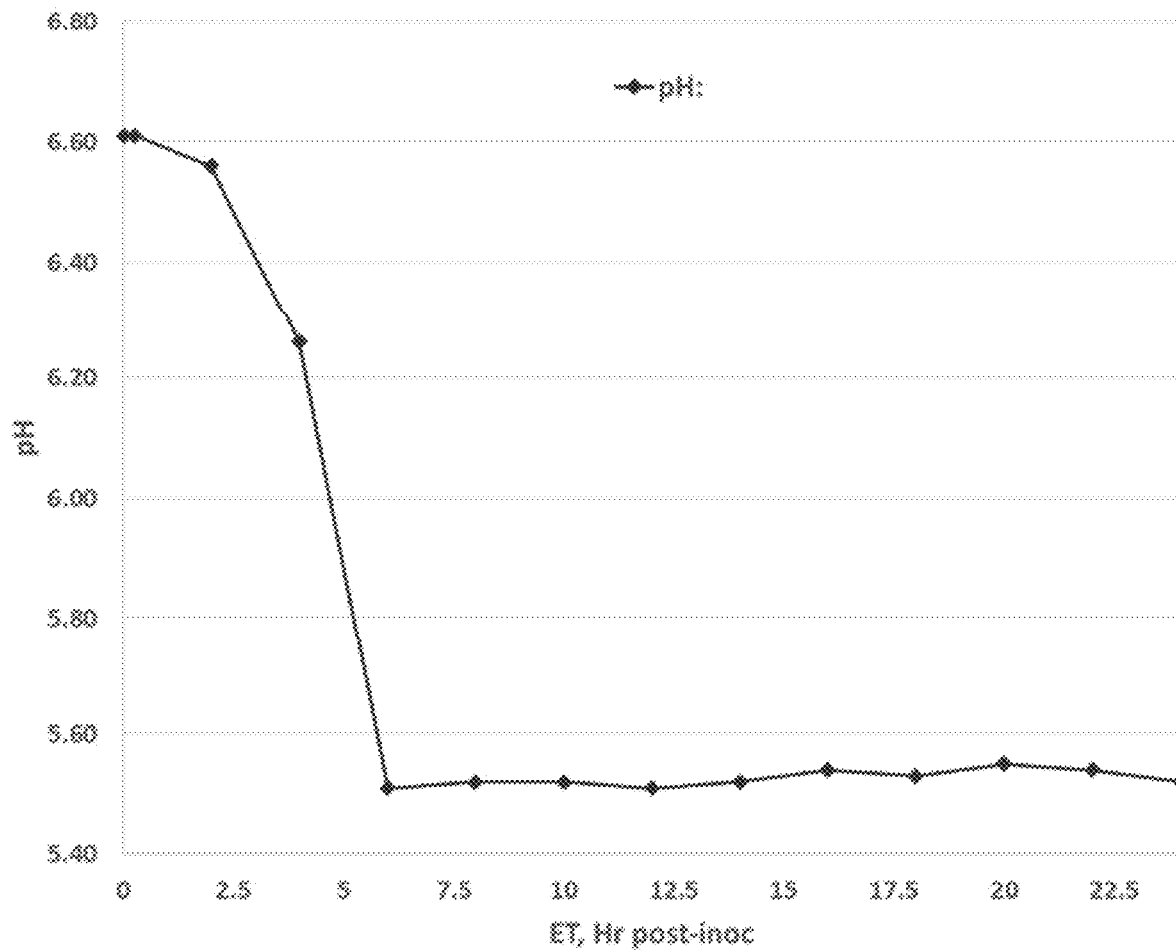
FIG. 9 shows the behavior of fermentation pH during the course of a 14 L fermentation with *Leuconostoc citreum* ATCC 13146, the designation NRRL B-742. Note onset of pH control with NaOH (40% w/w) to maintain a pH of 5.50 at approximately 6 hours into log-growth phase.

200 mL of the medium was transferred to an Erlenmeyer flask, sealed and autoclaved at 121° C. for 15 minutes, cooled, and inoculated with 1 mL vial stock (0.5 mL late-log culture in 20% glycerol, stored at −75° C.). The seed was incubated with swirling at 27° C. and allowed to grow for FIG. 9 graphically illustrates the typical behavior of the pH during fermentation after inoculation.

Figure 10:
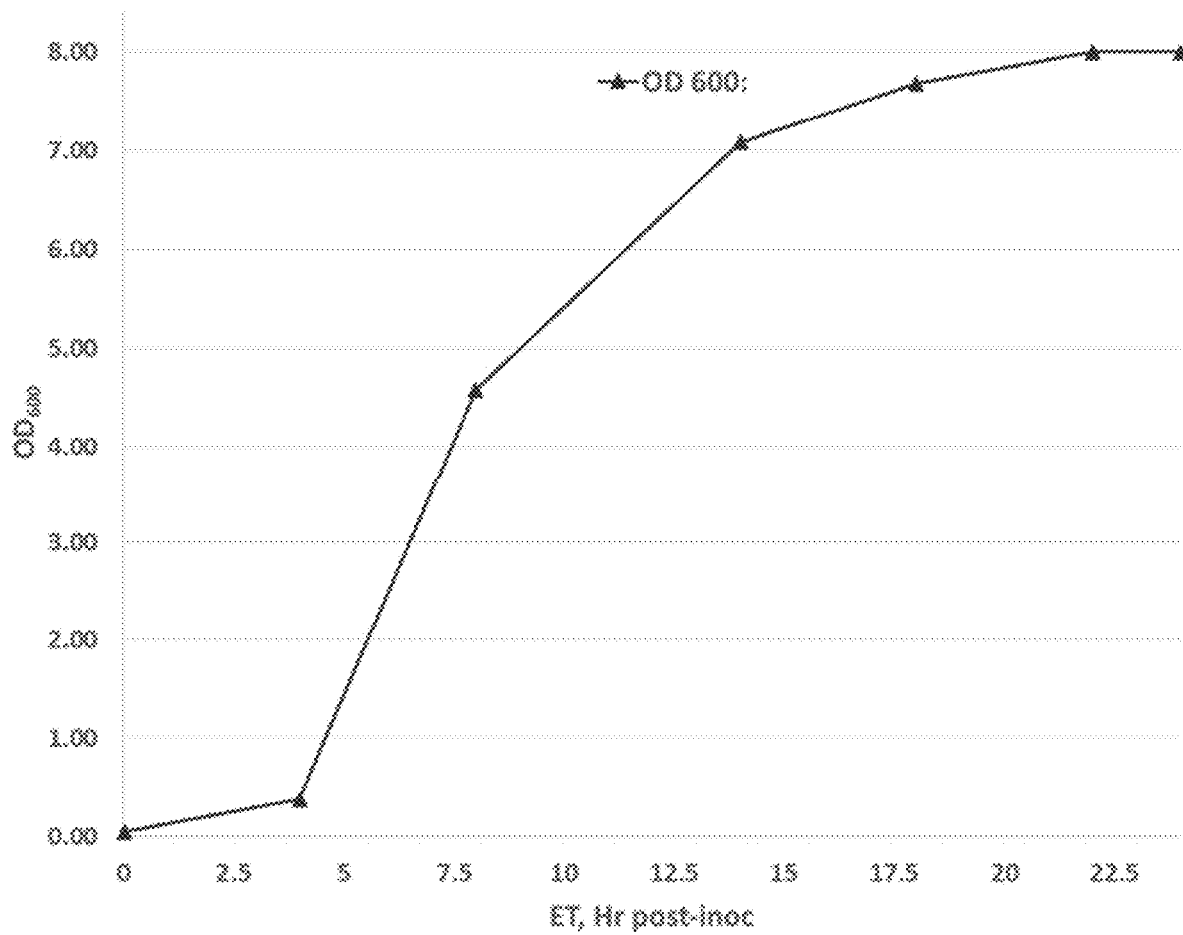
FIG. 10 shows the progress of fermentation via optical density (OD) through log-phase growth of a 14 L fermentation with *L. citreum* NRRL B-742.
Figure 11:
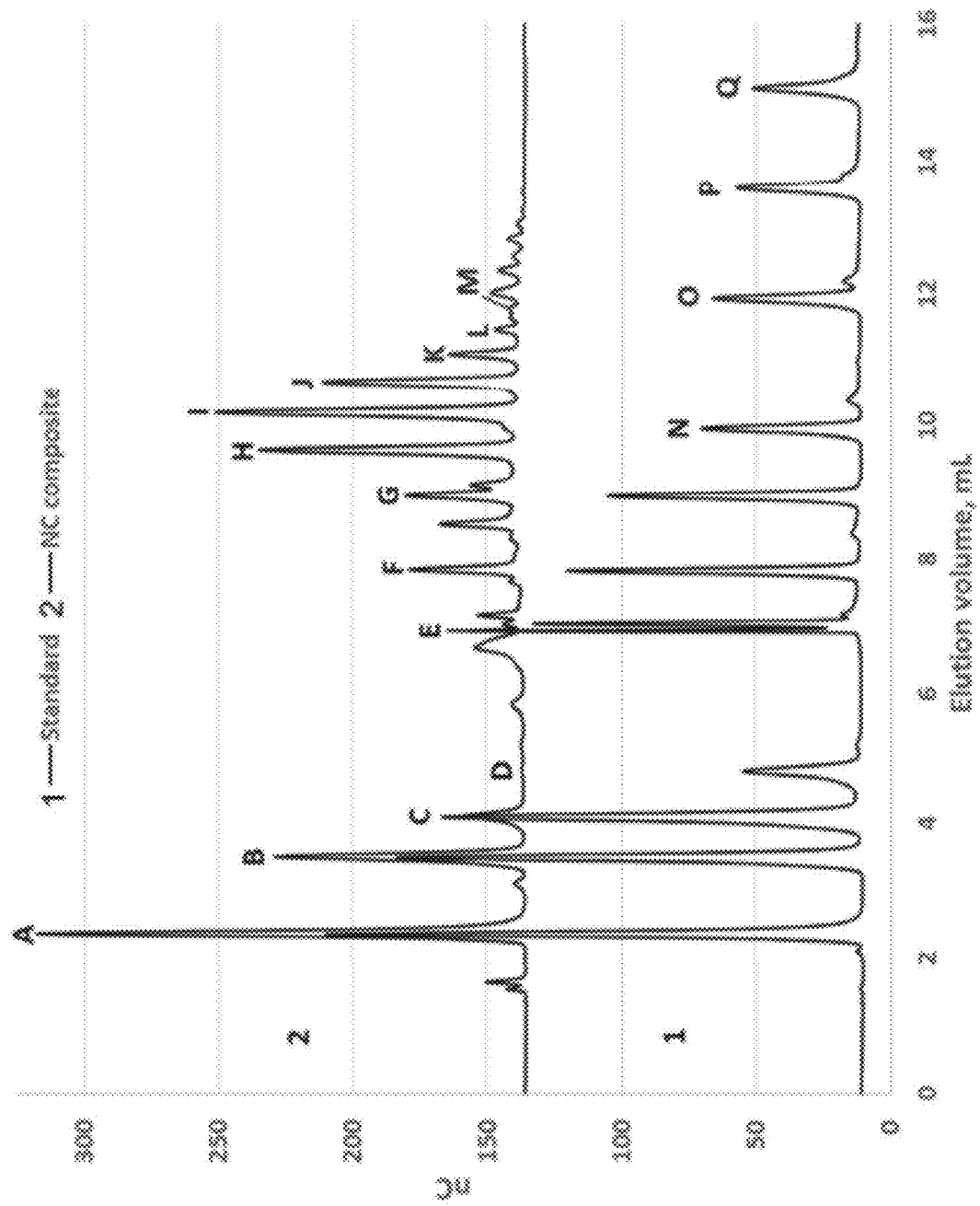
FIG. 11 shows HPAEC-PAD chromatograms of (1) a mixture of standards; and (2) the New Classic (NC) composite product described in Example 1, wherein the components are A: D-mannitol; B: L-arabinose (internal standard); C: D-glucose; D: D-fructose; E: sucrose; F: maltose; G-M refer to MIMO DP 3-9, respectively; and N-Q refer to maltooligosaccharides [α-(1,4)] DP 3-6, respectively.
Figure 12:
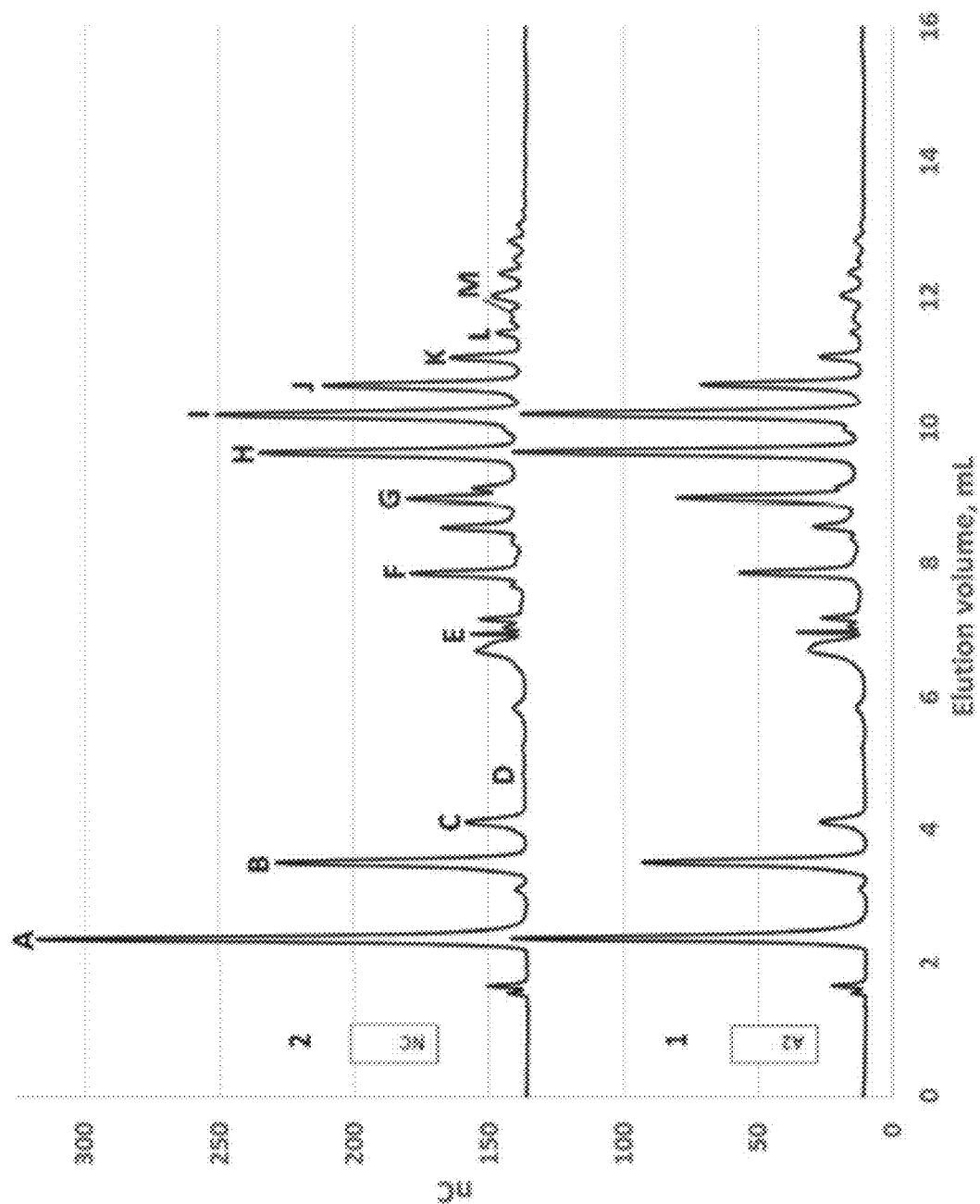
FIG. 12 shows HPAEC-PAD chromatograms of the (1) A2, and, (2) NC composite products wherein the components are A: D-mannitol; B: L-arabinose (internal standard); C: D-glucose; D: D-fructose; E: sucrose; F: maltose, G-M refer to MIMO DP 3-9, respectively. Note larger relative peak areas for DP>4 in the NC composite product.
Figure 13:
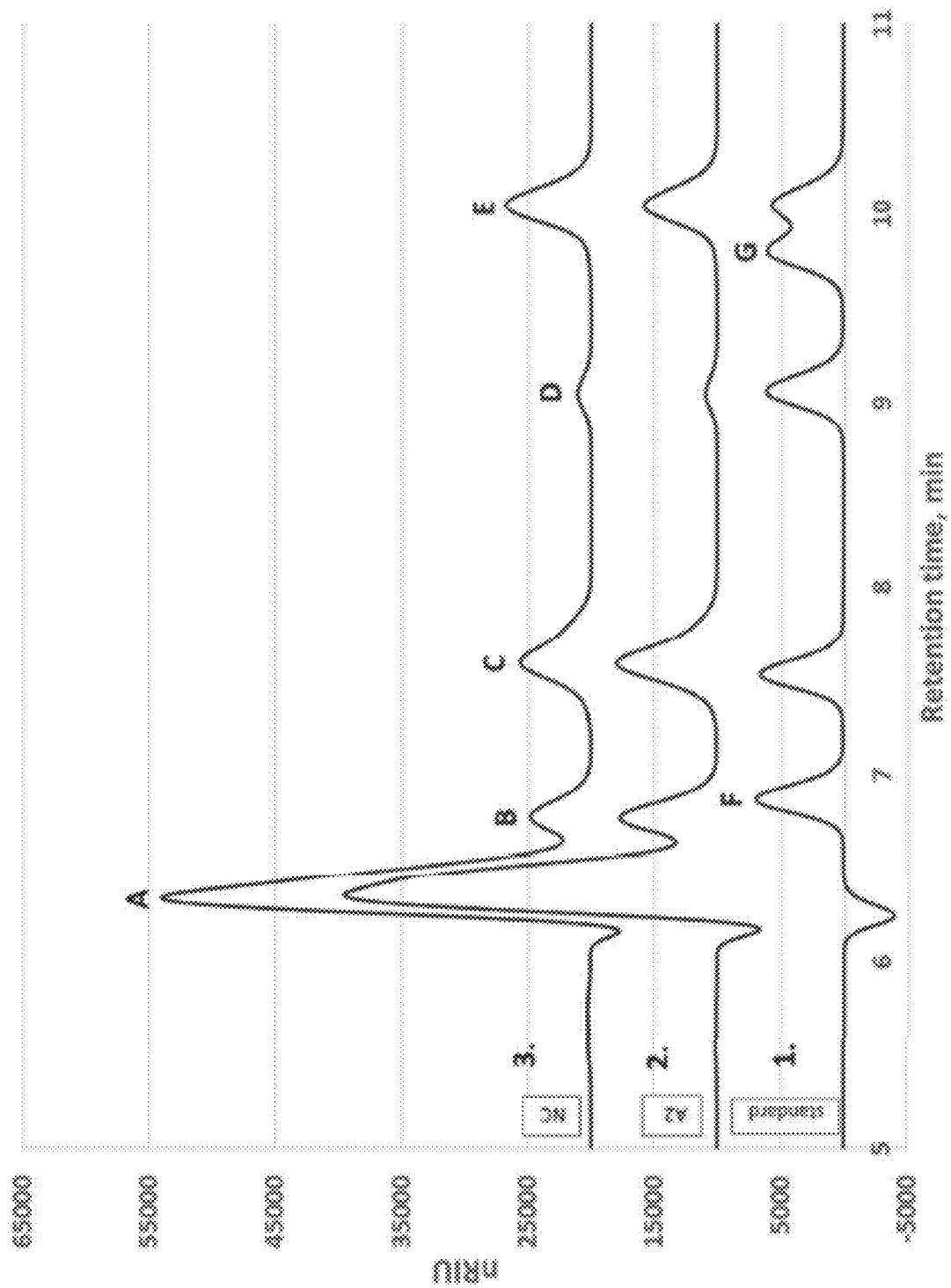
FIG. 13 shows the carbohydrate components, via high pressure liquid chromatography-refractive index detection (HPLC-RID) of (1) Standard mixture; (2) A2; and (3) NC composite products wherein the components are A: MIMO DP>3; B: MIMO DP 3; C: maltose; D: D-glucose; E: D-mannitol; F: maltotriose; and, G: D-fructose.
Figure 14:
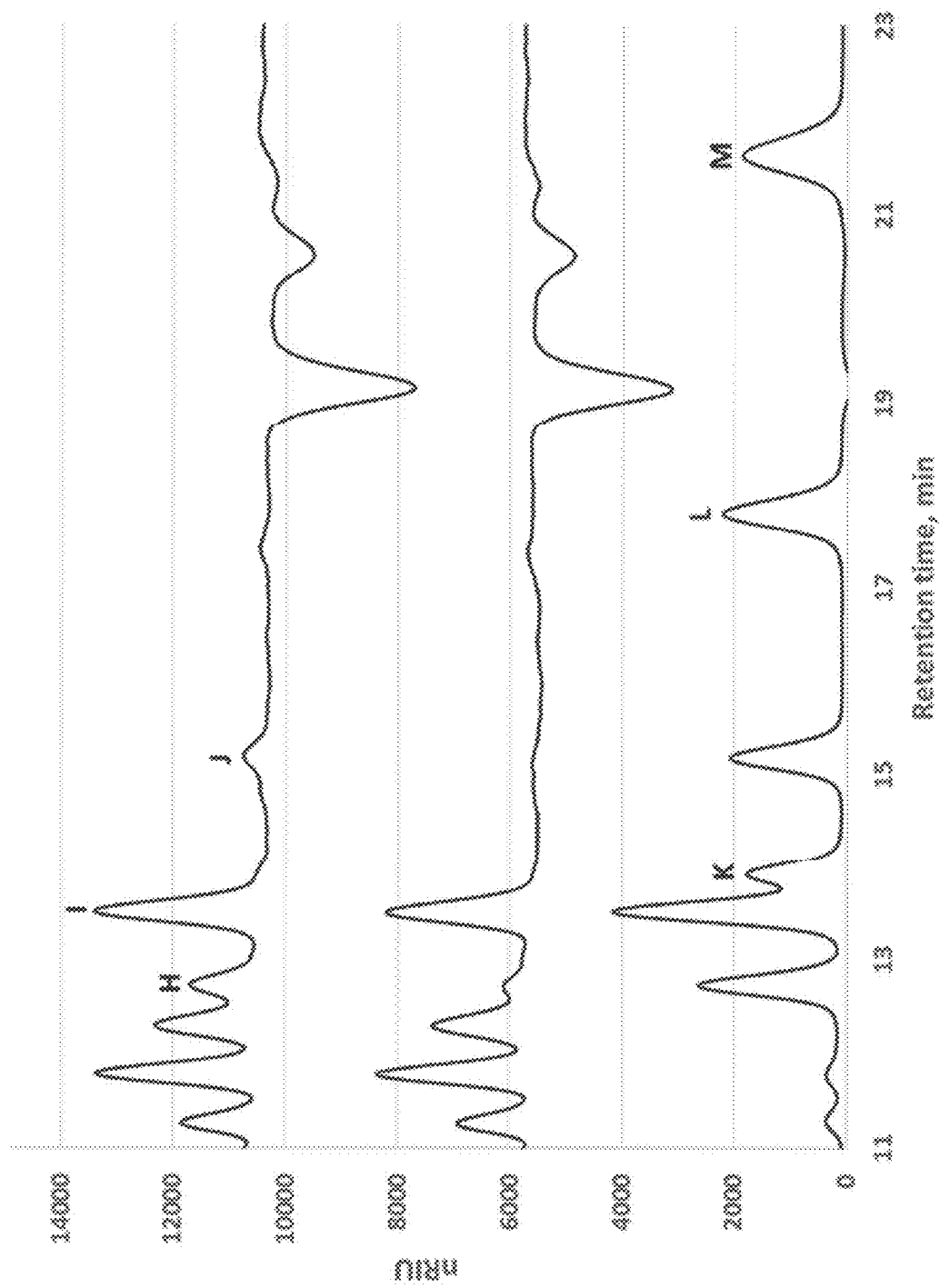
FIG. 14 shows the second half of the HPLC-RID overlay shown in FIG. 13 magnified by a factor of about 10, of (1) Standard mixture; (2) A2; and (3) NC composite products wherein the components are H: lactic acid; I: glycerol; J: acetic acid; K: formic acid; L: propionic acid; and M: isobutyric acid.
Figure 15:
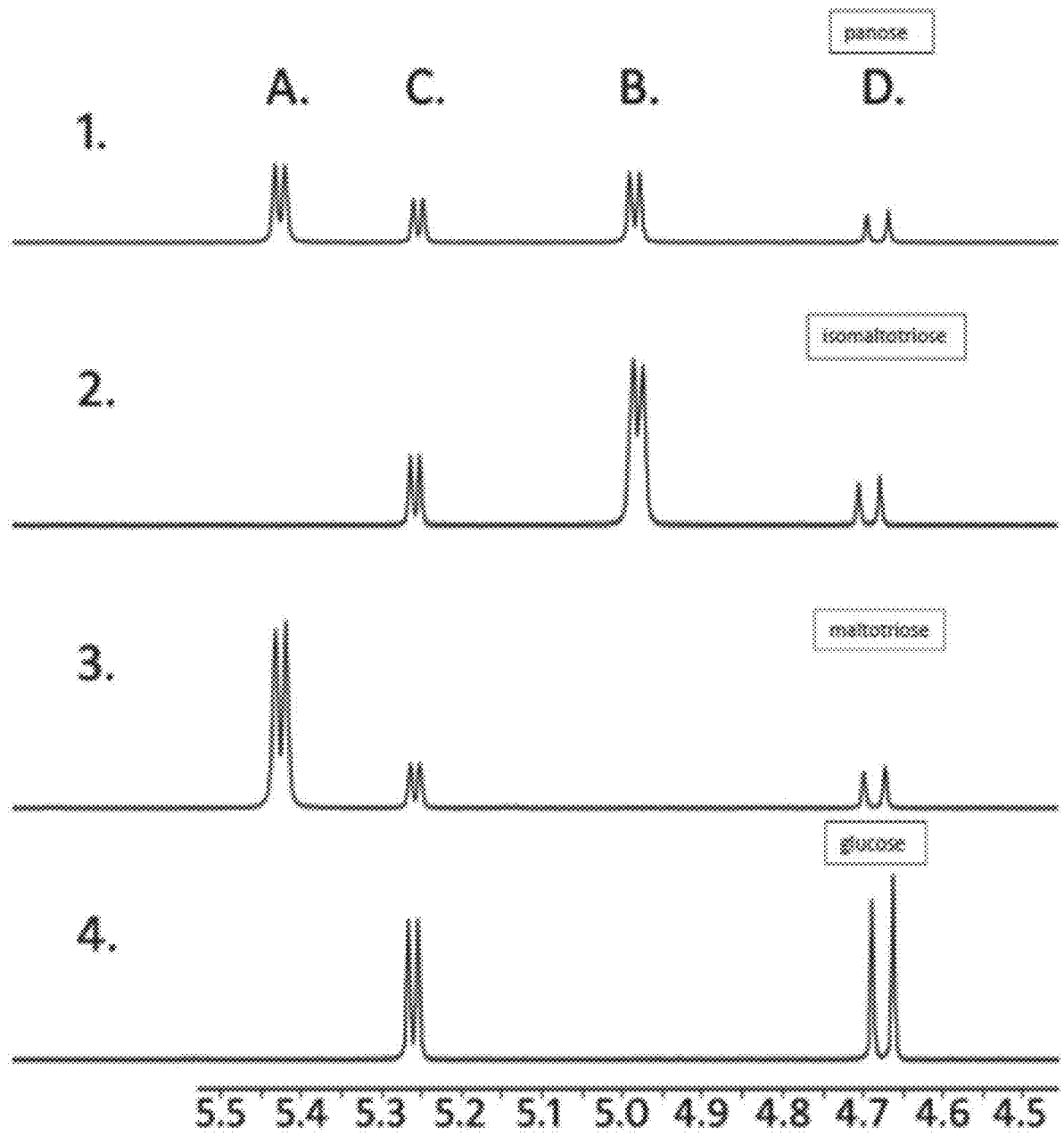
FIG. 15 shows an overlay of 1D 300 MHz $^1$H NMR (water suppressed in $D_2O$) spectra of chemical shift reference materials including (1) D-panose (MIMO-DP3); (2) isomaltotriose; (3) maltotriose; and (4) D-glucose, anomerically equilibrated, wherein signal A corresponds to α-(1,4) anomeric protons; B corresponds to α-(1,6) anomeric protons; and C, D correspond to the α and β anomeric protons, respectively, at the reducing end.
Figure 16:
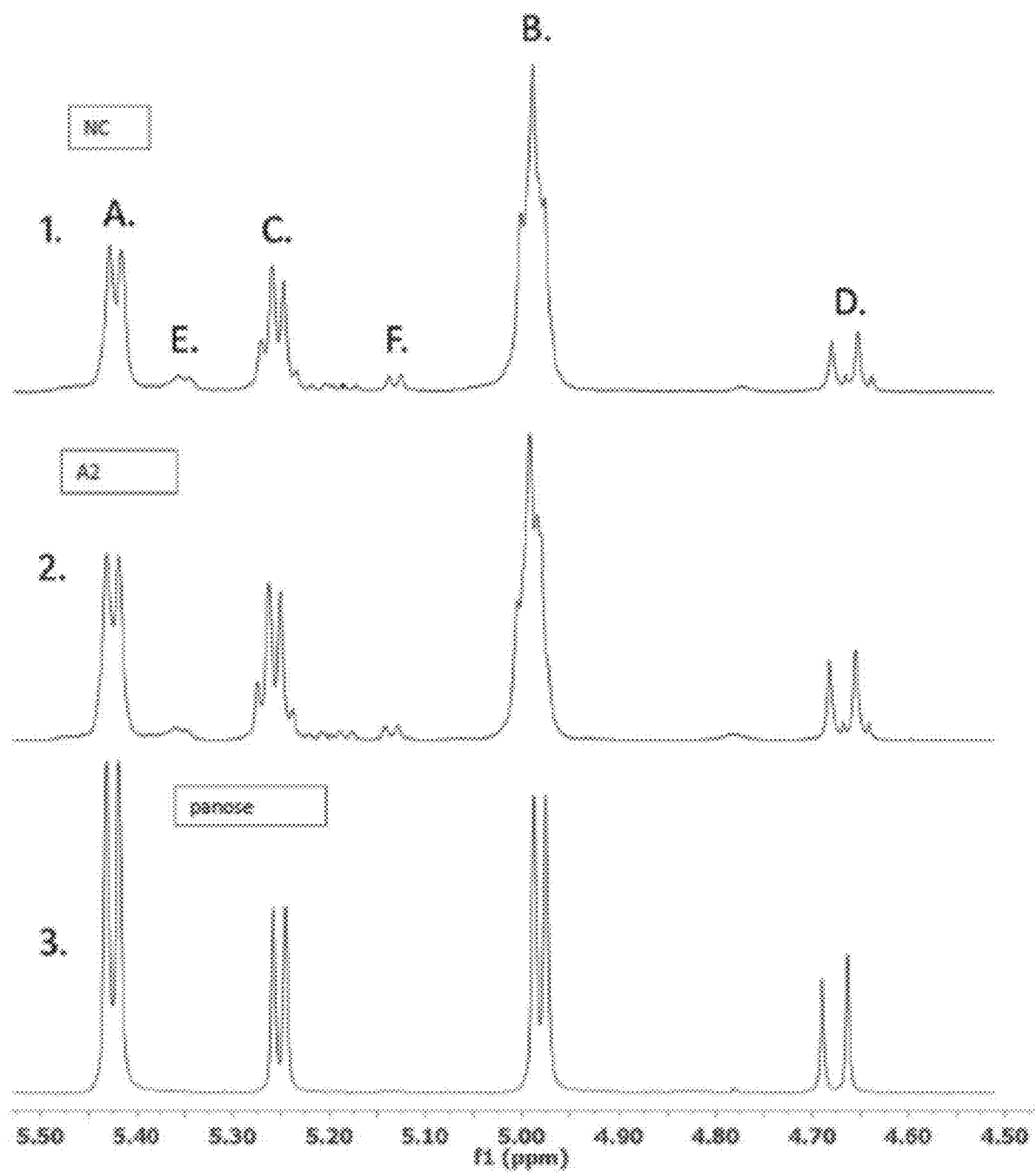
FIG. 16 shows an overlay of 1D 300 MHz $^1$H NMR (water suppressed in $D_2O$) spectra of the anomeric regions of 1 and 2, NC and A2 composite products, respectively and, 3, D-panose (δ reference) wherein signal A corresponds to α-(1,4) anomeric protons; signal B corresponds to α-(1,6) anomeric protons; signals C and D correspond to the α and β anomeric protons, respectively, at the reducing end; and signals E and F correspond to the α-(1,3) and α-(1,2) anomeric protons, respectively.
Figure 17:
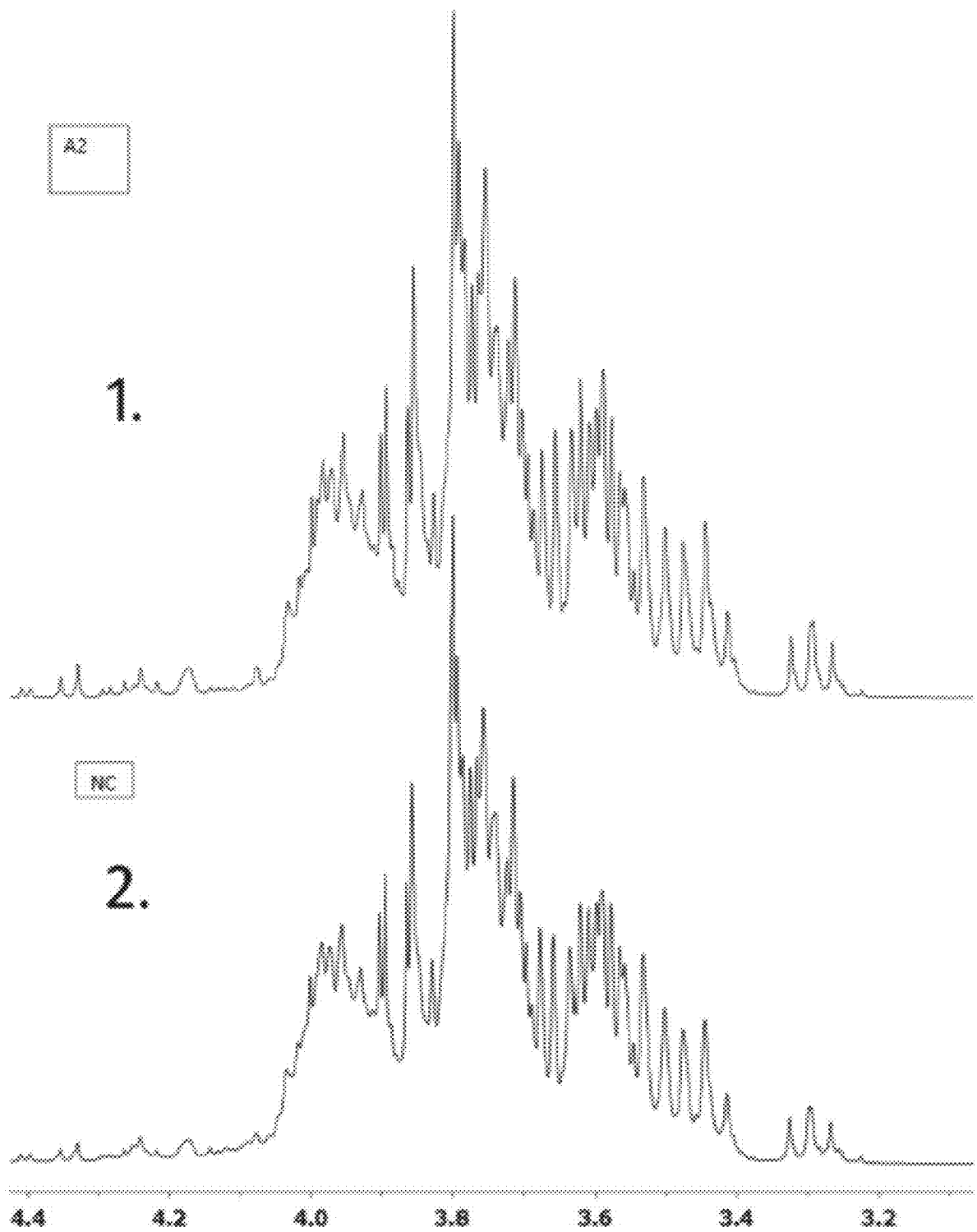
FIG. 17 shows an overlay of 1D 300 MHz $^1$H NMR (water suppressed in $D_2O$) spectra of the non-anomeric regions of (1) A2 and (2) NC composite products.
Figure 18:
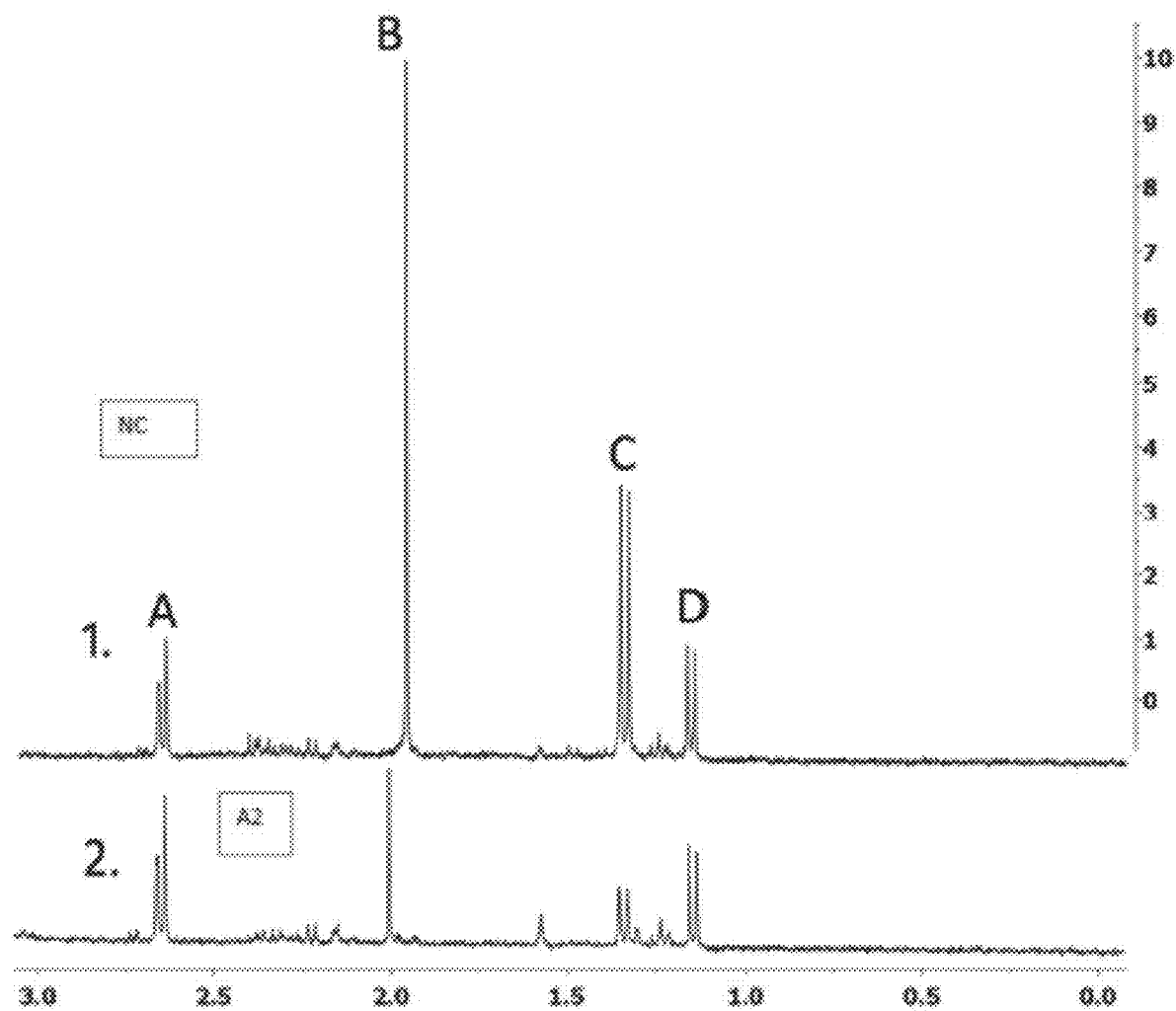
FIG. 18 shows an overlay of 1D 300 MHz $^1$H NMR (water suppressed in $D_2O$) spectra of the alkyl regions of (1) NC and (2) A2 composite products wherein signal A is unknown, B corresponds to acetyl protons (the difference is due to pH, A2=pH 4.81, NC=pH 6.57), C corresponds to lactate C3 methyl protons; and D is unassigned. Note, the amount of acetate/lactate in 2 (A2) was below the minimum detection limit via HPLC-RID and barely detectable in the NC composite material.

The growth curve (onset and log-phase) was determined by optical density at 600 nm (OD$_{600}$), and is shown in FIG. 10.

The completion of fermentation was indicated by consumption of fructose, which was converted to mannitol, and by cessation of the take up of alkali. Upon completion, the fermentation was harvested, and the cells removed via centrifugation (Sorvall RC-5B Plus, G3 rotor, 13,689 g for 20 min at 5-10° C.). The broth was concentrated by evaporation (Buchi R-20 rotavap, 70° C. bath, 54° C. vapor @ 26" Hg) to 40 brix, and decolorized by treatment with 250 g of Carbochem CA-50S powdered activated carbon (PAC) while still hot (50-65° C.). The slurry was stirred for 20 minutes and vacuum-filtered (using a 2×240 mm Buchner funnel, 2 L side-arm flask, Whatman #3 filter papers and a 100 g Celite 545 pre-coat). The powdered activated carbon cakes were washed with 3×250 mL water each, and the whole wash was collected.

The minerals/salts (primarily sodium) and organic acid metabolites (primarily lactic and acetic acids) were removed in a sequential two-stage ion exchange process. First, the decolorized concentrate, typically 6-7 kg at 32-36° bx, is passed through 6.8 L strong acid cation exchange resin (Purolite C-150S) to remove the minerals/salts. Then, the de-ashed broth is passed through 14.7 L weak base anion exchange resin (Purolite A-133) to remove the organic acids. The de-ashed liquor I s then concentrated by evaporation to 56.78 brix.

The liquor (about 56 brix) is transferred hot into a 2.5 gal crystallization vessel and allowed to slowly cool to room temperature (19-22° C.) and crystallize overnight.

The resulting mixture is homogenized to yield a pourable crystal slurry. The mannitol crystals can be separated out via basket centrifuge (Robitel RA 20 VX with a 10 μm polypropylene filter bag).

A small portion of the crystal cake (0.320 kg at 95% solids, cake #1) can be washed with 500 mL ice-cold deionized water, and a 0.697 kg cake wash (wash #1) at 20.5 brix can be retained for recycle while a 2.626 kg liquor (liquor #1) at 51.70 brix can be refrigerated to 3° C. to crystallize overnight.

Another portion of the crystals (cake #2, 0.109 kg at 95% solids) can be removed, and washed as before. The cake wash #2 can be combined with wash #1 for recycle. The product liquor #2 at 49.0 brix can be analyzed (HPAEC-PAD, HPLC-RID, brix, pH and conductivity) and refrigerated pending compositing with like (either A2 or Classic) batches. Once combined the whole composite can be evaporated to 65-67 brix prior to analytics for the final certificate of analysis and pack out into trial dosage forms. The packaging is performed in a sterilized laminar flow-hood where 32 g amounts (for example) can be packed by volume (24.16 mL), as confirmed by lot mass, in autoclaved CRGXTA-1 oz amber glass ovals (Berry Plastics Corporation) with autoclaved 20 mm SealSafe Penetrex adapter-plug seals for dose metering via luer-tip plastic syringe (Andwin Scientific, #760020G).

Analytical Results and Reproducibility

A2 Type Product:

| Batch--> | 021815 | 022315 | 022615 | 030215 | 033015 | 040915 | A2 Comp. |
|---|---|---|---|---|---|---|---|
| S/M: | 2.00 | 2.00 | 2.00 | 2.00 | 2.00 | 2.00 | 2.00 |
| DP 1, %/bx: | 2.60 | 1.26 | 1.67 | 1.36 | 0.59 | 1.80 | 1.51 |
| DP 2, %/bx: | 6.48 | 2.92 | 2.71 | 9.46 | 5.35 | 8.17 | 6.54 |
| MIMO, %/bx: | 74.89 | 77.57 | 76.02 | 80.00 | 73.94 | 71.94 | 76.53 |
| Mannitol, %/bx: | 11.17 | 10.59 | 10.87 | 10.03 | 11.08 | 12.11 | 10.42 |
| Lactate, %/bx: | 0.00 | 0.00 | 0.12 | 0.00 | 0.26 | 0.00 | 0.00 |
| Formate, %/bx: | 0.00 | 0.00 | 0.00 | 0.00 | 0.00 | 0.00 | 0.00 |
| Acetate, %/bx | 0.00 | 0.00 | 0.06 | 0.00 | 0.10 | 0.00 | 0.00 |
| Glycerol, %/bx: | 1.48 | 1.44 | 1.60 | 1.55 | 1.39 | 1.45 | 1.47 |
| TOTAL, %/bx: | 96.62 | 93.78 | 93.05 | 102.41 | 92.71 | 95.48 | 96.48 |
| PURITY: | 77.51 | 82.71 | 81.70 | 78.12 | 79.75 | 75.35 | 79.33 |
| MWD, Da: | 746.89 | 758.02 | 777.60 | 748.74 | 762.34 | 746.75 | 760.37 |
| Brix, %: | 50.51 | 49.00 | 53.76 | 54.93 | 51.32 | 47.39 | 67.27 |
| μS/cm: | 10.53 | 12.8 | 15.65 | 15.19 | 2260 | 364 | 260 |
| pH: | 4.9 | 4.59 | 3.45 | 5.28 | 5.82 | 6.91 | 4.47 |

"New Classic" or "NC"-Type Product

| Batch--> | 012015 | 031015 | 032015 | 032315 | 032515 | 040215 | NC Comp |
|---|---|---|---|---|---|---|---|
| S/M: | 2.33 | 2.33 | 2.33 | 2.33 | 2.33 | 2.33 | 2.33 |
| DP1, %/bx: | 2.73 | 2.08 | 1.10 | 1.14 | 1.87 | 1.38 | 1.95 |
| DP 2, %/bx: | 5.54 | 6.96 | 5.93 | 1.96 | 5.47 | 5.06 | 1.73 |
| MIMO, %/bx: | 71.88 | 71.22 | 73.63 | 74.59 | 69.79 | 76.19 | 72.61 |
| Mannitol, %/bx: | 13.25 | 10.94 | 10.83 | 12.36 | 12.27 | 10.63 | 11.97 |
| Lactate, %/bx: | 0.000 | 0.000 | 0.000 | 0.000 | 0.969 | 0.20 | 0.30 |
| Formate, %/bx: | 0.000 | 0.000 | 0.000 | 0.000 | 0.405 | 0.00 | 0.27 |
| Acetate, %/bx | 0.033 | 0.000 | 0.000 | 0.000 | 0.364 | 0.05 | 0.12 |
| Glycerol, %/bx: | 1.558 | 2.269 | 1.562 | 1.562 | 1.990 | 1.58 | 1.76 |
| TOTAL, %/bx: | 94.99 | 93.47 | 93.04 | 91.61 | 93.13 | 95.10 | 90.72 |
| PURITY: | 75.68 | 76.20 | 79.13 | 81.42 | 74.94 | 80.12 | 80.05 |
| MWD, Da: | 817.69 | 808.88 | 804.03 | 820.12 | 811.74 | 806.52 | 834.69 |
| Brix, %: | 49.06 | 52.16 | 46.44 | 50.08 | 51.23 | 50.54 | 65.07 |
| μS/cm: | 239 | 279 | 43.2 | 350 | 2070 | 1415 | 410 |
| pH: | 6.82 | 6.43 | 6.69 | 7.13 | 6.83 | 6.94 | 5.12 |

Where DP 1=glucose+fructose and DP 2=sucrose+maltose:

| A2, %/brix | 021815DA | 022315DA | 022615DA | 030215DA | 033015DA | 040915DA | A2 Comp. |
|---|---|---|---|---|---|---|---|
| Glucose | 2.27 | 1.11 | 1.46 | 1.26 | 0.56 | 1.69 | 1.41 |
| Fructose | 0.32 | 0.15 | 0.21 | 0.10 | 0.03 | 0.12 | 0.10 |
| Sucrose | 0.71 | 0.69 | 0.90 | 3.81 | 0.68 | 1.34 | 0.87 |
| Maltose | 5.77 | 2.23 | 1.82 | 5.65 | 4.67 | 6.83 | 5.68 |

| NC, %/brix | 012015DA | 031015DA | 032015DA | 032315DA | 032515DA | 040215DA | NC Comp |
|---|---|---|---|---|---|---|---|
| Glucose | 2.42 | 1.94 | 1.05 | 0.99 | 1.79 | 1.36 | 1.67 |
| Fructose | 0.30 | 0.14 | 0.04 | 0.15 | 0.09 | 0.02 | 0.27 |
| Sucrose | 0.75 | 1.52 | 1.25 | 0.27 | 1.09 | 0.70 | 0.36 |
| Maltose | 4.79 | 5.44 | 4.68 | 1.69 | 4.38 | 4.36 | 1.37 |

Comparative chromatograms (HPAEC-PAD) and 300 MHz 1H NMR for the two composite products are provided in FIGS. 11 through 18.

The MIMO of these products had a reproducible distribution of DPs from 3-9 that varied according to S/M present at the start of fermentation:

| N = 6 each | A2, mean: | STDEV: | RSD, %: | NC, mean: | STDEV: | RSD, %: |
|---|---|---|---|---|---|---|
| MIMO-DP3 | 12.522 | 1.003 | 8.007 | 8.88 | 0.50 | 5.61 |
| MIMO-DP4 | 23.510 | 1.173 | 4.991 | 17.46 | 1.00 | 5.75 |
| MIMO-DP5 | 23.357 | 0.685 | 2.931 | 22.59 | 1.38 | 6.12 |
| MIMO-DP6 | 10.888 | 0.423 | 3.883 | 13.73 | 0.28 | 2.06 |
| MIMO-DP7 | 3.280 | 0.181 | 5.515 | 5.09 | 0.38 | 7.52 |
| MIMO-DP8 | 2.251 | 0.229 | 10.167 | 3.96 | 0.41 | 10.35 |
| MIMO-DP9 | 0.683 | 0.047 | 6.933 | 1.14 | 0.17 | 14.53 |

Example 2

After performing the processes described in Example #1, it was observed that mannitol would crystallize from the final products upon refrigeration or long-term storage at cooler room temperature. This example illustrates the variability in product composition relative to the crystallization process employed. Additionally, the batch generated as described in this Example was used to test the effect of sterilization (or steam) in place on sucrose:maltose ratio.
Improved Composition Via Manipulation of Crystallization Parameters To a 20 L fermenter (New Brunswick BioFlo 410) was added the following medium:

| Batch: 051315 | kg: | g: |
|---|---|---|
| Water | 12.600 | |
| Sucrose | 1.800 | |
| Maltose-H$_2$O | 0.998 | |
| MnSO$_4$—H$_2$O | 0.00015 | 0.15083 |
| MgSO$_4$ | 0.00146 | 1.46045 |
| FeSO$_4$—7H$_2$O | 0.00015 | 0.14997 |
| KH$_2$PO$_4$ | 0.04000 | 40.00375 |
| NaCl | 0.00015 | 0.14985 |
| CaCl$_2$—2H$_2$O | 0.00080 | 0.80170 |
| Yeast Extract | 0.077 | |
| NaOH, 50% | 0.017 | 16.68234 |
| Total: | 15.534 | |
| TS, %: | 17.374 | |

-continued

| Batch: 051315 | kg: | g: |
|---|---|---|
| Brix, %: | 18.198 | |
| S/M: | 2.00 | |

The pH of the medium was adjusted to 7.00 with NaOH (50%) and the sterilized medium (pre-inoculation) was sampled for analysis of S/M via HPLC-RID. 200 mL of the medium was transferred to an Erlenmeyer flask, the flask was then sealed and autoclaved at 121° C. for 15 minutes. The medium was cooled, and inoculated with 1 mL vial stock (0.5 mL late-log culture Leuconostoc citreum ATCC 13146, NRRL B-742, in 20% glycerol, stored at −75° C.). The seed was incubated with swirling at 27° C. and allowed to grow for 16 Hr.

The balance of the medium was transferred to the fermenter via sanitary pump. The fermenter was sealed and sterilized in place (SIP) to 116° C., as previously described in Example 1. The fermenter was inoculated with 150 mL of the flask seed culture and the pH of the medium was corrected to 6.50 using 37% HCl. Fermentation was allowed to proceed for 55 Hr with pH adjustment with 40% NaOH (40%) to maintain 5.50.

Typically, there is a 6 hour induction period preceding log-growth. Log-growth typically proceeded for approximately 10 hours. A pH 5.5 was typically achieved within about 2 hours of log-phase growth, and this pH is maintained thereafter.

The fermentation consumed 464 g of 40% NaOH.

The completion of fermentation was indicated by consumption of fructose, which was converted to mannitol, and by cessation of the take up of alkali. The fermentation was harvested, and the cells removed via centrifugation (Sorvall RC-5B Plus, G3 rotor, 13,689 g for 20 min at 5-10° C.). The broth was concentrated by evaporation (Buchi R-20 rotavap, 70° C. bath, 54° C. vapor @ 26" Hg) to 40 brix, and decolorized by treatment with 266 g of powdered activated carbon (PAC Carbochem CA-50S) while still hot (50-65° C.). The slurry was stirred for 20 minutes and vacuum-filtered (2×240 mm Buchner funnel, 2 L side-arm flask, Whatman #3 filter papers and a 100 g Celite 545 pre-coat). The PAC cakes were washed with 3×250 mL water each, and the whole collected.

The minerals/salts (primarily sodium) and organic acid metabolites (primarily lactic and acetic acids) were removed in a sequential two-stage ion exchange process. First 6.236 kg of broth at 35.5 brix was passed through 6.8 L strong acid cation exchange resin (Purolite C-150S) to remove the minerals/salts. Then, the de-ashed broth is passed through 14.7 L weak base anion (Purolite A-133) to remove the organic acids. The pH of the de-ashed liquor was adjusted to 6.16 (from 10.80) with HCl (37%), and concentrated by evaporation to 57.01 brix. The de-ashed concentrate was transferred hot into a 2.5 gal crystallization vessel and allowed to slowly cool to room temperature (19-22° C.) and crystallize overnight.

The resulting mixture was homogenized to yield a pourable crystal slurry. The mannitol crystals were separated via basket centrifuge (Robitel RA 20 VX with a 10 μm polypropylene filter bag).

A small portion of the crystal cake (0.279 kg at 95% solids, cake #1) was washed with 500 mL ice-cold deionized water, and a 0.672 kg cake wash (wash #1) at 18.7 brix was retained for recycle while 2.403 kg of liquor (liquor #1) at 52.56 brix was collected.

Liquor #1 was concentrated by evaporation to 65.68 brix. The resulting concentrate was split into two portions. The first portion (0.921 kg) was crystallized again at room temperature (19-22° C.). The second portion was crystallized to a temperature of approximately 2° C. Both crystallizations were allowed to proceed overnight.

The room temperature crystals (cake #2RT, 0.039 kg at 95% solids) were removed, as described above. The cake wash #2RT (0.552 kg) was combined with wash #1 for recycle.

The refrigerated crystals (cake #2RC, 0.094 kg at 95% solids) were removed, as before. The cake wash #2RC (0.626 kg) was combined with wash #1 for recycle.

The product liquors #2RT at 64.08 brix and #2RC at 63.82 brix were analyzed via (HPAEC-PAD, HPLC-RID, brix, pH and conductivity).

Results

HPLC-RID determined that the pre-inoculated sucrose/maltose ratio had increased from 2.00 to 2.73 after sterilization in process:

| Compound: | %/brix Pre SIP | %/brix Post SIP |
|---|---|---|
| Sucrose | 62.26 | 61.14 |
| Maltose | 31.31 | 22.38 |
| Glucose | 0.27 | 4.61 |
| fructose | 0.00 | 0.15 |
| Total: | 93.84 | 88.28 |
| S/M: | 1.99 | 2.73 |

The composition of the products produced as described in this Example after cold and room temperature second crystallization are shown below:

| Cold 2nd Xl, T° C.: Component | 2%/brix | % w/w: | Room Temp 2nd Xl, T° C.: Component | 20%/brix | % w/w: |
|---|---|---|---|---|---|
| Glucose | 0.79 | 0.50 | Glucose | 0.76 | 0.49 |
| Fructose | 0.03 | 0.02 | Fructose | 0.02 | 0.02 |
| Sucrose | 1.76 | 1.12 | Sucrose | 1.62 | 1.04 |
| Maltose | 4.93 | 3.15 | Maltose | 4.84 | 3.10 |
| MIMO | 89.08 | 56.85 | MIMO | 87.75 | 56.23 |
| Mannitol | 8.82 | 5.63 | Mannitol | 11.20 | 7.18 |
| Lactate | 0.33 | 0.21 | Lactate | 0.32 | 0.20 |
| Glycerol | 0.38 | 0.24 | Glycerol | 0.37 | 0.24 |
| Formate | 0.00 | 0.00 | Formate | 0.00 | 0.00 |
| Acetate | 0.13 | 0.09 | Acetate | 0.11 | 0.07 |
| TOTAL: | 106.25 | 67.81 | TOTAL: | 106.99 | 68.56 |
| Brix, %: | 63.82 | | Brix, %: | 64.08 | |
| Purity, %: | 83.84 | | Purity, %: | 82.02 | |
| Mw, Da: | 737 | | Mw, Da: | 739 | |

| MIMO DP | %/brix: | | MIMO DP | %/brix: |
|---|---|---|---|---|
| MIMO-DP3 | 13.84 | | MIMO-DP3 | 13.71 |
| MIMO-DP4 | 31.62 | | MIMO-DP4 | 30.82 |
| MIMO-DP5 | 27.75 | | MIMO-DP5 | 27.30 |
| MIMO-DP6 | 11.50 | | MIMO-DP6 | 11.48 |
| MIMO-DP7 | 3.11 | | MIMO-DP7 | 3.19 |
| MIMO-DP8 | 1.26 | | MIMO-DP8 | 1.25 |
| MIMO-DP9 | 0.00 | | MIMO-DP9 | 0.00 |

Thus, for batches made via cold filter sterilization of the sugars, a sucrose/maltose ratio of 2.73 should give a similar MWD, e.g. 740 to 790 Da.

Increasing the brix of liquor #1 to greater than 65 and cooling the second crystallization to 2-5° C. improved the purity of the product (relative to room temperature crystallization of either 52 or 65.78 brix) by approximately 26% (−3.15% Thrix). The final product so obtained demonstrated improved shelf stability and did not crystallize further once stored at either 5 or 20° C.

This process-iteration (concentration of liquor #1 and sequential crystallization, first to room temperature and then to 2-5° C.) and the composition obtained thereby have been integrated into the commercial-scale process.

Example 3

This Example demonstrates the fermentation at 10 L scale, using a sucrose:maltose ratio of 2.00 at time of inoculation, and with introduction of sugars via filtration through a 0.2 mm filter (sterilized by filtration, SBF).

10 L Trial Fermentation at S/M=2.0 with SBF of Sugars

A sugar and salt stock solution was prepared to contain the following:

| 10 L #1 | kg: |
|---|---|
| Water | 4.471 |
| Sucrose | 1.430 |
| Maltose-$H_2O$ | 0.795 |
| NaCl | 0.00012 |
| $CaCl_2$—$2H_2O$ | 0.00064 |
| Total: | 6.698 |
| TS, %: | 32.05 |
| Brix, %: | 32.06 |
| S/M: | 1.990 |

The following components were added to a 10 L fermenter (BioFlo 410 or equivalent):

| 10 L #1 | SIP kg: |
|---|---|
| Water | 4.500 |
| $MnSO_4$—$H_2O$ | 0.000098 |
| $MgSO_4$ | 0.000951 |

-continued

| 10 L #1 | SIP kg: |
|---|---|
| FeSO$_4$—7H$_2$O | 0.000098 |
| KH$_2$PO$_4$ | 0.02606 |
| Yeast Extract | 0.04887 |
| Total: | 4.576 |
| TS, %: | 0.00 |
| Brix, %: | 1.66 |
| S/M: | n/a |

This mixture was sterilized in place (within the fermenter) at 121° C. for 30 minutes then cooled to room temperature, and 5.4697 kg of the sugar and salt stock solution was transferred (SBF) into the fermenter via 0.2 μm filter to give a pre-inoculation (sampled for analysis) medium with the following composition:

| 10 L #1 | Total kg: |
|---|---|
| Water | 8.402 |
| Sucrose | 1.168 |
| Maltose-H$_2$O | 0.650 |
| MnSO$_4$—H$_2$O | 0.000 |
| MgSO$_4$ | 0.001 |
| FeSO$_4$—7H$_2$O | 0.000 |
| KH$_2$PO$_4$ | 0.026 |
| NaCl | 0.000 |
| CaCl$_2$—2H$_2$O | 0.001 |
| Yeast Extract | 0.049 |
| NaOH, 50% | 0.000 |
| Total: | 10.296 |
| TS, %: | 17.03 |
| Brix, %: | 17.77 |
| S/M: | 1.990 |

The medium was adjusted to pH 6.50 with 50% NaOH, and inoculated with 100 g of late-log *L. citreum* NRRL B-742 grown in medium of the same composition. The fermentation was allowed to proceed for 55 hours with pH control to maintain the pH at 5.5 once that pH was achieved via bacterial acidogenesis. The fermenter was sampled at regular intervals for analysis via HPAEC-PAD and HPLC-RID. Results:

The sucrose:maltose (S/M) ratio of the pre-inoculation medium was confirmed by HPLC-RID (BioRad Aminex, HPX-87P, 80° C., water at 0.6 mL/min):
%/brix

| Compound: | %/brix pre inoc: |
|---|---|
| Sucrose | 61.88 |
| Maltose | 32.00 |
| Glucose | 0.25 |
| fructose | 0.00 |
| Total: | 94.14 |
| S/M: | 1.93 |

Figure 19:
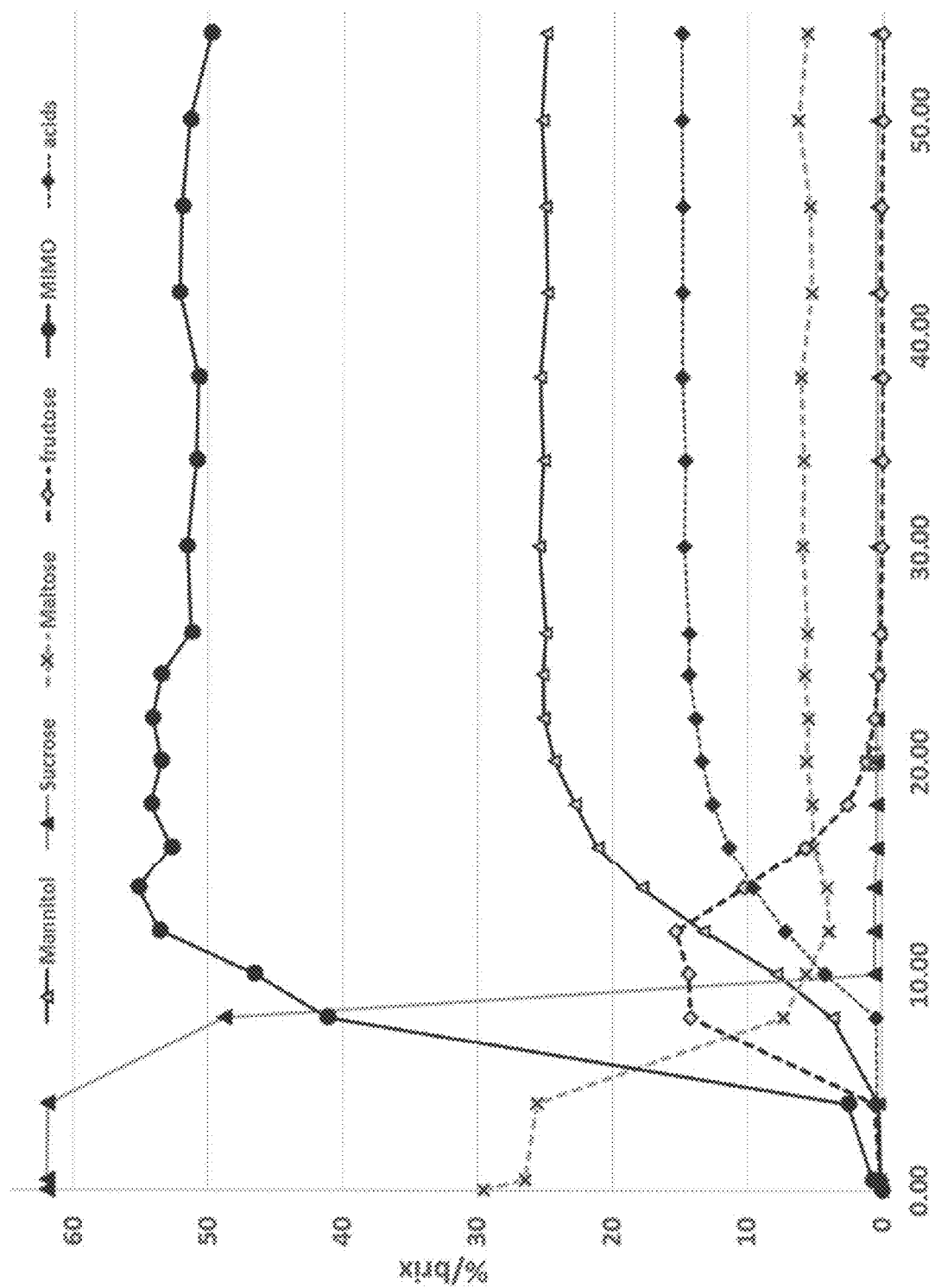
FIG. 19 graphically illustrates the generation of chemical species (as detected by HPAEC-PAD and HPLC-RID) throughout the course of a 10 L fermentation (sucrose: maltose (S/M, w/w) ratio=2.00) with *L. citreum* NRRL B-742.
Figure 20:
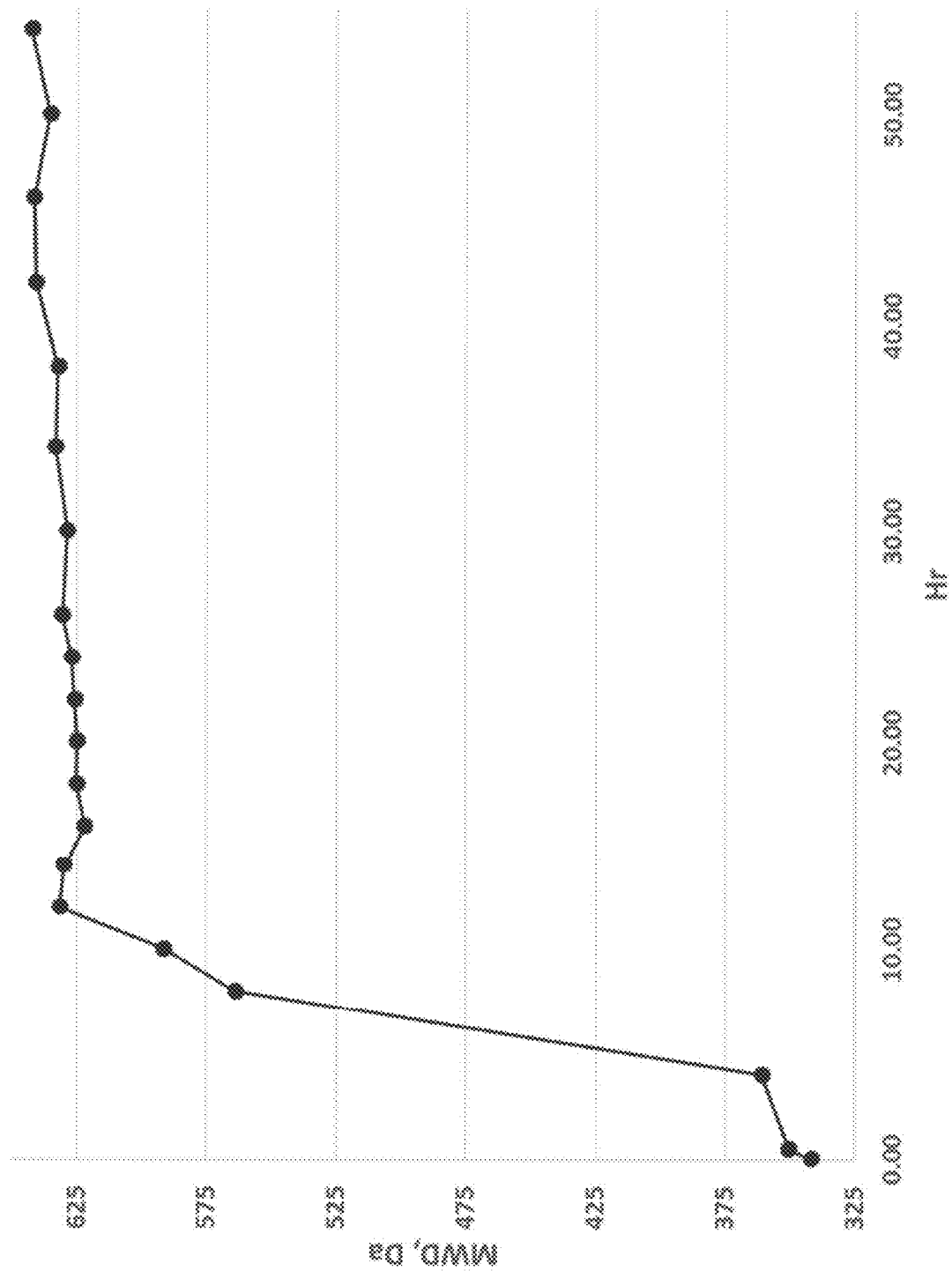
FIG. 20 graphically illustrates evolution of the mass average molecular weight distribution (MWD) of MIMOs throughout the course of a 10 L fermentation (sucrose.

The amount of feedstock (sucrose and maltose), product (MIMO), intermediate (fructose), and byproducts (total organic acids and mannitol) over time as detected via HPLC-RID and HPAEC-PAD, are given in FIG. 19. The evolution of the mass-average molecular weight of the MIMO is shown in FIG. 20.

Ultimately, the starting sucrose:maltose ratio of about 2.00 (1.93 at the time of inoculation) yielded 51.17%/brix MIMO (60.11%/total sugars) that had a mass-average MWD of 642.46. See chart shown in FIG. 40.

Example 4

Figure 8:
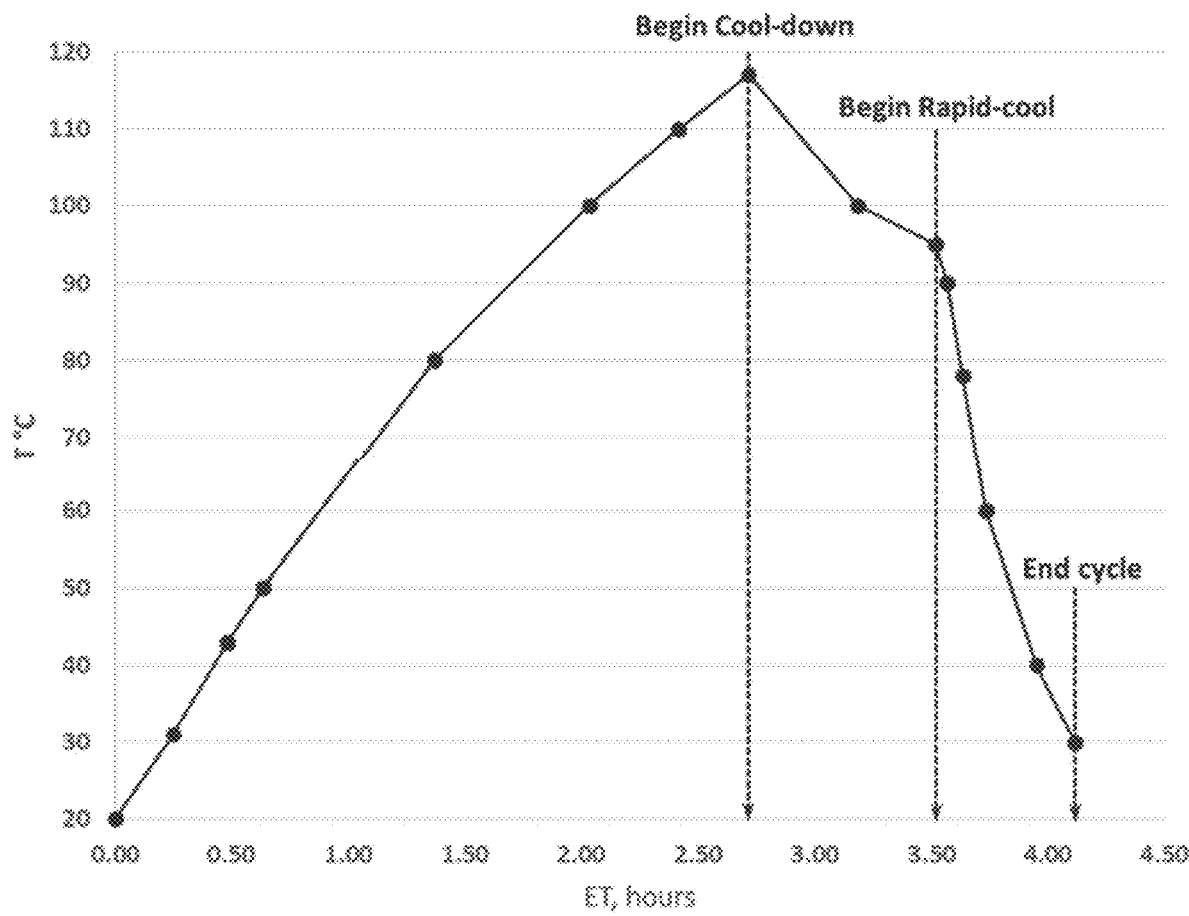
FIG. 8 shows the heating/cooling curve employed during a typical sterilization in place (SIP) cycle run on a New Brunswick BioFlo 410 fermenter.

This Example illustrates that fermentation at the 10 L scale, using a sucrose:maltose ratio of 2.75 at time of inoculation, with introduction of sugars via filtration through a 0.2 μm filter (sterilized by filtration, SBF), will give a MWD similar to that which arises from a fermentation batch with a starting sucrose:maltose ratio of 2.00 prior to SIP (i.e. approx. 2.73 at time of inoculation, see FIG. 8).

10 L Trial Fermentation at S/M=2.75 at the Time of Inoculation with SBF of Sugars Experimentally, this fermentation is identical to that demonstrated in Example #3 with the exception that the amount of both sucrose and maltose have been altered in order to achieve a S/M of 2.75 at the time of inoculation whilst maintaining a total sugar of approximately 17-18% w/w.

The final sterile medium contained:

| 10 L #2 | Total kg: |
|---|---|
| Water | 8.740 |
| Sucrose | 1.333 |
| Maltose-H$_2$O | 0.536 |
| MnSO$_4$—H$_2$O | 0.000 |
| MgSO$_4$ | 0.001 |
| FeSO$_4$—7H$_2$O | 0.000 |
| KH$_2$PO$_4$ | 0.026 |
| NaCl | 0.000 |
| CaCl$_2$—2H$_2$O | 0.001 |
| Yeast Extract | 0.049 |
| NaOH, 50% | 0.000 |
| Total: | 10.685 |
| TS, %: | 16.99 |
| Brix, %: | 17.70 |
| S/M: | 2.751 |

The fermentation behaved normally for *L. citreum* NRRL B-742 grown on this medium and with pH controlled at 5.5 using 50% NaOH. The amounts of feedstock (sucrose and maltose), product (MIMO), intermediate (fructose), and byproducts (total organic acids and mannitol) over time as detected by HPLC-RID and HPAEC-PAD, are given in FIG. 21. Note that the metabolic activities and MIMO yield are essentially the same as those shown in Example #3 (compare FIG. 21 to FIG. 20), but the evolution of the mass-average molecular weight of the MIMO, shown in FIG. 22, is quite different and reflects the increased sucrose:maltose ratio.

Ultimately, fermentation at a sucrose:maltose ratio of about 2.75 (2.72-2.75) at the time of inoculation yielded 53.32%/brix MIMO (57.44%/total sugars) with a mass-average MWD of 760.73 Da. This is consistent with results shown in Example #2 where the pre-inoculated sucrose/maltose ratio had increased from 2.00 to 2.73 during sterilization in place (SIP).

FIG. 41 shows the composition of the fermentation broth so obtained at the left, with the distribution of MIMO at the right.

Example 5

Colored by-products remained in the final product (imparting a brown color and caramel-like flavor) when using the processes described above in Examples 1, 2, and 3. While not undesirable (organoleptically), it is a difficult parameter to control, and it was preferable to avoid destroying maltose from a cost perspective (it is expensive). With these considerations in mind scale-up experiments were designed to test SIP of bulk water and minerals, and filter sterilization of the carbohydrate components. As illustrated in this Example, such a process avoided color formation and facilitated more precise control over the S/M (fixed at 2.75).

Improved Composition for Scale-Up

To a 2 L fermenter (New Brunswick Celligen 512) was added:

| Batch: 51815 | kg: | g: |
|---|---|---|
| Water | 1.752 | |
| $MnSO_4$—$H_2O$ | 0.00002 | 0.02093 |
| $MgSO_4$ | 0.00020 | 0.20312 |
| $FeSO_4$—$7H_2O$ | 0.00002 | 0.02160 |
| $KH_2PO_4$ | 0.00557 | 5.56501 |
| NaCl | 0.00002 | 0.02068 |
| $CaCl_2$—$2H_2O$ | 0.00011 | 0.11113 |
| Yeast Extract | 0.01043 | 10.42705 |
| NaOH, 50% | 0.00096 | 0.95946 |
| Total: | 1.769 | |

This mixture was sealed in the fermenter and autoclaved at 121° C. for 15 minutes. While the contents of the fermenter were still hot (80-90° C.), 0.270 kg of sucrose and 0.108 kg of maltose monohydrate were transferred into the fermenter and dissolved via strong agitation at 400 RPM. Once cooled to 27° C., the whole mixture was sampled for analysis via HPLC-RID, confirming that the sucrose:maltose ratio was 2.72.

The fermenter was inoculated with 20 mL late-log *L. citreum* NRRL B-742, made as previously described, and the pH was controlled as previously mentioned. Fermentation was allowed to proceed for 62 Hr with daily sampling. During this time, the fermentation consumed approximately 43 g of 40% NaOH.

At 62 Hr, the whole batch was harvested and the cells removed, as previously described, to give 17.8 brix broth with a conductivity of 19.1 mS/cm. The broth was of much lower color, e.g. 1039.5 IU relative to 11,799 IU for the same (complete) media run through and SIP cycle. Due to the reduced color, the requirement for powdered activated carbon was reduced by a factor of four, and still have headroom within a factor of two.

The broth was concentrated to 45.0 brix by evaporation, and decolorized with 0.1333% (over starting mass of medium) CA-50S PAC (29.2 g), as previously described.

The minerals/salts and organic acids were removed from 1.075 kg of decolorized liquor at 39 brix as previously described. The combined de-ashed liquor was adjusted to pH 6.16 (from pH 10.80) with 37% HCl (8.73809 g) and the whole de-ashed liquor concentrated by evaporation to 57.04 brix.

The de-ashed concentrate was transferred hot into a one liter crystallization vessel and allowed to slowly cool to room temperature (19-22° C.) and crystallize overnight.

The resulting mixture was homogenized to yield a pourable crystal slurry. The mannitol crystals were separated via basket centrifuge (Robitel RA 20 VX with a 10 μm polypropylene filter bag). The crystal cake (0.320 kg at 95% solids, cake #1) was washed, in small portions, with 500 mL ice-cold deionized water. 0.697 kg cake washings (wash #1) at 20.5 brix were retained for recycle. 2.626 kg liquor (liquor #1) at 51.70 brix was refrigerated to 3° C. and allowed to crystallize overnight.

The crystals (cake #2, 0.109 kg at 95% solids) were removed, as before. The cake wash #2 was combined with wash #1 for recycle. The product liquor #2 at 49.0 brix was analyzed (HPAEC-PAD, HPLC-RID, brix, pH and conductivity).

Results

The composite results via HPAEC-PAD and HPLC-RID are given below.

| Hr: | 15 | 39 | 63 |
|---|---|---|---|
| brix: | 18.2 | 17.8 | 17.8 |
| mannitol | 25.88 | 26.50 | 26.49 |
| glucose | 0.02 | 0.13 | 0.67 |
| fructose | 1.73 | 0.06 | 0.01 |
| sucrose | 0.22 | 0.13 | 0.23 |
| maltose | 2.35 | 2.49 | 3.01 |
| DP 3 | 10.71 | 7.41 | 7.39 |
| DP 4 | 20.26 | 16.83 | 13.98 |
| DP 5 | 17.49 | 16.90 | 15.68 |
| DP 6 | 6.29 | 7.56 | 7.87 |
| DP 7 | 1.58 | 2.16 | 2.49 |
| DP 8 | 0.79 | 0.91 | 1.21 |
| DP 9 | 0.00 | 0.00 | 0.00 |
| lactate | 9.55 | 13.01 | 13.17 |
| glycerol | 0.00 | 0.00 | 0.00 |
| formate | 0.00 | 0.00 | 0.00 |
| acetate | 4.52 | 4.77 | 4.85 |
| TOTAL: | 102.02 | 100.51 | 98.77 |
| MIMO, %: | 57.13 | 51.76 | 48.62 |
| Purity, %: | 56.00 | 51.50 | 49.22 |
| MWD: | 727.43 | 754.80 | 761.03 |
| Yield %: | 57.78 | 51.97 | 49.68 |

Example 6

The process incarnations described in the previous examples (1-5) were integrated and scaled up to 3000 L with a theoretical overall process yield of 240 kg MIMO (DS)/total sugars fed. These examples detail the scaled process, and the composition obtained thereby.

Commercial-Scale Production of MIMO

Fermentation/MIMO Biosynthesis

To 3.7 kg RO (reverse osmosis) water was added sucrose (refined white, from cane), 0.5302 kg; maltose monohydrate (Sunmalt-S[N]), 0.2935 kg; yeast extract (Marcor bacteriological grade), 0.0221 kg; potassium phosphate monobasic, 0.0118 kg; magnesium sulfate (anhydrous), 0.00043 kg; ferrous sulfate heptahydrate, 0.000045 kg; manganese sulfate monohydrate, 0.000045 kg, sodium chloride, 0.000045 kg, and calcium chloride dihydrate (USP), 0.00024 kg.

The pH of the medium was adjusted to 7.0 with 50% NaOH (FCC), 0.0057 kg.

700 mL of medium was dispensed into each of six unbaffled Fernbach flasks. The flasks were sealed using foam plugs and autoclaved at 121° C. for 15 minutes.

Five of the six flasks were inoculated with 1 mL each of vial stock (*Leuconostoc citreum* NRRL B-742; 0.5 mL late-log culture+0.5 mL glycerol, 40%, certified Kosher-Pareve). The sixth flask was an uninoculated control.

The flasks were incubated at 27° C. for 16 Hr ($OD_{600}$=1.476±0.03) with agitation at 150 RPM. The inoculum was inspected via microscopy to determine the culture was clean prior to use.

The following was added to a batch tank: water purified by reverse osmosis (RO water) 1440 kg; sucrose, 498.96 kg; maltose monohydrate, 200 kg; sodium chloride, 0.037 kg; and calcium chloride dihydrate, 0.204 kg.

In the meantime, a 1200 gallon seed fermenter was cleaned in place. To the seed fermenter was added RO water, 238 kg; yeast extract, 2.76 kg; potassium phosphate monobasic, 1.48 kg; magnesium sulfate (anhydrous); 0.054 kg, ferrous sulfate heptahydrate, 0.0057 kg; and manganese sulfate monohydrate, 0.0057 kg.

The contents of the fermenter were thoroughly mixed, allowed to rest at 37° C. for two hours, and then sterilized in place at 121° C. for 60 minutes.

Once cooled, 309.2 kg of the sugar and salt solution was transferred from the charge tank to the seed fermenter through a sterilizing 0.2 µm filter capsule with a 1.0 µm pre-filter (20' Cuno cartridge filter). The filter and lines were washed through with 10 kg of RO water. The mixed medium had a pH of 5.47.

The seed fermenter was inoculated with 3.8 kg late-log flask culture. The fermentation was allowed to proceed under 1-3 psig air (in headspace to maintain positive pressure), at 27° C., with agitation at 42 RPM for 16 hours ($OD_{600}$=2.74).

In the meantime, into a cleaned in place production fermenter was added RO water, 1332 kg, yeast extract, 15.01 kg; potassium phosphate monobasic, 8.01 kg; magnesium sulfate (anhydrous), 0.2922 kg; ferrous sulfate heptahydrate, 0.030 kg, and manganese sulfate monohydrate, 0.030 kg. This mixture was sterilized in place at 121° C. for 60 mins. Into this mixture was pumped 1141 kg of the sugar and salt solution (from the charge tank) through a sterilizing 0.2 µm filter capsule with a 1.0 µm pre-filter (20' Cuno cartridge filter).

Thirty-one kg of late-log seed culture (*L. citreum* NRRL B-742.) was used to inoculate the production fermenter. The pH was adjusted to 6.52 with 50% NaOH, and the fermentation was allowed to proceed for 55 hours at 27° C., 1-3 psig air, and with agitation at 31 RPM. The pH was maintained at 5.5 with 50% NaOH (appx 120 kg).

FIG. 23 graphically illustrates the pH (3.32 final) and the $OD_{600}$ (2.74 final) in the seed tank, while FIGS. 24-26 demonstrate the pH (5.58 final), the $OD_{600}$ (8.78 final) in the production fermenter, the composition of the broth therein made, and MIMO molecular weight over time during the fermentation.

Downstream Processing/Work Up

The biomass (cells, etc.) was removed from the fermentation broth via passage through a 0.2 µm microfilter (skid). Any remaining MIMO held up in the retentate was recovered via six stages of diafiltration. The permeate and diafiltrate were combined and evaporated to approximately 40 brix via wiped film evaporator (WFE). The resulting concentrate was discharged hot and treated with 12.5 kg of powdered activated carbon (PAC, Carbochem CA-50S) and 21 kg Celite 545 diatomite filter aid. The whole mixture was stirred for 20 minutes before filtration through a filter press with a 20 kg Celite 545 pre-coat. A 1 µm cartridge filter was used to polish fines from the filtrate. RO water, 700 kg was used to wash the PAC cake.

The filtrate and PAC wash were combined to give 1277 kg of decolorized concentrate at 29.3 brix.

The decolorized concentrate was de-ashed via passage (5×300 kg slugs) through strong acid cation (SAC, Purolite C-150S, H$^+$ form, 14.0 cuft) and a weak base anion (WBA, Purolite A-133, free-base form, 13.5 cuft) ion exchange resins.

The combined ion exchange (IEX) product (5.6 brix) was filtered through a 0.2 mm capsule filter into a cleaned in place holding tank where it was adjusted to pH<4.2 (2.8, actual) with 31% hydrochloric acid.

The acidified IEX product was concentrated to 54.21 brix via evaporation (WFE), discharged hot into 2×1 m$^3$ stainless steel totes. These were allowed to slowly cool, with slow agitation (pneumatic mixer) to room temperature (25° C.).

The crystals were removed from the mother liquor via passage through a Hastalloy nutsch filter (10 mm filter disk and Celite 545 pre-coat) to yield 273 kg of liquor #1.

The crystal cake (153 kg) was washed with cold RO water, 285 kg to yield 342 kg cake wash #1 and 60 kg cake #1.

Cake wash #1 was frozen for recycle into a future batch and Liquor #1 was evaporated to 65.60 brix by evaporation (pot still). The resulting liquor was discharged hot into a 1 m$^3$ stainless steel tote and allowed to slowly cool, with slow agitation (pneumatic mixer) to room temperature (25-30° C.). Then, the tote was moved into a freezer where the crystallization was continued with slow cooling to 5° C.

The crystals were removed from the mother liquor via passage through a Hastalloy nutsch filter (10 mm filter disk and Celite 545 pre-coat) to yield 127.1 kg of liquor #2 at 64.04° brix. The crystal cake was washed with cold RO water to yield 184 kg cake wash #2 and 39.4 kg cake #2.

Cake wash #2 was frozen for storage and recycle into the next batch.

Liquor #2 was pasteurized at 70° C. for 30 minutes in the pot still, cooled and packaged into 55 gallon sanitized poly drums.

Samples were submitted for microbiological testing and to analytics for issuance of batch COA.

The composition thereby made was as shown in FIG. 42 (as detected by HPAEC-PAD/HPLC-RID).

FIG. 27 shows a HPAEC-PAD chromatogram of product lot #150622 wherein the components are identified as A: D-mannitol; B: L-arabinose (internal standard); C: D-glucose; D: D-fructose; E: sucrose; F: maltose; and where G-M correspond to MIMO DP 3-9.

FIG. 28 shows HPAEC-PAD chromatograms during removal of mannitol from mother liquor 1, and 2, 3 corresponding to compound crystallization stages, 1 and 2, respectively. The components are identified as A: D-mannitol; B: L-arabinose (internal standard); C: D-glucose; D: D-fructose; E: sucrose; F: maltose; and G-M corresponding to MIMO DP 3-9. Note that mannitol is reduced and that the MIMO purity increased thereby.

FIG. 29 shows an overlay of 1D 300 MHz $^1$H NMR (water suppressed in $D_2O$) spectra of the anomeric regions of 1 and 2, NC and lot #150622 products, respectively and, 3, D-panose (δ reference) wherein signal A correspond to α-(1,4) anomeric protons; signal B corresponds to α-(1,6) anomeric protons; signals C and D correspond to the reducing α and β anomeric protons, respectively, at the reducing end; and signals E and F correspond to regions corresponding to α-(1,3) and α-(1,2) anomeric protons, respectively. Note the minimal or absent second doublet in lot #150622; this is likely due to the acidification step which avoids possible alkali catalyzed epimerization of C2.

FIG. 30 shows an overlay of 1D 300 MHz $^1$H NMR (water suppressed in $D_2O$) spectra of the non-anomeric regions of 1, NC and, 2, lot #150622 products.

FIG. 31 shows an overlay of 1D 300 MHz $^1$H NMR (water suppressed in D$_2$O) spectra of the alkyl regions of (1) lot #150622; and (2) A2 products. Signal A is an unknown; signal B corresponds to acetyl protons (the difference is due to pH, A2=4.81, lot #150622=6.08); signal C corresponds to lactate C3 methyl protons; and signal D is unassigned. Note, the amount of acetate/lactate in both 1 and 2 (A2) were below the minimum detectable limit (MDL) of HPLC-RID.

Example 7

The composition and process described in Example 6 was modified to increase product recovery (minimizing losses and materials retained for batch-recycle). The modified process and composition so produced are detailed here.
Modified Process and Composition Made Thereby—the State of the Art
Fermentation/MIMO Biosynthesis To 3.7 kg RO (reverse osmosis) water was added sucrose (refined white, from cane), 0.5302 kg; maltose monohydrate (Sunmalt-S[N]), 0.2935 kg; yeast extract (Marcor bacteriological grade), 0.0221 kg; potassium phosphate monobasic, 0.0118 kg; magnesium sulfate (anhydrous), 0.00043 kg; ferrous sulfate heptahydrate, 0.000045 kg; manganese sulfate monohydrate, 0.000045 kg, sodium chloride, 0.000045 kg, and calcium chloride dihydrate (USP), 0.00024 kg.

The pH of the medium was adjusted to 7.0 with 50% NaOH (FCC), 0.0057 kg.

700 mL of medium was dispensed into each of six unbaffled Fernbach flasks. The flasks were sealed using foam plugs and autoclaved at 121° C. for 15 minutes.

Five of the six flasks were inoculated with 1 mL each of vial stock (*Leuconostoc citreum* NRRL B-742; 0.5 mL late-log culture+0.5 mL glycerol, 40%, certified Kosher-Pareve). The sixth flask was a non-inoculated control.

The flasks were incubated at 27° C. for 16 Hr (OD$_{600}$=1.476±0.03) with agitation at 150 RPM. The inoculum was inspected via microscopy to determine the culture was clean prior to use. A sample was taken and frozen at −75° C. in 20% w/w glycerol for later analysis via 16S rRNA sequencing to determine and verify culture purity.

In the meantime, a 1200 gallon seed fermenter was cleaned in place.

A batch tank was loaded with RO water, 1510 kg; sucrose, 522.04 kg; maltose monohydrate, 210 kg; sodium chloride, 0.039 kg; and calcium chloride dihydrate, 0.214 kg.

To the seed fermenter was added RO water, 238 kg; yeast extract, 2.80 kg; potassium phosphate monobasic, 1.50 kg; magnesium sulfate (anhydrous) 0.055 kg; ferrous sulfate heptahydrate, 0.0057 kg; and manganese sulfate monohydrate, 0.0059 kg.

The contents of the fermenter were thoroughly mixed, allowed to rest at 37° C. for two hours, and then sterilized in place at 121° C. for 60 minutes.

Once cooled, 310 kg of the sugar and salt solution was transferred from the charge tank to the seed fermenter through a sterilizing 0.2 µm filter capsule with a 1.0 µm pre-filter (20' Cuno cartridge filter). The filter and lines were washed through with 10 kg of RO water. The mixed medium had a pH of 5.54.

The seed fermenter was inoculated with 3.8 kg late-log flask culture. The fermentation was allowed to proceed under 1-3 psig air (in headspace to maintain positive pressure) at 27° C., with agitation at 42 RPM for 16 hours (OD$_{600}$=2.805, pH 3.45).

In the meantime, the following were added to a cleaned in place production fermenter: RO water, 1332 kg; yeast extract; 5.6 kg; potassium phosphate monobasic, 8.05 kg; magnesium sulfate (anhydrous), 0.2922 kg; ferrous sulfate heptahydrate, 0.030 kg; and manganese sulfate monohydrate, 0.030 kg. The fermentation contents were sterilized in place at 121° C. for 60 mins. The following was pumped into the production fermenter: 1680 kg of the sugar and salt solution (from the charge tank) through a sterilizing 0.2 µm filter capsule with a 1.0 µm pre-filter (20' Cuno cartridge filter). The filter and lines were washed through with 10 kg of RO water.

Thirty-one kg of late-log seed culture was used to inoculate the production fermenter. The pH was adjusted to 6.54 with 50% NaOH (~1 kg), and the fermentation was allowed to proceed for 55 hours at 27° C., with 1-3 psig air, and with agitation at 31 RPM. The pH was maintained at 5.5 with 50% NaOH (appx 120 kg). A sample was taken and frozen at −75° C. in 20% w/w glycerol for later analysis via 16S rRNA sequencing to determine and verify culture purity.

FIG. 32 shows the amounts of chemical species as detected by HPAEC-PAD and HPLC-RID throughout the course of a 3000 L fermentation (S/M=2.75, lot #151105) using *L. citreum* NRRL B-742.

FIG. 33 illustrates the evolution of the molecular weight distribution of MIMOs throughout the course of a 3000 L fermentation (S/M=2.75, lot #151105) with *L. citreum* NRRL B-742. Note that the MWD continues to increase (until about 15 hours) after the sucrose is exhausted (at about 10 hours). The rate of chain growth then takes place at a lower, but constant rate until the end of fermentation (55 hours) when the molecular weight of about 776.5 Da was achieved.

Downstream Processing/Work Up:

The biomass (cells, etc.) was removed from the fermentation broth via passage through a 0.2 µm microfilter (skid). Remaining MIMO held up in the retentate was recovered via six stages of diafiltration. The permeate and diafiltrate were combined (6745 kg at 8.6° brix) and evaporated to 48.31 brix using a wiped film evaporator (WFE). The WFE was washed with RO water and the washings retained for further use (WFE wash #1).

The resulting concentrate was discharged hot and treated with 12.5 kg of powdered activated carbon (PAC, Carbochem CA-50S) and 21 kg Celite 545 diatomite filter aid. The mixture was stirred for 20 minutes before filtration through a filter press with a 20 kg Celite 545 pre-coat. A 1 µM cartridge filter was used to polish fines from the filtrate. Wash water (11.13 brix out) from the wiped film evaporator (WFE wash #1, 700 kg), followed by an RO water push (1.7 brix out), was used to wash the PAC cake.

The filtrate and PAC wash were combined to give 1873 kg of decolorized concentrate at 25.7 brix. The decolorized concentrate was de-ashed via passage (5×325 kg slugs) through strong acid cation (SAC, Purolite C-150S, H$^+$ form, 14 cuft) and a weak base anion (WBA, Purolite A-133, free-base form, 13.5 cft) ion exchange resins.

The combined ion exchange product (5.6 brix) was filtered through a 0.2 µm capsule filter (30" PRMXE) into a cleaned in place holding tank where it was adjusted to pH<4.2 (2.8, actual) with 85% phosphoric acid.

The acidified ion exchange product was concentrated to 52.64 brix via evaporation using a wiped film evaporator, and then discharged hot into 2×1 m$^3$ stainless steel totes. These were allowed to slowly cool, with slow agitation (pneumatic mixer) to room temperature (25° C.). The wiped film evaporator was rinsed with RO water and retained for further use downstream in the process (1.7 brix, WFE wash #2).

The crystals were removed from the mother liquor via passage through a Hastalloy nutsch filter (10 mm filter disk and Celite 545 pre-coat) to yield 571 kg of liquor #1 at 49.7° brix.

The 118 kg crystal cake was washed with cold wiped film evaporator rinse water (WFE wash #2) to yield 218 kg cake wash #1 at 24.3 brix and 54.4 kg cake #1.

Liquor #1, cake wash #1, and any remaining WFE wash #2 were combined, and evaporated to 67.7 brix by evaporation (pot still). The resulting liquor was cooled to 30° C. and discharged into a 1 m³ stainless steel tote. Then, the tote was moved into a freezer where the crystallization was continued with slow cooling to 5° C. The pot still was rinsed with 200 kg RO water to yield 196 kg wash at 1.2° brix (still wash) which was refrigerated for downstream use.

The crystals were removed from the mother liquor via passage through a Hastalloy nutsch filter (10 mm filter disk and Celite 545 pre-coat) to yield 315 kg of liquor #2 at 63.5° brix.

The 165.25 kg crystal cake was washed with the cold still wash to yield 248 kg cake wash #2 at 27° brix and 77.65 kg cake #2.

Cake wash #2 and any remaining pot-still rinse was frozen for storage and recycle into the next batch.

315 kg Liquor #2 was pasteurized at 70° C. for 30 minutes in a pot still, cooled and packaged into 55 gallon Scholle bags (Bag in box) with sanitary fittings. The yield was 314.3 kg pasteurized product containing 170.3 kg MIMO at 63.01 brix.

Samples were submitted for microbiological testing and to analytics for issuance of batch certificate of analysis. Chromatograms comparing lot #150622 with this one, lot #151105, are overlaid and given in FIG. 34.

Fermentation yield was 51.23% over total sugars fed. Process recovery was, overall, 62.40% with 77.52% potentially recoverable or 31.97% yield over total sugars fed. The overall balance of mass for the DSP was (significant points in bold-text):

| Sample: | kg: | Brix: | DS, kg: | Purity, %: | ISOT, kg: |
|---|---|---|---|---|---|
| Final broth | 3081 | 18.10 | 557.63 | 48.94 | 272.92 |
| permeate init | 2175 | 18.00 | 391.50 | 46.82 | 183.30 |
| retentate init | 2250 | 18.00 | 405.00 | 49.28 | 199.58 |
| Perm Stage 1 | 825 | 10.1 | 83.33 | 46.82 | 39.01 |
| Perm Stage 2 | 750 | 6.1 | 45.75 | 46.82 | 21.42 |
| Perm Stage 3 | 750 | 3.3 | 24.75 | 46.82 | 11.59 |
| Perm Stage 4 | 750 | 2.0 | 15.00 | 46.82 | 7.02 |
| Perm Stage 5 | 750 | 1.3 | 9.75 | 46.82 | 4.57 |
| Perm Stage 6 | 750 | 0.7 | 5.25 | 46.82 | 2.46 |
| Pooled permeate | 6745 | 8.6 | 580.07 | 46.82 | 271.59 |
| Retentate Stage 1 | 750 | 10.3 | 77.25 | 49.28 | 38.07 |
| Retentate Stage 2 | 750 | 6.1 | 45.75 | 49.28 | 22.54 |
| Retentate Stage 3 | 750 | 3.5 | 26.25 | 49.28 | 12.94 |
| Retentate Stage 4 | 750 | 2.0 | 15.00 | 49.28 | 7.39 |
| Retentate Stage 5 | 750 | 1.3 | 9.75 | 49.28 | 4.80 |
| Retentate Stage 6 | 750 | 0.9 | 6.75 | 49.28 | 3.33 |
| WFE concentrate tote #1 | 781 | 47.9 | 374.10 | 48.88 | 182.87 |
| WFE concentrate tote #2 | 329 | 49.3 | 162.20 | 48.88 | 79.29 |
| Pooled WFE concentrate | 1110 | 48.31 | 536.30 | 51.41 | 262.16 |
| WFE distillate | 5544 | 0.2 | 11.09 | 51.41 | 5.70 |
| WFE wash 1 | 700 | 1.8 | 12.60 | 51.41 | 6.48 |
| Product filtrate tote #1 | 756 | 32 | 241.92 | 48.88 | 118.26 |
| Product filtrate tote #2 | 243 | 40 | 97.20 | 48.88 | 47.51 |
| Filter press wash | 634 | 11.3 | 71.64 | 50.36 | 36.08 |
| RO wash | 2400 | 1.7 | 5.10 | 53.82 | 2.74 |
| Pooled Product Filtrate | 1873 | 25.70 | 481.36 | 50.86 | 244.83 |
| Pan drippings | 198 | 15.20 | 30.10 | 50.47 | 15.19 |
| IEX pulse #1 | 1317 | 5.0 | 66.18 | 57.65 | 38.16 |
| IEX pulse #2 | 1370 | 5.4 | 73.98 | 57.65 | 42.65 |
| IEX pulse #3 | 1619 | 5.1 | 82.57 | 57.65 | 47.60 |
| IEX pulse #4 | 1749 | 4.9 | 85.70 | 57.65 | 49.41 |
| IEX pulse #5 | 1855 | 4.7 | 87.19 | 57.65 | 50.27 |
| IEX pulse #6 | 1629 | 1.8 | 29.45 | 57.65 | 16.98 |
| Pooled IEX effluent | 9426 | 4.51 | 425.06 | 57.65 | 245.07 |
| 0.2 mm filtration | RT | n/a | | | |
| acidification | 0.5 | n/a | | | |
| WFE IEX concentrate | 695 | 58.68 | 407.83 | 57.65 | 235.13 |
| WFE IEX distillate | 6835 | 0.2 | 13.67 | 57.65 | 7.9 |
| WFE IEX wash #1 | 250 | 1.7 | 4.25 | 57.65 | 2.5 |
| WFE IEX wash #2 | 250 | 0.1 | 0.25 | 57.65 | 0.1 |
| Stage 1 liquor | 571 | 49.7 | 283.79 | 71.62 | 203.2 |
| Stage 1 crystals | 153.7 | 78.18 | 120.16 | 23.62 | 28.4 |
| Stage 1 crystal wash | 218 | 24.3 | 52.97 | 44.19 | 23.4 |
| Stage 1 washed crystals | 54.4 | 78.38 | 42.64 | 4.62 | 2.0 |
| to Still | 789 | 42.68 | 336.76 | 64.04 | 215.7 |
| 2nd crystal feed | 444.3 | 67.70 | 300.79 | 66.81 | 201.0 |
| Still wash | 196 | 1.2 | 2.35 | 50.01 | 1.2 |
| Stage 2 liquor | 315 | 63.5 | 200.03 | 85.57 | 171.2 |
| Stage 2 crystals | 165.25 | 82.19 | 135.82 | 37.30 | 50.7 |
| Stage 2 crystal wash | 248 | 27 | 66.96 | 60.37 | 40.4 |
| Stage 2 washed crystals | 77.65 | 77.52 | 60.19 | 9.33 | 5.6 |
| Pasteurized product | 314.3 | 63.01 | 198.05 | 86.00 | 170.3 |

The composition of the product (pasteurized product) so made is shown in FIG. 39.

The composition described herein is discrete, and can be differentiated via chromatography, from the major commercial IMO products that are available today. A comparison of the ISOThrive™ composition, which is heretofore canon, with the commercial prebiotic IMO-based compositions, is given in FIG. 35.

A summary of the process illustrated in Example 7 is shown in FIG. 36.

Example 8

Four more batches were produced in 3000 liter batches using the methods described in the foregoing Examples. These four batches had batch numbers 150622, 151105, 160120, and 161202, and had the following compositions.

| Batch | 150622 | 151105 | 160120 | 161202 |
|---|---|---|---|---|
| brix | 67.35 | 69.33 | 69.69 | 64.57 |
| glycerol | 0.55 | 0.39 | 0.46 | 0.34 |
| erythritol | 0.27 | 0.15 | 0.18 | 0.16 |
| mannitol | 8.01 | 6.23 | 5.97 | 5.96 |
| glucose | 0.42 | 0.92 | 1.10 | 0.92 |
| fructose | 0.05 | 0.15 | 0.16 | 0.13 |
| leucrose | 2.13 | 2.03 | 1.79 | 1.81 |
| sucrose | 0.62 | 0.69 | 0.65 | 0.79 |
| maltose | 2.98 | 3.85 | 3.73 | 4.34 |
| 1,6-DP2 | 0.21 | 0.14 | 0.13 | 0.27 |
| 1,4-DP3 | 1.65 | 1.82 | 1.84 | 1.93 |
| 1,6-DP3 | 0.28 | 0.43 | 0.44 | 0.47 |
| 1,6-DP4 | 0.32 | 0.53 | 0.56 | 0.54 |
| MIMO-DP3 | 9.94 | 11.04 | 10.44 | 12.27 |
| MIMO-DP4 | 22.76 | 24.13 | 23.49 | 25.53 |
| MIMO-DP5 | 26.27 | 26.67 | 26.56 | 26.32 |
| MIMO-DP6 | 15.74 | 14.54 | 15.32 | 13.16 |
| MIMO-DP7 | 5.09 | 4.34 | 4.72 | 3.53 |
| MIMO-DP8 | 2.06 | 1.60 | 1.89 | 1.20 |
| MIMO-DP9 | 0.65 | 0.54 | 0.56 | 0.32 |
| lactic acid | 0.00 | 0.00 | 0.01 | 0.02 |
| acetic acid | 0.00 | 0.00 | 0.00 | 0.00 |
| Purity, % | 83.11 | 83.63 | 83.98 | 83.34 |
| Mw, Da | 782.7 | 763.9 | 773.6 | 745.5 |

Example 9

This Example shows that media from growth of *Lactobacillus gasseri* or *Lactococcus lactis* can affect the morphology and growth of head and neck squamous cell carcinoma (HNSCC) cells.

Methods

Overnight cultured head and neck squamous cell carcinoma (HNSCC) cells (HSC-3 and 14A cells; 70-80% confluency) were treated with different concentrations (25, 50, 100, 150, 200 and 300 mg/ml; BCA protein assay) of broth obtained from *Lactobacillus gasseri* ATCC 4962 or *Lactococcus lactis* subsp. *lactis* NRRL B-1821 bacteria for 2 hours. After 2 hours the media was removed and replaced with regular medium and the carcinoma cells were then cultured for another 12 hours. No bacterial contamination or precipitation of the cancer cell media was observed during the incubation.

Results

Cell growth inhibition and morphological changes were induced by *Lactobacillus gasseri* and *Lactococcus lactis* in HSC-3 cells in a dose-dependent manner. Slight induction of morphological changes in the squamous cell carcinoma (HNSCC; 14A) cells were also observed. These preliminary results indicate that broth from *Lactobacillus gasseri* may be a more effective inhibitor of head and neck squamous cell carcinoma cell growth than broth from *Lactococcus lactis*.

These results also show that cancer cells can be treated with conditioned media continuously for 12-18 hours (overnight).

Example 10

This Example illustrates that culture medium obtained after growth of *Lactobacillus gasseri* ATCC 4962 or *Lactococcus lactis* subsp. *lactis* NRRL B-1821 can inhibit colon cancer cell growth.

Cell Proliferation Assay

Growth of HCT-15 and DLD-1 colorectal cancer cells was examined during exposure to media obtained after growth of *Lactobacillus gasseri* ATCC 4962 or *Lactococcus lactis* subsp. *lactis* NRRL B-1821. The HCT-15 cells are human colonic epithelium, adherent, Dukes' type C colorectal cancer cells. The DLD-1 cells are human colonic epithelium, adherent, Dukes' type C colorectal cancer cells differentiated from HCT-15 and originating from different chromosomal aberrations (but the mutations are within the HCT-15 parent cell line).

HCT-15 and DLD-1 colorectal cancer cells were incubated for 24 hours with control media or cell-free broth from *Lactobacillus gasseri* ATCC 4962 or *Lactococcus lactis* subsp. *lactis* NRRL B-1821 cultures (100, 200, 400 or 800 μg/mL).

To determine the effect of broth from *Lactobacillus gasseri* ATCC 4962 or *Lactococcus lactis* subsp. *lactis* NRRL B-1821 cultures on cancer cell proliferation, a CyQUANT NF Cell Proliferation Assay Kit was used according to manufacturer's instructions (Invitrogen/Life Technologies, Grand Island, N.Y.).

Results

As illustrated in FIG. 37A-37B, broth from *Lactobacillus gasseri* and *Lactococcus lactis* cultures reduced colon cancer cell proliferation in a dose-dependent manner relative to control culture media. These data indicate that *Lactobacillus gasseri* and *Lactococcus lactis* secrete a substance that inhibits cancer cell growth.

Example 11

This Example illustrates that *Weissella viridescens* growth is inhibited by nisins A and Z. Bacteria assigned to the genus *Weissella* are Gram-positive, catalase-negative, non-endospore forming cells with coccoid or rod-shaped morphology. *Weissella viridescens* can be an opportunistic pathogen involved in human infections.

Materials and Methods

Purified nisin A and Z are commercially available and were acquired from Handary S. A. (Brussels Belgium). Certificates of analysis for each lot indicated purities of 95.2 and 99.6% for nisin A and Z, respectively.

100 g De-Man, Rogosa and Sharpe (MRS) media was prepared in a 500 mL Erlenmeyer to contain 5.5% solids in deionized water (18.2 MΩ, Hydro Service and Supplies, Gaithersburg, Md.). The media was autoclaved (121° C. 15 min), cooled, and inoculated with 1 mL (0.5 mL culture+0.5 mL glycerol, 40%; frozen at −78° C.) of *Weissella viridescens* NRRL B-1951 (test strain). The culture was incubated at 31° C. overnight (15 Hr).

The next day, stock solutions of either nisin A or Z were prepared in deionized water to contain 31.3 and 33.7 μg/g of each peptide.

100 g MRS media was prepared to contain 5.5% solids. Two sets (one set each for nisin A and nisin Z) of eight Hach-type tubes (Kimble Chase 45066-16100) were prepared. Within each set, in order was added 5.00, 4.95, 4.90, 4.75, 4.50, 4.00, 3.50 and 3.00 g MRS media. The tubes were sealed and autoclaved.

To each tube was added, of the appropriate nisin stock, 0.00, 0.05, 0.10, 0.25, 0.50, 1.00, 1.50, and 2.00 g. Each tube was inoculated with 0.25 g of late-log *W. viridescens* NRRL B-1951 culture. The tubes were sealed and the absorbance at 600 nm was quickly measured (Hach DR900). The tubes were segregated by set and incubated at 31° C. overnight (15 Hr).

Each tube was sampled (1.5 mL conical polypropylene centrifuge tubes) and centrifuged at 10 kRPM for 10 minutes to remove and suspended cells. The resulting supernatants were filtered (0.2 μm nylon), diluted to 0.5% solids, and analyzed by high pressure liquid chromatography (HPLC, Agilent 1100, refractive index detector and BioRad Ainex HPX-87H column) for consumption of glucose and production of organic acids. The following table illustrates the concentration of sugars such as glucose and production of organic acids during the incubation.

| Concentration of Sugars and Organic Acids in the Fermentation Media | | | | | | | |
| --- | --- | --- | --- | --- | --- | --- | --- |
| %/brix | A1 | A2 | A4 | A5 | A6 | A7 | A8 |
| Maltotriose | 0.401 | 0.312 | 0.298 | 0.276 | 0.288 | 0.419 | 0.305 |
| maltose | 1.078 | 0.581 | 0.815 | 0.598 | 0.941 | 0.775 | 0.739 |

-continued

| Concentration of Sugars and Organic Acids in the Fermentation Media | | | | | | | |
|---|---|---|---|---|---|---|---|
| glucose | 8.883 | 23.122 | 24.138 | 24.698 | 25.304 | 25.444 | 25.537 |
| fructose | 1.122 | 0.000 | 0.000 | 0.000 | 0.000 | 0.000 | 0.000 |
| lactic acid | 18.404 | 6.884 | 5.496 | 4.672 | 2.707 | 1.521 | 1.579 |
| glycerol | 0.386 | 0.292 | 0.319 | 0.350 | 0.328 | 0.299 | 0.301 |
| formic acid | 0.302 | 0.263 | 0.282 | 0.407 | 0.280 | 0.234 | 0.233 |
| acetic acid | 10.267 | 7.967 | 8.219 | 8.296 | 8.143 | 7.899 | 8.091 |
| ethanol | 3.979 | 0.068 | 0.062 | 0.094 | 0.057 | 0.055 | 0.071 |

| %/brix | Z1 | Z2 | Z4 | Z5 | Z6 | Z7 | Z8 |
|---|---|---|---|---|---|---|---|
| Maltotriose | 0.406 | 0.282 | 0.265 | 0.311 | 0.247 | 0.291 | 0.318 |
| maltose | 0.810 | 0.722 | 1.007 | 0.750 | 0.726 | 0.895 | 0.876 |
| glucose | 10.064 | 22.988 | 24.153 | 24.698 | 25.353 | 25.501 | 25.740 |
| fructose | 0.000 | 0.000 | 0.000 | 0.000 | 0.000 | 0.000 | 0.000 |
| lactic acid | 17.820 | 6.742 | 5.081 | 2.995 | 1.351 | 1.431 | 1.652 |
| glycerol | 0.404 | 0.343 | 0.337 | 0.321 | 0.320 | 0.335 | 0.346 |
| formic acid | 0.331 | 0.303 | 0.309 | 0.281 | 0.267 | 0.263 | 0.299 |
| acetic acid | 10.399 | 8.273 | 8.247 | 8.026 | 7.969 | 8.026 | 8.261 |
| ethanol | 3.783 | 0.057 | 0.083 | 0.067 | 0.059 | 0.065 | 0.148 |

Note that the MRS media originally contained 7% acetate; therefore 7% should be subtracted from the values for acetate in the above table to ascertain the amount of acetate generated during the assay.

Each tube was thoroughly mixed to suspend settled cells and the absorbance was measured again at 600 nm. The final absorbance values for each sample were corrected for their respective background (taken just after inoculation, scattered light from added cells). The corrected absorption values were a measure of *W. viridescens* growth. The corrected values were plotted against nisin concentration and minimum inhibiting concentration approximated via regression. Exemplary absorbance results are provided in the table below.

| Tube #: | MRS, g: | Test med., g: | inoc, g: | gtot: | Nisin, µg/g: | 91416 ABS 610i: | 91516 ABS 610f: | Corrected ABS 610rs: |
|---|---|---|---|---|---|---|---|---|
| A1 | 5.05046 | 0.00000 | 0.24848 | 5.29894 | 0.00 | 0.465 | 2.333 | 1.868 |
| A2 | 4.96543 | 0.05497 | 0.24044 | 5.26084 | 0.33 | 0.462 | 1.568 | 1.106 |
| A3 | 4.88322 | 0.11358 | 0.25644 | 5.25324 | 0.68 | 0.468 | 1.531 | 1.063 |
| A4 | 4.75224 | 0.23120 | 0.26348 | 5.24692 | 1.38 | 0.466 | 1.334 | 0.868 |
| A5 | 4.52853 | 0.52264 | 0.2531 | 5.30437 | 3.08 | 0.438 | 0.911 | 0.473 |
| A6 | 4.01513 | 1.00698 | 0.24562 | 5.26773 | 5.97 | 0.42 | 0.536 | 0.116 |
| A7 | 3.50321 | 1.4864 | 0.24991 | 5.23952 | 8.86 | 0.402 | 0.403 | 0.001 |
| A8 | 3.01078 | 1.99641 | 0.24476 | 5.25195 | 11.87 | 0.36 | 0.361 | 0.001 |
| Z1 | 5.03594 | 0.00000 | 0.25228 | 5.28822 | 0.00 | 0.469 | 2.361 | 1.892 |
| Z2 | 4.94155 | 0.05345 | 0.25405 | 5.24905 | 0.34 | 0.472 | 1.618 | 1.146 |
| Z3 | 4.89029 | 0.12073 | 0.25478 | 5.26580 | 0.77 | 0.464 | 1.526 | 1.062 |
| Z4 | 4.75115 | 0.24831 | 0.25259 | 5.25205 | 1.58 | 0.455 | 1.296 | 0.841 |
| Z5 | 4.52267 | 0.50221 | 0.25131 | 5.27619 | 3.19 | 0.442 | 0.801 | 0.359 |
| Z6 | 4.03195 | 0.99365 | 0.25415 | 5.27975 | 6.31 | 0.423 | 0.426 | 0.003 |
| Z7 | 3.50064 | 1.49004 | 0.24365 | 5.23433 | 9.54 | 0.383 | 0.384 | 0.001 |
| Z8 | 3.06159 | 2.00403 | 0.25834 | 5.32396 | 12.61 | 0.385 | 0.386 | 0.001 |

*W. viridescens* Culture Absorbance (600 nm)

The data shown in the above table are plotted in FIG. 38, which graphically illustrates that minimal inhibitory concentration of each peptide was between 5 and 7 µg/g.

These data indicate that nisin A and nisin Z can effectively inhibit bacterial (*Weissella viridescens* NRRL B-1951) growth.

REFERENCES

1. Kuriki, T., Yanase, M., Takata, H., Takesada, Y., Imanaka, T. and Okada, S. (1993). A New Way of Producing Isomalto-Oligosaccharide Syrup by Using the Transglycosylation Reaction of Neopullalanase. Appl. Env. Microbiol. 59 (4), pp. 953-959.
2. Sakano, Y., Kogure, M., Kobayashi, T., Tamura, M. and Suekane, M. (1978). Carbohydrate Res. 61 (1), pp. 175-179.
3. Brooker, B. E. (1977). Ultrastructural Surface Changes Associated with Dextran Synthesis by *Leuconostoc mesenteroides*. J. Bacteriol. 131 (1), pp. 288-292.
4. Robyt, J. F., Yoon, S-H., and Mukerjea, R. (2008). Dextransucrase and the mechanism for dextran biosynthesis. Carbohydr. Res. 343 (18), pp. 3039-3048.
5. Kothari, D. and Goyal, A. (2015). Enzyme-resistant isomalto-oligosaccharides produced from *Leuconostoc mesenteroides* NRRL B-1426 dextran hydrolysis for functional food application. Biotechnol. Appl. Biochem. Published online 21 Sep. 2015. DOI: 10.1002/bab.1391.
6. Hu, Y., Ketabi, A., Buchko, A., and Ganzle, M. G. (2013). Metabolism of isomalto-oligosaccharides by *Lactobacillus reuteri* and bifidobacteria. Lett. Appl. Microbiol. 57, pp, 108-114.
7. Moller, M. S., Fredslund, F., Majumder, A., Nakai, H., Poulsen, J-C., N., Leggio, L. L., Svensson, B., and Hachem, M. A. (2012). Enzymology and Structure of the GH13_31 Glucan 1,6-a-Glucosidase That Confers Isomaltooligosaccharide Utilization in the Probiotic *Lactobacillus acidophilus* NCFM. J. Bacteriol. 194 (16), pp. 4249-4259.
8. Dols, M., Chraibi, W., Remaud-Simeon, M., Lindley, N. D., and Monsan, P. F. (1997). Growth and Energetics of *Leuconostoc mesenteroides* NRRL B-1299 during Metabolism of Various Sugars and Their Consequences for Dextransucrase Production. Appl. Env. Microbiol. 63 (6), pp. 2159-2165.
9. Dols, M., Remaud-Simeon, M., Willemot, R. M., Vignon, M. and Monsan, P. (1998). Appl. Env. Microbiol. 64 (4), pp. 1298-1302.
10. Cho, S. K., Eom, H. J., Moon, J. S., Lim, S. B., Kim, Y. K., Lee, K. W. and Han, N. S. (2014). An improved process of isomaltooligosaccharide production in *kimchi* involving the addition of a *Leuconostoc* starter and sugars. Int. J. Food Microbiol. 170, pp. 61-64.
11. Tieking, M., Korakli, M., Ehrmann, M. A., Ganzle, M. G., and Vogel, R. F. (2003). In situ Production of Exopolysaccharides during Sourdough Fermentation by Cereal and Intestinal Isolates of Lactic Acid Bacteria. Appl. Env. Microbiol. 69 (2), pp. 945-952.
12. Corsetti, A. and Settanni, L. (2007). Lactobacilli in sourdough fermentation. Food Res. Int. 40, pp. 539-558.
13. Lee, M-E., Jang, J-Y., Lee, J-H., Park, H-W., Choi, H-J. and Kim, T-W. (2015). Starter Cultures for *Kimchi* Fermentation. J. Microbiol. Biotechnol. 25 (5), pp. 559-568.
14. Mozzi, F., Vaningelgem, F., Hebert, E-M., Van der Meulen, R., Foulquie Moreno, M. R., Font de Valdez, G., and De Vuyst, L. (2006). Diversity of Heteropolysaccharide-Producing Lactic Acid Bacterium Strains and Their Biopolymers. Appl. Env. Microbiol. 72 (6), pp. 4431-4435.
15. Madsen II, L. R., Adams, K. L. and Gillevet, P. (2014). High-throughput PCR Sequencing of 16S rRNA in an Auto-inoculated, unfortified Sourdough starter From Red Wheat Flour. Unpublished in-house R&D work.
16. Madsen II, L. R. and Stanley, S. (2015). Fermentation using NRRL B-1299 to produce Maltosyl-isomaltooligosaccharides: analysis of 20 L fermentation broth via HPAEC-PAD. Unpublished in-house R&D work.
17. Patel, S., Kothari, D. and Goyal, A. (2011). Purification and Characterization of an Extracellular Dextransucrase from *Pediococcus pentosaceus* Isolated from Soil of North East India. Food. Technol. Biotechnol. 49 (3), pp. 297-303).
18. Dols-Lafargue, M., Willemot, R-M., Monsan, P. F. and Remaud-Simeon, M. (2001). Factors Affecting a-1,2 Glucooligosaccharide Synthesis by *Leuconostoc mesenteroides* NRRL B-1299 Dextransucrase. Biotechnol. Bioeng. 74 (6), pp. 498-504.
19. Chludzinski, A. M., Germaine, G. R. and Schachtele, C. F. (1974). Purification and Properties of Dextransucrase from *Streptococcus mutans*. J. Bacteriol. 118 (1), pp. 1-7.
20. Miller, A. W., Eklund, S. H. and Robyt, J. F. (1986). Milligram to gram scale purification and characterization of dextransucrase from *Leuconostoc mesenteroides* NRRL B-512F. Carbohydr. Res. 147 (1), pp. 119-133.
21. Goyal, A., Nigam, M., and Katiyar, S. S. (1995). Optimal conditions for production of dextransucrase from *Lecuonostoc mesenteroides* NRLL (NRRL) B-512F and its properties. J. Basic Microbiol. 35 (6), pp. 375-384.
22. Sarwat, F., Ul Qader, S-A., Aman, A. and Ahmed, N. (2008). Production & Characterization of a Unique Dextran from an Indigenous *Leuconostoc mesenteroides* CMG713. Int. J. Biol. Sci. 4 (6), pp. 379-386.
23. Monchois, V., Reverte, A., Remaud-Simeon, M., Monsan, P. and Willemot, R-M. (1998). Effect of *Leuconostoc mesenteroides* NRRL B-512F Dextransucrase Carboxy-Terminal Deletions on Dextran and Oligosaccharide Synthesis. Appl. Env. Microbiol. 64 (5), pp. 1644-1649.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The following statements describe and summarize various embodiments of the invention according to the foregoing description in the specification.

Statements:

1. A composition comprising maltosyl-isomaltooligosaccharides with a mass average molecular weight distribution of about 640 to 1000 daltons.
2. The composition of statement 1, comprising a mass average molecular weight distribution of about 730 to 900 daltons.
3. The composition of statement 1 or 2, where the maltosyl-isomaltooligosaccharides contain more α-(1→6) glucosyl linkages than α-(1,2), α-(1,3), or α-(1,4) glucosyl linkages.
4. The composition of any of statements 1-3, where at least 60%, or at least 70%, or at least 75%, or at least 80%, or at least 85%, or at least 90% of the maltosyl-isomaltooligosaccharides have at least 50% α-(1,6) glucosyl linkages, or at least 52% α-(1,6) glucosyl linkages, or at least 55% α-(1,6) glucosyl linkages, or at least 60% α-(1,6) glucosyl linkages, or at least 65% α-(1,6) glucosyl linkages, or at least 70% α-(1,6) glucosyl linkages, or at least 75% α-(1,6) glucosyl linkages, or at least 80% α-(1,6) glucosyl linkages, or at least 85% α-(1,6) glucosyl linkages, or at least 87% α-(1,6) glucosyl linkages, or at least 89% α-(1,6) glucosyl linkages, or at least 90% α-(1,6) glucosyl linkages.
5. The composition of any of statements 1-3, where the maltosyl-isomaltooligosaccharides have at least 80%, or at least 85%, or at least 89% α-(1,6) glucosyl linkages, or at least 90% α-(1,6) glucosyl linkages as detected by HPLC or NMR.
6. The composition of any of statements 1-5, where the maltosyl-isomaltooligosaccharides can optionally have one or two α-(1,4) linkages.
7. The composition of any of statements 1-6, where the maltosyl-isomaltooligosaccharides can optionally have one [—O-α-(1,4)-] linkage at the reducing end.
8. The composition of any of statements 1-7, where the maltosyl-isomaltooligosaccharides have no more than about 18 glucose units, or no more than about 16 glucose units, or no more than about 15 glucose units, or no more than about 14 glucose units, or no more than about 13 glucose units, or no more than about 12 glucose units, or no more than about 11 glucose units, or no more than about 10 glucose units as detected by HPAEC-PAD or HPLC-RID.
9. The composition of any of statements 1-8, where the maltosyl-isomaltooligosaccharides have a maltose unit at the reducing end.

10. The composition of any of statements 1-9, with less than 2%/brix isomaltose, or less than 1%/brix isomaltose, or less than 0.5%/brix isomaltose, or less than 0.2%/brix isomaltose, or less than 0.1%/brix isomaltose as detected by HPAEC-PAD or HPLC-RID.
11. The composition of any of statements 1-10, with less than 5%/brix glucose, or less than 4%/brix glucose, or less than 3%/brix glucose, or less than 2%/brix glucose, or less than 1%/brix glucose as detected by HPAEC-PAD or HPLC-RID.
12. The composition of any of statements 1-11, with less than 5%/brix sucrose, or less than 4%/brix sucrose, or less than 3%/brix sucrose, or less than 2%/brix sucrose, or less than 1%/brix sucrose as detected by HPAEC-PAD or HPLC-RID.
13. The composition of any of statements 1-12, with less than 4%/brix fructose, or less than 3%/brix fructose, or less than 2%/brix fructose, or less than 1%/brix fructose, or less than 0.5%/brix fructose, or less than 0.25%/brix fructose as detected by HPAEC-PAD or HPLC-RID.
14. The composition of any of statements 1-13, with less than 7%/brix lactate, or less than 6%/brix lactate, or less than 5%/brix lactate, or less than 3%/brix lactate, or less than 2%/brix lactate, or less than 1%/brix lactate, or less than 0.5%/brix lactate, or less than 0.2%/brix lactate, or less than 0.1%/brix lactate as detected by HPAEC-PAD or HPLC-RID.
15. The composition of any of statements 1-14, with less than 8%/brix maltose, or less than 7%/brix maltose, or less than 6%/brix maltose, or less than 5%/brix maltose as detected by HPAEC-PAD or HPLC-RID.
16. The composition of any of statements 1-15, with more than 3%/brix mannitol, or more than 4%/brix mannitol, or more than 5%/brix mannitol as detected by HPAEC-PAD or HPLC-RID.
17. The composition of any of statements 1-16, with less than 30%/brix mannitol, or less than 20%/brix mannitol, or less than 15% mannitol or less than 12%/brix mannitol, or less than 10% mannitol, or less than 9%/brix mannitol, or less than 8% mannitol as detected by HPAEC-PAD or HPLC-RID.
18. The composition of any of statements 1-17, with the compositions less than 4%/brix glycerol, or less than 3%/brix glycerol, or less than 2%/brix glycerol, or less than 1%/brix glycerol, or less than 0.6%/brix glycerol, or less than 0.5%/brix glycerol detectable by HPLC-RID or HPLC-RID.
19. The composition of any of statements 1-18, with less than 20%/brix MIMO-DP3, or less than 19%/brix MIMO-DP3, or less than 18%/brix MIMO-DP3, or less than 17%/brix MIMO-DP3, or less than 16%/brix MIMO-DP3, or less than 15%/brix MIMO-DP3.
20. The composition of any of statements 1-19, with less than 30%/brix MIMO-DP4, or less than 28%/brix MIMO-DP4, or less than 27%/brix MIMO-DP4, or less than 26%/brix MIMO-DP4, or less than 25%/brix MIMO-DP4, or less than 24%/brix MIMO-DP4, or less than 23%/brix MIMO-DP4.
21. The composition of any of statements 1-20, with more than 18%/brix MIMO-DP5, or more than 19%/brix MIMO-DP5, or more than 20%/brix MIMO-DP5, or more than 21%/brix MIMO-DP5, or more than 22%/brix MIMO-DP5, or more than 23%/brix MIMO-DP5, or more than 23.5%/brix MIMO-DP5, or more than 24%/brix MIMO-DP5, or more than 25%/brix MIMO-DP5.
22. The composition of any of statements 1-21, with more than 10%/brix MIMO-DP6, or more than 11%/brix MIMO-DP6, or more than 12%/brix MIMO-DP6, or more than 13%/brix MIMO-DP6, or more than 14%/brix MIMO-DP6, or more than 14.5%/brix MIMO-DP6, or more than 15%/brix MIMO-DP6.
23. The composition of any of statements 1-22, with more than 1%/brix MIMO-DP7, or more than 2%/brix MIMO-DP7, or more than 3%/brix MIMO-DP7, or more than 3.5%/brix MIMO-DP7, or more than 4%/brix MIMO-DP7, or more than 5%/brix MIMO-DP7, or more than 5.5%/brix MIMO-DP7.
24. The composition of any of statements 1-23, with more than 0.5%/brix MIMO-DP8, or more than 1%/brix MIMO-DP8, or more than 1.5%/brix MIMO-DP8, or more than 1.75%/brix MIMO-DP8, or more than 2%/brix MIMO-DP8, or more than 2.25%/brix MIMO-DP8.
25. The composition of any of statements 1-24, with more than 0.1%/brix MIMO-DP9, or more than 0.2%/brix MIMO-DP9, or more than 0.3%/brix MIMO-DP9, or more than 0.4%/brix MIMO-DP9, or more than 0.5%/brix MIMO-DP9.
26. The composition of any of statements 1-25, containing the components shown in FIG. 39.
27. The composition of any of statements 1-26, as a concentrated solution.
28. The composition of any of statements 1-27, dried as a powder, for example, by drying, spray drying or by freeze-drying.
29. The composition of any of statements 1-28, aliquoted into individual servings for human or animal consumption.
30. The composition of any of statements 1-29, aliquoted into individual serving of about 0.25 ml to about 10 ml, or about 0.5 ml to about 8 ml, or about 0.75 ml to about 7 ml, or about 1 ml to about 5 ml, or about 1 ml to about 3 ml.
31. A method comprising administering the composition of any of statements 1-30 to an animal (e.g., a human or a domesticated animal).
32. A method for the preparation of a composition comprising:
  (a) contacting a feedstock comprising *Leuconostoc citreum* ATCC 13146 (NRRL B-742) bacterial cells with a ratio of sucrose to maltose ranging from 2.0 to about 4.5 in an aqueous culture to form a fermentation mixture;
  (b) fermenting the fermentation mixture at a pH between 4 and 8;
  (c) removing the bacterial cells to generate a cell-free liquor;
  (d) polishing the cell-free liquor by removal of insoluble impurities; decolorization (e.g., using activated charcoal, activated carbon, a weak base anion resin, or a combination thereof), de-aching (e.g., using a strong acid cation resin to remove metal ions, or using a two-step process using a strong acid followed by a weak base); removing protein (e.g., by heating, evaporating the aqueous culture medium, and centrifugation or filtration, or by using a weak base anion resin); removing organic acids (e.g., utilizing a weak base anion resin, liquid chromatography using a chromatographic grade gel-type strong acid cation exchange resin in calcium form (SAC-$Ca^{++}$); or any combination thereof, to generate a polished product;

e) washing insoluble impurities, decolorization agents, de-ashing agents, evaporating mechanisms (e.g., a wiped film evaporator), centrifugation pellets, filters, resins, weak base anion resins, chromatographic resins, chromatographic grade gel-type or macroporous strong acid cation exchange resins, or any combination thereof to generate one or more washes; and combining one or more washes together, or with the cell-free liquor; or with the polished product;

wherein the final composition comprises maltosyl-isomaltooligosaccharides with a mass average molecular weight distribution of about 640 to 1000 daltons and at least 3% mannitol.

33. The method of statement 32, where the maltosyl-isomaltooligosaccharides have at least 50% α-(1,6) glucosyl linkages, or at least 52% α-(1,6) glucosyl linkages, or at least 55% α-(1,6) glucosyl linkages, or at least 60% α-(1,6) glucosyl linkages, or at least 65% α-(1,6) glucosyl linkages, or at least 70% α-(1,6) glucosyl linkages, or at least 75% α-(1,6) glucosyl linkages, or at least 80% α-(1,6) glucosyl linkages, or at least 85% α-(1,6) glucosyl linkages, or at least 89% α-(1,6) glucosyl linkages, or at least 90% α-(1,6) glucosyl linkages.

34. The method of statement 32 or 33, where the ratio of sucrose to maltose ranges from about 2.0 to about 4.5, from about 2.2 to about 4.3, or about 2.3 to about 4.0, or about 2.4 to about 4.0, or about 2.5 to about 3.75, or about 2.5 to about 3.5, or about 2.5 to about 3.0, or about 2.75.

35. A composition generated by a method comprising
    (a) contacting a feedstock comprising *Leuconostoc citreum* ATCC 13146 (NRRL B-742) bacterial cells with a ratio of sucrose to maltose ranging from 2.0 to about 4.5 in an aqueous culture to form a fermentation mixture;
    (b) fermenting the fermentation mixture at a pH between 4 and 8;
    (c) removing the bacterial cells to generate a cell-free liquor;
    (d) polishing the cell-free liquor by removal of insoluble impurities; decolorization (e.g., using activated charcoal, activated carbon, a weak base anion resin, or a combination thereof), de-aching (e.g., using a strong acid cation resin to remove metal ions, or using a two-step process using a strong acid followed by a weak base); removing protein (e.g., by heating, evaporating the aqueous culture medium, and centrifugation or filtration, or by using a weak base anion resin); removing organic acids (e.g., utilizing a weak base anion resin, liquid chromatography using a chromatographic grade gel-type strong acid cation exchange resin in calcium form (SAC-Ca$^{++}$); or any combination thereof, to generate a polished product;
    e) washing insoluble impurities, decolorization agents, de-ashing agents, evaporating mechanisms (e.g., a wiped film evaporator), centrifugation pellets, filters, ration, weak base anion resins, chromatographic resins, chromatographic grade gel-type strong acid cation exchange resins, or any combination thereof to generate one or more washes; and combining one or more washes together, or with the cell-free liquor; or with the polished product;

wherein the final composition comprises maltosyl-isomaltooligosaccharides with a mass average molecular weight distribution of about 640 to 1000 daltons and at least 3% mannitol.

36. The composition of statement 35, where at least 60%, or at least 70%, or at least 75%, or at least 80%, or at least 85%, or at least 90% of the maltosyl-isomaltooligosaccharides have at least 50% α-(1,6) glucosyl linkages, or at least 52% α-(1,6) glucosyl linkages, or at least 55% α-(1,6) glucosyl linkages, or at least 60% α-(1,6) glucosyl linkages, or at least 65% α-(1,6) glucosyl linkages, or at least 70% α-(1,6) glucosyl linkages, or at least 89% α-(1,6) glucosyl linkages, or at least 90% α-(1,6) glucosyl linkages.

37. The composition of statement 35 or 36, where the sucrose to maltose ranges from about 2.0 to about 4.5, from about 2.2 to about 4.3, or about 2.3 to about 4.0, or about 2.4 to about 4.0, or about 2.5 to about 3.75, or about 2.5 to about 3.5, or about 2.5 to about 3.0, or about 2.75.

The specific compositions and methods described herein are representative, exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications can be made to the invention disclosed herein without departing from the scope and spirit of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by embodiments and optional features, modification and variation of the concepts herein disclosed may be resorted to by those skilled in the art, and that such modifications and variations are considered to be within the scope of this invention as defined by the appended claims and statements of the invention.

The invention illustratively described herein may be practiced in the absence of any element or elements, or limitation or limitations, which is not specifically disclosed herein as essential. The methods and processes illustratively described herein may be practiced in differing orders of steps, and the methods and processes are not necessarily restricted to the orders of steps indicated herein or in the claims.

As used herein and in the appended claims, the singular forms "a," "an," and "the" include plural reference unless the context clearly dictates otherwise. Thus, for example, a reference to "a compound" or "an oligosaccharide" or "a maltose" includes a plurality of such compounds, oligosaccharides, or maltose sugars, and so forth. In this document, the term "or" is used to refer to a nonexclusive or, such that "A or B" includes "A but not B," "B but not A," and "A and B," unless otherwise indicated.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

The Abstract is provided to comply with 37 C.F.R. § 1.72(b) to allow the reader to quickly ascertain the nature and gist of the technical disclosure. The Abstract is submitted with the understanding that it will not be used to interpret or limit the scope or meaning of the claims.

What is claimed is:

1. A composition comprising maltosyl-isomaltooligosaccharides with a mass average molecular weight distribution of about 730 to 900 daltons, and where at least 60% of the maltosyl-isomaltooligosaccharides have at least 75% α-(1,6) linkages, and wherein at least 40% of the maltosyl-isomaltooligosaccharides in the composition have a degree of polymerization (DP) of 5 or more.

2. The composition of claim 1, where the maltosyl-isomaltooligosaccharides have no more than about 18 glucose units.

3. The composition of claim 1, where the maltosyl-isomaltooligosaccharides have a maltose unit at the reducing end.

4. The composition of claim 1, with less than 2%/brix isomaltose.

5. The composition of claim 1, with less than 5%/brix glucose.

6. The composition of claim 1, with less than 5%/brix sucrose.

7. The composition of claim 1, with less than 4%/brix fructose.

8. The composition of claim 1, with less than 7%/brix lactate.

9. The composition of claim 1, with less than 8%/brix maltose.

10. The composition of claim 1, with 3% or more than 3%/brix mannitol.

11. The composition of claim 1, with less than 4%/brix glycerol.

12. The composition of claim 1, with less than 20%/brix MIMO-DP3.

13. The composition of claim 1, with less than 30%/brix MIMO-DP4.

14. The composition of claim 1, with more than 18%/brix MIMO-DP5.

15. The composition of claim 1, with more than 10%/brix MIMO-DP6.

16. The composition of claim 1, with more than 1%/brix MIMO-7.

17. The composition of claim 1, with more than 0.5%/brix MIMO-DP8.

18. The composition of claim 1, with more than 0.1%/brix MIMO-DP9.

19. The composition of claim 1, as a concentrated solution.

20. The composition of claim 1, dried as a powder.

21. The composition of claim 1, aliquoted into individual servings for human or animal consumption.

22. The composition of claim 1, aliquoted into individual serving of about 0.25 ml to about 10 ml.

23. A composition generated by a method comprising
   (a) contacting a feedstock comprising *Leuconostoc citreum* ATCC 13146 (NRRL B-742) bacterial cells with a fixed ratio of sucrose to maltose ranging from 2.1 to about 4.5 in an aqueous culture to form a fermentation mixture;
   (b) fermenting the fermentation mixture at a pH between 4 and 8;
   (c) removing the bacterial cells to generate a cell-free liquor;
   (d) polishing the cell-free liquor by removal of insoluble impurities; decolorization; de-ashing); removing protein; removing organic acids; or any combination thereof, to generate a polished product;
   e) washing insoluble impurities, decolorization agents, de-ashing agents, evaporating mechanisms, centrifugation pellets, filters, resins, weak base anion resins, chromatographic resins, chromatographic grade gel-type strong acid cation exchange resins, or any combination thereof to generate one or more washes; and combining the one or more washes together, or combining the one or more washes with the cell-free liquor; or combining the one or more washes with the polished product;
   wherein the final composition comprises maltosyl-isomaltooligosaccharides with a mass average molecular weight distribution of about 730 to 900 to daltons, where at least 60% of the maltosyl-isomaltooligosaccharides have at least 75% α-(1,6) linkages, and wherein at least 40% of the maltosyl-isomaltooligosaccharides in the composition have a degree of polymerization (DP) of 5 or more.

* * * * *

UNITED STATES PATENT AND TRADEMARK OFFICE
CERTIFICATE OF CORRECTION

PATENT NO. : 10,632,141 B2  
APPLICATION NO. : 15/409223  
DATED : April 28, 2020  
INVENTOR(S) : Madsen, II et al.

Page 1 of 1

It is certified that error appears in the above-identified patent and that said Letters Patent is hereby corrected as shown below:

In the Claims

In Column 56, Line 45, in Claim 23, before "daltons,", delete "to"

Signed and Sealed this  
Eleventh Day of August, 2020

Andrei Iancu  
*Director of the United States Patent and Trademark Office*